(12) United States Patent
Yen et al.

(10) Patent No.: US 11,407,757 B2
(45) Date of Patent: Aug. 9, 2022

(54) HETEROCYCLE COMPOUNDS AS TYRO3, AXL AND MERTK (TAM) FAMILY OF RECEPTOR TYROSINE KINASE INHIBITORS

(71) Applicant: Development Center for Biotechnology, Taipei (TW)

(72) Inventors: Shih-Chieh Yen, Taipei (TW); Chu-Bin Liao, Taipei (TW); Hui-Chen Wang, Taipei (TW); Po-Ting Chen, Taipei (TW); Yu-Chih Pan, Taipei (TW); Tsung-Hui Li, Taipei (TW); Bo-Rong Chen, Taipei (TW); Shian-Yi Chiou, Taipei (TW)

(73) Assignee: Development Center for Biotechnology, Taipei (TW)

( * ) Notice: Subject to any disclaimer, the term of this patent is extended or adjusted under 35 U.S.C. 154(b) by 0 days.

(21) Appl. No.: 16/958,721

(22) PCT Filed: Dec. 26, 2018

(86) PCT No.: PCT/US2018/067532
§ 371 (c)(1),
(2) Date: Jun. 28, 2020

(87) PCT Pub. No.: WO2019/133629
PCT Pub. Date: Jul. 4, 2019

(65) Prior Publication Data
US 2021/0009597 A1 Jan. 14, 2021

Related U.S. Application Data

(60) Provisional application No. 62/610,994, filed on Dec. 28, 2017.

(51) Int. Cl.
*C07D 487/04* (2006.01)
*A61P 35/00* (2006.01)

(52) U.S. Cl.
CPC ............ *C07D 487/04* (2013.01); *A61P 35/00* (2018.01)

(58) Field of Classification Search
CPC ............................. A61P 35/00; C07D 487/04
See application file for complete search history.

(56) References Cited

FOREIGN PATENT DOCUMENTS

WO    WO 2014/113429    *   7/2014    ........... A61K 31/519

* cited by examiner

*Primary Examiner* — Erich A Leeser
(74) *Attorney, Agent, or Firm* — Liang Legal Group, PLLC

(57) ABSTRACT

Disclosed are compounds of formula (I) below and tautomers, stereoisomers, isotopologues, or pharmaceutically acceptable salts thereof:

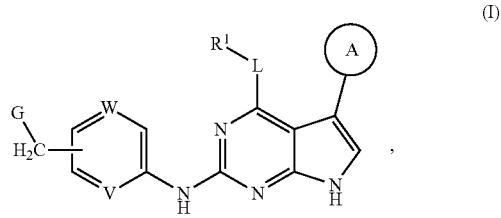

in which each of variables $R^1$, ring A, L, W, V, and G is defined herein. Also disclosed are a method for treating disease or disorder mediated by Tyro3, Axl, and/or Mer kinase with a compound of formula (I) or a tautomer, stereoisomer, isotopologue, or salt thereof and a pharmaceutical composition containing same.

20 Claims, No Drawings

HETEROCYCLE COMPOUNDS AS TYRO3, AXL AND MERTK (TAM) FAMILY OF RECEPTOR TYROSINE KINASE INHIBITORS

BACKGROUND

Receptor tyrosine kinases (RTKs) are transmembrane proteins for transducing signals from the extracellular environment to the cytoplasm and nucleus. They play important roles in regulating normal cellular processes, such as survival, growth, differentiation, adhesion, and motility.

As a unique class of RTKs, the TAM family, which consists of kinases Tyro3, Axl, and Mer, has been shown to mediate diverse cellular functions, including macrophage clearance of apoptotic cells, platelet aggregation, and natural killer cell differentiation. TAM RTKs, ectopically expressed or overexpressed in a wide variety of human cancers (e.g., solid tumor and hematological tumor), have been found to play a critical role at the interface of the innate and adaptive immune system by suppressing the innate immune response in a tumor microenvironment.

As inhibition of TAM RTKs reverses the immunosuppressive response, it holds promise as an approach for treating various diseases associated with Tyro3, Axl, and Mer, e.g., cancer and inflammation.

Although various tyrosine kinase inhibitors are shown to be useful therapeutics, there is still a need for specific TAM kinase inhibitor that have fewer and less deterious side effects for therapeutic use.

SUMMARY

The present invention relates to certain heterocycle compounds as RTK inhibitors for treating cancer. Unexpectedly, these compounds produce higher efficacies in inhibiting RTKs, e.g., Axl and Mer, as compared to other known therapeutic agents.

In one aspect of this invention, it covers the compounds of formula (I) below and tautomers, stereoisomers, isotopologues, or pharmaceutically acceptable salts thereof:

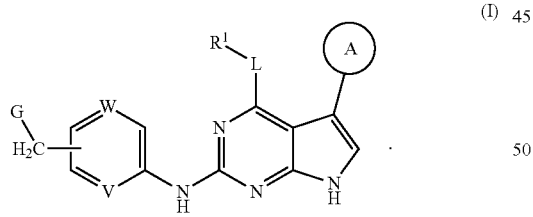

In this formula, $R^1$ is H, $C_{1-8}$ alkyl, $C_{3-8}$ cycloalkyl, $C_{1-8}$ heterocyclyl, aryl, or heteroaryl;
L is O, S, NH, or aryl;
Ring A is

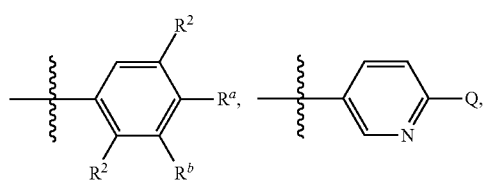

wherein one of $R^a$ and $R^b$ is Q and the other $R^a$ and $R^b$ is $R^2$;

Q is H, halogen, $OR^5$, $OCH_2Ar$, CN, $N_3$, $NO_2$, $N(R^5)(R^6)$, $N(R^5)CO(R^7)$, $C(O)R^5$, $C(O)OR^5$, $C(O)N(R^5)(R^6)$, $SO_2R^5$, $SO_2N(R^5)(R^6)$, $SOR^5$, $SR^5$, $NR^5SO_2R^7$, $C_{1-8}$ alkyl, $C_{2-8}$ alkenyl, $C_{2-8}$ alkynyl, $C_{3-8}$ cycloalkyl, $C_{1-8}$ heterocyclyl, aryl, or heteroaryl, in which each of $R^5$, $R^6$, and $R^7$, independently, is H, $C_{1-8}$ alkyl, $C_{3-8}$ cycloalkyl, $C_{3-8}$ heterocyclyl, aryl, or heteroaryl, or, $R^5$ and $R^6$, together with the atom to which they are attached, form $C_{3-8}$ cycloalkyl, $C_{3-8}$ heterocyclyl; and Ar is selected from benzodioxanyl, indazolyl, isoquinolinyl, isoxazolyl, naphthyl, oxadiazolyl, phenyl, pyridinyl, pyrimidinyl, pyridinonyl, and quinolinyl; wherein each ring is optionally substituted with 1, 2, 3, or 4 substituents independently selected from $C_1$-$C_4$ alkoxy, $C_1$-$C_4$ alkoxycarbonyl, $C_1$-$C_4$ alkoxycarbonylamino, $C_1$-$C_4$ alkyl, ($C_1$-$C_4$ alkyl)carbonyl, ($C_1$-$C_4$ alkyl)sulfonyl, amido, aminocarbonyl, aminocarbonyl($C_1$-$C_3$ alkyl), —$(CH_2)_qCO_2$ $C_1$-$C_4$ alkyl, —$(CH_2)_qOH$, carboxy, cyano, formyl, halo, halo $C_1$-$C_4$ alkyl, halo $C_1$-$C_4$ alkoxy, nitro, phenyl optionally substituted with one cyano group, phenyloxy optionally substituted with one halo group, phenylcarbonyl, pyrrole, and tetrahydropyran; and wherein q is 0, 1, 2, 3, or 4; each of the $C_{1-8}$ alkyl, $C_{2-8}$ alkenyl, $C_{2-8}$ alkynyl, $C_{3-8}$ cycloalkyl, $C_{1-8}$ heterocyclyl, aryl, and heteroaryl being optionally substituted with one or more moieties selected from the group consisting of halogen, $OR^5$, CN, $N_3$, $NO_2$, $N(R^5)(R^6)$, $N(R^5)CO(R^7)$, $C(O)R^5$, $C(O)OR^5$, $C(O)N(R^5)(R^6)$, $SO_2R^5$, $SO_2N(R^5)(R^6)$, $SOR^5$, $SR^5$, $NR^5SO_2R^7$, $C_{1-8}$ alkyl, $C_{1-8}$ alkoxyl, $C_{2-8}$ alkenyl, $C_{2-8}$ alkynyl, $C_{3-8}$ cycloalkyl, $C_{1-8}$ heterocyclyl, aryl, and heteroaryl.

each $R^2$ is independently H, halogen, OH, $CH_2OH$, CN, $CF_3$, $CH_3$, $OCH_3$, $OCF_3$, $N(CH_3)_2$, $R^3$ is H, $C_{1-4}$ alkyl, $C_{3-8}$ cycloalkyl, $C_{1-8}$ heterocyclyl, aryl, or heteroaryl;

$R^4$ is H, CN, $C_{1-4}$ alkyl, $C_{3-8}$ cycloalkyl, $C_{1-8}$ heterocyclyl, aryl, or heteroaryl;

each of W and V, independently, is N or $CR^8$, $R^8$ being H, halogen, $OR^5$, CN, $N_3$, $NO_2$, $N(R^5)(R^6)$, $N(R^5)CO(R^7)$, C(O)R$^5$, C(O)OR$^5$, C(O)N(R$^5$)(R$^6$), SO$_2$R$^5$, SO$_2$N(R$^5$)(R$^6$), SOR$^5$, SR$^6$, NR$^5$SO$_2$R$^7$, C$_{1-8}$ alkyl, C$_{2-8}$ alkenyl, C$_{2-8}$ alkynyl, C$_{3-8}$ cycloalkyl, C$_{1-8}$ heterocyclyl, aryl, or heteroaryl, in which each of R$^5$, R$^6$, and R$^7$, independently, is H, C$_{1-8}$ alkyl, C$_{3-8}$ cycloalkyl, C$_{1-8}$ heterocyclyl, aryl, or heteroaryl, or, R$^5$ and R$^6$, together with the atom to which they are attached, form C$_{3-8}$ cycloalkyl, C$_{3-8}$ heterocyclyl; and G is halogen, OR$^5$, CN, N$_3$, NO$_2$, NH(R$^9$), N(R$^9$)(R$^{10}$), N(R$^5$)CO(R$^7$), C(O)R$^5$, C(O)OR$^5$, C(O)N(R$^5$)(R$^6$), SO$_2$R$^5$, SO$_2$N(R$^5$)(R$^6$), SOR$^5$, SR$^5$, NR$^5$SO$_2$R$^7$, C$_{2-8}$ alkenyl, C$_{2-8}$ alkynyl, C$_{3-8}$ cycloalkyl, C$_{3-8}$ heterocyclyl, aryl, or heteroaryl, in which each of R$^9$ and R$^{10}$, independently, is C$_{1-8}$ alkyl, C$_{3-8}$ cycloalkyl, C$_{3-8}$ heterocyclyl, aryl, or heteroaryl, or, R$^9$ and R$^{10}$, together with the atom to which they are attached, form C$_{3-8}$ heterocyclyl, each of the C$_{1-8}$ alkyl, C$_{2-8}$ alkenyl, C$_{2-8}$ alkynyl, C$_{3-8}$ cycloalkyl, C$_{3-8}$ heterocyclyl, aryl, and heteroaryl being optionally substituted with one or more moieties selected from the group consisting of halogen, OR$^5$, CN, N$_3$, NO$_2$, N(R$^5$)(R$^6$), N(R$^5$)CO(R$^7$), C(O)R$^5$, C(O)OR$^5$, C(O)N(R$^5$)(R$^6$), SO$_2$R$^5$, SO$_2$N(R$^5$)(R$^6$), SOR$^5$, SR$^5$, NR$^5$SO$_2$R$^7$, C$_{1-8}$ alkyl, C$_{1-8}$ alkoxyl, C$_{2-8}$ alkenyl, C$_{2-8}$ alkynyl, C$_{3-8}$ cycloalkyl, C$_{3-8}$ heterocyclyl, aryl, and heteroaryl.

The term "alkyl" herein refers to a straight or branched hydrocarbon group, containing 1-20 (including any number between 1 and 20 carbons, such as 1-10 and 1-6) carbon atoms, such as methyl, ethyl, n-propyl, i-propyl, n-butyl, i-butyl, and t-butyl.

The term "alkenyl" refers to a linear or branched hydrocarbon moiety, having 2-20 carbons, that contains at least one double bond, such as —CH=CH—CH$_3$.

The term "alkynyl" refers to a linear or branched hydrocarbon moiety, having 2-20 carbons, that contains at least one triple bond, such as —C≡C—CH$_3$.

The term "cycloalkyl" refers to a saturated and partially unsaturated monocyclic, bicyclic, tricyclic, or tetracyclic hydrocarbon group having 3-12 (e.g., 3-10 and 3-8) carbon atoms. Examples include cyclopropyl, cyclobutyl, cyclopentyl, cyclopentenyl, cyclohexyl, cyclohexenyl, cycloheptyl, and cyclooctyl.

The term "heterocycloalkyl" refers to a nonaromatic 5-8 membered monocyclic, 8-12 membered bicyclic, or 11-14 membered tricyclic ring system having one or more heteroatoms (e.g., O, N, P, and S), such as piperazinyl, imidazolidinyl, azepanyl, pyrrolidinyl, dihydrothiadiazolyl, dioxanyl, morpholinyl, tetrahydropuranyl, and tetrahydrofuranyl.

The term "halogen" refers to a fluoro, chloro, bromo, or iodo radical. The term "amino" refers to a radical derived from amine, which is unsubstituted or mono-/di-substituted with alkyl, aryl, cycloalkyl, heterocycloalkyl, or heteroaryl.

The term "aryl" refers to a 6-carbon monocyclic, a 10-carbon bicyclic, or a 14-carbon tricyclic aromatic ring system, such as phenyl, naphthyl, and anthracenyl.

The term "heteroaryl" refers to an aromatic 5-8 membered monocyclic, 8-12 membered bicyclic, or 11-14 membered tricyclic ring system having one or more heteroatoms (e.g., O, N, P, and S). Examples include triazolyl, oxazolyl, thiadiazolyl, tetrazolyl, pyrazolyl, pyridyl, furyl, imidazolyl, benzimidazolyl, pyrimidinyl, thienyl, quinolinyl, indolyl, thiazolyl, and benzothiazolyl.

Alkyl, alkenyl, alkynyl, cycloalkyl, heterocycloalkyl, aryl, and heteroaryl mentioned herein include both substituted and unsubstituted moieties. Possible substituents on alkenyl, alkynyl, cycloalkyl, heterocycloalkyl, aryl, and heteroaryl include, but are not limited to, C$_1$-C$_{10}$ alkyl, C$_2$-C$_{10}$ alkenyl, C$_2$-C$_{10}$ alkynyl, C$_3$-C$_{20}$ cycloalkyl, C$_3$-C$_{20}$ cycloalkenyl, C$_1$-C$_{20}$ heterocycloalkyl, C$_1$-C$_{20}$ heterocycloalkenyl, C$_1$-C$_{10}$ alkoxy, aryl, aryloxy, heteroaryl, heteroaryloxy, amino, C$_1$-C$_{10}$ alkylamino, C$_1$-C$_{20}$ dialkylamino, arylamino, diarylamino, C$_1$-C$_{10}$ alkylsulfonamino, arylsulfonamino, C$_1$-C$_{10}$ alkylimino, arylimino, C$_1$-C$_{10}$ alkylsulfonimino, arylsulfonimino, hydroxyl, halogen, thio, C$_1$-C$_{10}$ alkylthio, arylthio, C$_1$-C$_{10}$ alkylsulfonyl, arylsulfonyl, acylamino, aminoacyl, aminothioacyl, amido, amidino, guanidine, ureido, thioureido, cyano, nitro, nitroso, azido, acyl, thioacyl, acyloxy, carboxyl, and carboxylic ester. On the other hand, possible substituents on alkyl include all the above-recited substituents except C$_1$-C$_{10}$ alkyl. Cycloalkyl, heterocycloalkyl, aryl, and heteroaryl can also be fused with each other.

In addition to the compounds of formula (I) described above, their pharmaceutically acceptable salts and solvates, where applicable, are also covered by this invention. A salt can be formed between an anion and a positively charged group (e.g., amino) on a compound. Examples of a suitable anion include chloride, bromide, iodide, sulfate, nitrate, phosphate, citrate, methanesulfonate, trifluoroacetate, acetate, malate, tosylate, tartrate, fumurate, glutamate, glucuronate, lactate, glutarate, and maleate. A salt can also be formed between a cation and a negatively charged group. Examples of a suitable cation include sodium ion, potassium ion, magnesium ion, calcium ion, and an ammonium cation such as tetramethylammonium ion. A salt further includes those containing quaternary nitrogen atoms. A solvate refers to a complex formed between an active compound and a pharmaceutically acceptable solvent. Examples of a pharmaceutically acceptable solvent include water, ethanol, isopropanol, ethyl acetate, acetic acid, and ethanolamine.

Another aspect of this invention is a pharmaceutical composition for treating RTK-associated diseases, e.g., cancer and inflammation.

The pharmaceutical composition contains one of the compounds of formula (I) described above or its tautomer, stereoisomer, isotopologue, or pharmaceutically acceptable salt and a pharmaceutically acceptable carrier.

This invention also covers use of such a composition for the manufacture of a medicament for treating a TAM RTK-associated disease.

A composition for oral administration can be any orally acceptable dosage form including capsules, tablets, emulsions and aqueous suspensions, dispersions, and solutions. In the case of tablets, commonly used carriers include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added. Oral solid dosage forms can be prepared by spray dried techniques; hot melt extrusion strategy, micronization, and nano milling technologies.

A nasal aerosol or inhalation composition can be prepared according to techniques well known in the art of pharmaceutical formulation. For example, such a composition can be prepared as a solution in saline, employing benzyl alcohol or other suitable preservatives, absorption promoters, fluorocarbons, and/or other solubilizing or dispersing agents known in the art. A composition having an active compound can also be administered in the form of suppositories for rectal administration.

The carrier in the pharmaceutical composition must be "acceptable" in the sense that it is compatible with the active ingredient of the composition (and preferably, capable of stabilizing the active ingredient) and not deleterious to the subject to be treated. One or more solubilizing agents can be utilized as pharmaceutical excipients for delivery of an active compound. Examples of other carriers include colloidal silicon oxide, magnesium stearate, cellulose, sodium lauryl sulfate, and D&C Yellow #10.

Still within the scope of the present invention is a method of treating an RTK-associated disease, e.g., cancer associated with Tyro3, Axl, or Mer kinase. A method of the invention includes administering to a subject in need thereof an effective amount of a compound of formula (I) or a tautomer, stereoisomer, isotopologue, or salt thereof.

The above-described compounds or a pharmaceutical composition containing one or more of them can be administered to a subject orally, parenterally, by inhalation spray, topically, rectally, nasally, buccally, or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques.

The term "treating" refers to application or administration of the compound to a subject with the purpose to cure, alleviate, relieve, alter, remedy, improve, or affect the disease, the symptom, or the predisposition. "An effective amount" refers to the amount of the compound which is required to confer the desired effect on the subject. Effective amounts vary, as recognized by those skilled in the art, depending on route of administration, excipient usage, and the possibility of co-usage with other therapeutic treatments such as use of other active agents.

The details of one or more embodiments of the invention are set forth in the description below. Other features, objects, and advantages of the invention will be apparent from the description and from the claims.

DETAILED DESCRIPTION

Disclosed in detail below are the compounds of formula (I), as well as tautomers, stereoisomers, isotopologues, or pharmaceutically acceptable salts thereof:

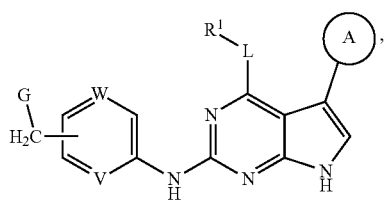

(I)

in which each of variables $R^1$, Ring A, L, W, V, and G are as defined in SUMMARY section.

Referring to formula (I) above, while L is preferably O, and G is preferably $N(R^9)(R^{10})$ or $C_{3-8}$ heterocyclyl.

When G is $N(R^9)(R^{10})$, each of $R^9$ and $R^{10}$, independently, can be $C_{1-8}$ alkyl, $C_{3-8}$ cycloalkyl, or $C_{3-8}$ heterocyclyl, or $R^9$ and $R^{10}$, together with the atom to which they are attached, form $C_{1-8}$ heterocyclyl.

In one embodiment, compounds of formula (I) have G being $N(R^9)(R^{10})$, in which $R^9$ and $R^{10}$, together with the atom to which they are attached, form $C_{3-8}$ heterocyclyl. For example, G is

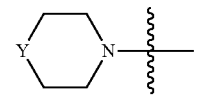

optionally substituted with one or more $C_{1-8}$ alkyl, in which Y is O, —NR, or —CR'R", each of R, R', and R", independently, being H, OH, $NH_2$, or $C_{1-8}$ alkyl. Preferably, Y is —NR, R being H or $C_{1-8}$ alkyl; or Y is —CR'R", each of R' and R", independently, being H, OH, $NH_2$, or $C_{1-8}$ alkyl. Exemplary compounds include

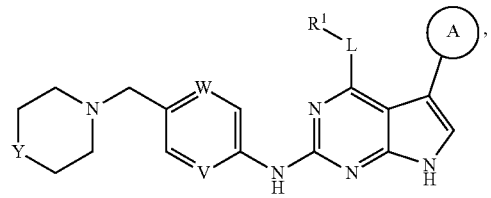

in which each of W and V, independently, is N or $CR^8$, $R^8$ being H, halogen, $OR^5$, $N(R^5)(R^6)$, or $C_{1-8}$ alkyl, and the Y-containing heterocyclyl is optionally substituted with one or more $C_{1-8}$ alkyl.

When G is $C_{3-8}$ heterocyclyl, the $C_{3-8}$ heterocyclyl is preferably a 5- or 6-membered ring. Examples of the 5- or 6-membered ring include, but are not limited to,

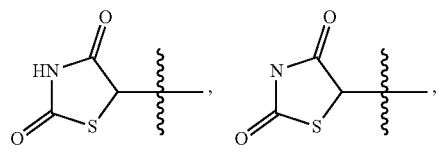

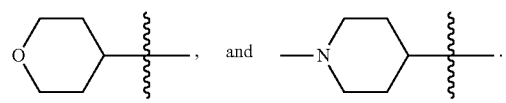

Referring back to formula (I), Ring A is preferably aryl. Examples include phenyl, which is unsubstituted or substituted with one to three moieties selected from halogen, $OR^5$, $OCH_2Ar$, CN, $N(R^5)(R^6)$, $N(R^5)CO(R^7)$, $C(O)OR^5$, $C(O)N(R^5)(R^6)$, $SO_2N(R^5)(R^6)$, $NR^5SO_2R^7$, $C_{1-8}$ alkyl, $C_{3-8}$ cycloalkyl, and $C_{3-8}$ heterocyclyl. $R^1$ is preferably $C_{1-8}$ alkyl, $C_{3-8}$ cycloalkyl, or $C_{3-8}$ heterocyclyl. Examples include $C_{1-8}$ alkyl optionally substituted with $C_{1-8}$ alkoxyl, $C_{3-8}$ cycloalkyl, $C_{3-8}$ heterocyclyl, or heteroaryl.

One set of compounds of formula (I) have Ring A being phenyl substituted with one to three moieties selected from halogen, $OR^5$, $OCH_2Ar$, CN, $N(R^5)(R^6)$, $N(R^5)CO(R^7)$, $C(O)OR^5$, $C(O)N(R^5)(R^6)$, $SO_2N(R^5)(R^6)$, $NR^5SO_2R^7$, $C_{1-8}$ alkyl, $C_{3-8}$ cycloalkyl, and $C_{3-8}$ heterocyclyl; $R^1$ being $C_{1-8}$ alkyl optionally substituted with $C_{1-8}$ alkoxyl, $C_{3-8}$ cycloalkyl, $C_{3-8}$ heterocyclyl, or heteroaryl; L being O; and G being $N(R^9)(R^{10})$, in which $R^9$ and $R^{10}$, together with the atom to which they are attached, form $C_{3-8}$ heterocyclyl. Exemplary compounds include

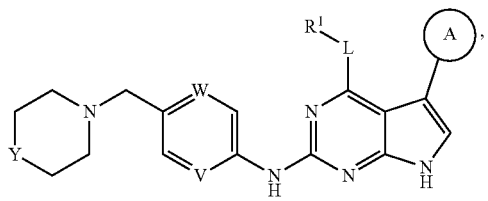

in which each of W and V, independently, is N or $CR^8$, $R^8$ being H, halogen, $OR^5$, $N(R^5)(R^6)$, or $C_{1-8}$ alkyl; Y is O, —NR, or —CR'R'', each of R, R', and R'', independently, being H, OH, $NH_2$, or $C_{1-8}$ alkyl; and the Y-containing heterocyclyl is optionally substituted with one or more $C_{1-8}$ alkyl.

Referring to variables $R^1$, Ring A, L, and G in formula (I), each of these variables can have a stereoisomeric configuration of R or S, and such compounds can have an enantiomeric excess of 90% or higher (e.g., ≥95% or ≥99%).

Also, within this invention is a pharmaceutical composition for treating cancer, e.g., solid tumor and hematological tumor, the composition containing one of the compounds of formula (I) set forth above or a tautomer, stereoisomer, isotopologue, or salt thereof and a pharmaceutically acceptable carrier.

Further covered by this invention is a method for treating an RTK-associated disease, the method including administering to a subject in need thereof an effective amount of a compound of formula (I) or a tautomer, stereoisomer, isotopologue, or salt thereof.

The RTK-associated disease treated by the method can be cancer or inflammation associated with an RTK kinase, e.g., Tyro3, Axl, and Mer. Provided below are more specific descriptions of these three kinases and their functions related to pathogenesis.

Tyro3, also known as Brt, Dtk, Etk-2, Rek, Rse, Sky, or Tif, is predominantly expressed in the brain and CNS. It is shown to be associated with tumorigenesis and tumor cell survival. Accordingly, Tyro3 is identified as a target for the development of therapeutic agents for treating Tyro3 over-expressing cancers (e.g., bladder cancer, melanoma, and breast cancer) or for enhancing the immune response.

Axl, also known as Ark, Tyro7, or Ufo, is expressed in normal tissues, particularly in bone marrow stroma, myeloid cells, and immune cells (e.g., dendritic cells, macrophages, and natural killer cells). It functions together with the type I interferon receptor to increase suppressor of cytokine signaling (SOCS) 1 and SOCS3 expression, which helps terminate inflammatory Toll-like receptor (TLR) signaling. Inhibition of Axl aids in restoring inflammatory TLR signaling. In particular, Axl has been implicated in metastasis in multiple tumor types. In patient samples and cell lines, Axl expression correlates with migration and metastasis. Canonical epithelial-mesenchymal transition (EMT)-inducing gene products TWIST, SNAIL, and SLUG are induced by Axl overexpression or through GAS6 stimulation. (See, e.g., Yu et al., Journal of Experimental & Clinical Cancer Research, 2010, 29:119). TWIST and SNAIL can also stimulate Axl expression, reinforcing EMT. Axl inhibition has been shown to reduce metastatic proliferation. Axl also plays a well-known role in resistance to targeted therapeutics. The broad range of cancer studies indicates that Axl inhibition can have widely applicable utility and re-sensitize tumors to targeted therapies.

Turning to Mer, also known as c-Eyk, Mertk, Nyk, or Tyro12, it is almost exclusively expressed in the monocyte cell lineage. Mer plays a significant role in efferocytosis, namely, the process by which apoptotic material is cleared by both monocyte-derived and epithelial cells. Mer functions in macrophages to promote the rapid clearance of self antigens, to repair injured tissue, and to suppress inflammation. In tumor-associated macrophages, Mer inhibition can lead to enhanced antitumor immunity.

An exemplary method covered by this invention is drawn to use of a compound of formula (I) or a tautomer, stereoisomer, isotopologue, or salt thereof for treating cancer associated with Tyro3, Axl, or Mer kinase.

Methods for synthesizing the compounds of formula (I) are well known in the art. See, for example, R. Larock, Comprehensive Organic Transformations ($2^{nd}$ Ed., VCH Publishers 1999); P. G. M. Wuts and T. W. Greene, Greene's Protective Groups in Organic Synthesis ($4^{th}$ Ed., John Wiley and Sons 2007); L. Fieser and M. Fieser, Fieser and Fieser's Reagents for Organic Synthesis (John Wiley and Sons 1994); L. Paquette, ed., Encyclopedia of Reagents for Organic Synthesis ($2^{nd}$ ed., John Wiley and Sons 2009); P. Roszkowski, J. K. Maurin, Z. Czarnocki "Enantioselective synthesis of (R)-(−)-praziquantel (PZQ)" Tetrahedron: Asymmetry 17 (2006) 1415-1419; and L. Hu, S. Magesh, L. Chen, T. Lewis, B. Munoz, L. Wang "Direct inhibitors of keap1-nrf2 interaction as antioxidant inflammation modulators," WO2013/067036.

The compounds of formula (I) thus prepared can be initially screened using in vitro assays, e.g., Axl kinase assay and Mer kinase assay, both described in EXAMPLE 2 below, for their potency in inhibiting RTK kinases. They can be subsequently evaluated using in vivo assays known in the field. The selected compounds can be further tested to verify their efficacy in both disease-related efficacy models and adverse effect models. Based on the results, an appropriate dosage range and administration route can be determined.

Without further elaboration, it is believed that one skilled in the art can, based on the above description, utilize the present invention to its fullest extent. The following specific examples, i.e., EXAMPLES 1-3, are therefore to be construed as merely illustrative, and not limitative of the scope of the invention. All publications cited herein are incorporated by reference in their entirety.

Among the specific examples, EXAMPLE 1 sets forth the procedures for preparing certain intermediates and 112 exemplary compounds of formula (I), as well as the analytical data for the compounds thus prepared; and EXAMPLES 2 and 3 set forth the protocols for testing these compounds.

Shown in Table 1 below are the structures and analytical data of 112 exemplary compounds of formula (I).

TABLE 1

| Cpd | Structure | Name | Mass |
|---|---|---|---|
| 1 | 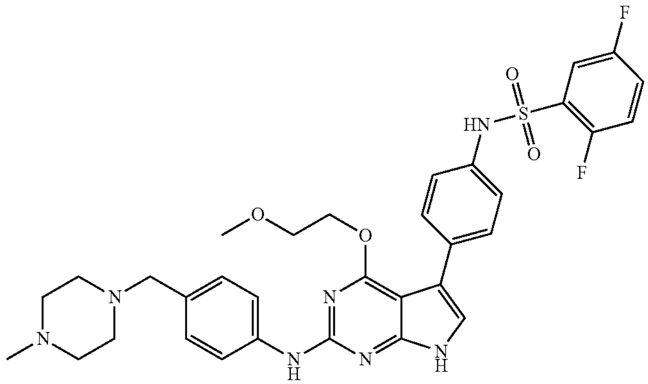 [SMILES: COCCOc1nc(Nc2ccc(CN3CCN(C)CC3)cc2)nc2[nH]cc(-c3ccc(NS(=O)(=O)c4cc(F)ccc4F)cc3)c12] | 2,5-difluoro-N-(4-(4-(2-methoxyethoxy)-2-((4-((4-methylpiperazin-1-yl)methyl)phenyl)amino)-7H-pyrrolo[2,3-d]pyrimidin-5-yl)phenyl)benzenesulfonamide | $^1$H NMR (500 MHz, MeOD): δ 7.69 (d, J = 8.5 Hz, 2H), 7.58 (d, J = 8.5 Hz, 2H), 7.54-7.57 (m, 1H), 7.30-7.37 (m, 2H), 7.20 (d, J = 8.5 Hz, 2H), 7.12 (d, J = 8.5 Hz, 2H), 6.98 (s, 1H), 4.54 (t, J = 4.5 Hz, 2H), 3.69 (t, J = 4.5 Hz, 2H), 3.47 (s, 2H), 3.34 (s, 3H), 2.50 (br, 8H), 2.28 (s, 3H); Mass (ESI): m/z 664.31 [M + H$^+$] |
| 2 | 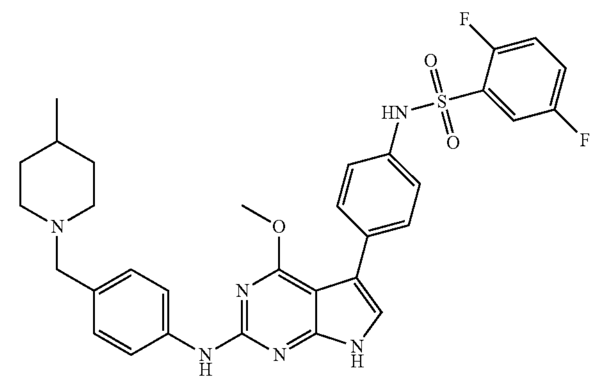 [SMILES: COc1nc(Nc2ccc(CN3CCC(C)CC3)cc2)nc2[nH]cc(-c3ccc(NS(=O)(=O)c4cc(F)ccc4F)cc3)c12] | 2,5-difluoro-N-(4-(4-methoxy-2-((4-((4-methylpiperidin-1-yl)methyl)phenyl)amino)-7H-pyrrolo[2,3-d]pyrimidin-5-yl)phenyl)benzenesulfonamide | $^1$H NMR (500 MHz, MeOD): δ 7.72 (d, J = 8.5 Hz, 2H), 7.54-7.57 (m, 1H), 7.49 (d, J = 8.5 Hz, 2H), 7.23-7.32 (m, 2H), 7.19 (d, J = 8.5 Hz, 2H), 7.11 (d, J = 8.5 Hz, 2H), 6.93 (s, 1H), 3.96 (s, 3H), 3.55 (s, 2H), 2.94 (d, J = 11.8 Hz, 2H), 2.13 (t, J = 11.4 Hz, 2H), 1.61 (d, J = 12.5 Hz, 2H), 1.34-1.37 (m, 1H), 1.18-1.26 (m, 2H), 0.88 (d, J = 6.4 Hz, 3H); Mass (ESI): m/z 619.66 [M + H$^+$] |
| 3 | 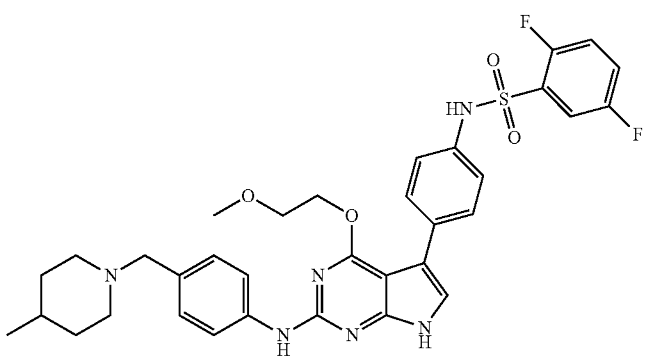 [SMILES: COCCOc1nc(Nc2ccc(CN3CCC(C)CC3)cc2)nc2[nH]cc(-c3ccc(NS(=O)(=O)c4cc(F)ccc4F)cc3)c12] | 2,5-difluoro-N-(4-(4-(2-methoxyethoxy)-2-((4-((4-methylpiperidin-1-yl)methyl)phenyl)amino)-7H-pyrrolo[2,3-d]pyrimidin-5-yl)phenyl)benzenesulfonamide | $^1$H NMR (500 MHz, MeOD): δ 7.65 (d, J = 8.5 Hz, 2H), 7.55-7.56 (m, 1H), 7.54 (d, J = 8.5 Hz, 2H), 7.22-7.29 (m, 2H), 7.14 (d, J = 8.5 Hz, 2H), 7.10 (d, J = 8.5 Hz, 2H), 6.90 (s, 1H), 4.48 (t, J = 4.5 Hz, 2H), 3.63 (t, J = 4.5 Hz, 2H), 3.43 (s, 3H), 2.85 (d, J = 11.6 Hz, 2H), 1.99 (dd, J = 10.8, 11.6 Hz, 2H), 1.54 (d, J = 12.4 Hz, 2H), 1.26-1.30 (m, 1H), 1.13-1.21 m, 2H), 0.84 (d, J = 6.4 Hz, 3H); Mass (ESI): m/z 663.34 [M + H$^+$] |
| 4 | 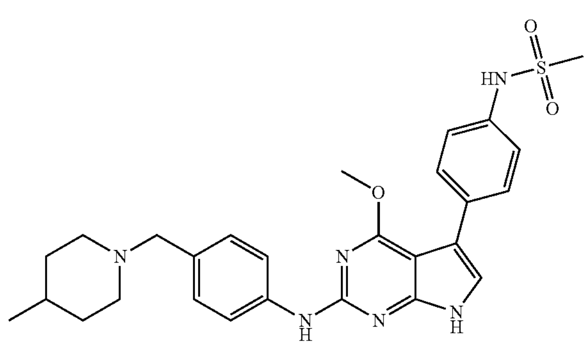 | N-(4-(4-methoxy-2-((4-((4-methylpiperidin-1-yl)methyl)phenyl)amino)-7H-pyrrolo[2,3-d]pyrimidin-5-yl)phenyl)methanesulfonamide | $^1$H NMR (500 MHz, MeOD): δ 7.75 (d, J = 8.5 Hz, 2H), 7.64 (d, J = 8.5 Hz, 2H), 7.22-7.25 (m, 4H), 7.04 (s, 1H), 4.06 (s, 3H), 3.48 (s, 2H), 2.97 (s, 3H), 2.91 (d, J = 11.5 Hz, 2H), 2.03 (t, J = 11.5 Hz, 2H), 1.64 (d, J = 12.3 Hz, 2H), 1.30-1.40 (m, 1H), 1.21-1.28 (m, 2H), 0.93 (d, J = 6.4 Hz, 3H); Mass (ESI): 521.86 [M + H$^+$] |

TABLE 1-continued

| Cpd | Structure | Name | Mass |
|---|---|---|---|
| 5 | 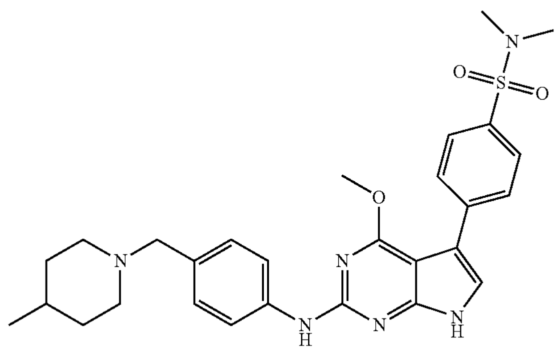 | 4-(4-methoxy-2-((4-((4-methylpiperidin-1-yl)methyl)phenyl)amino)-7H-pyrrolo[2,3-d]pyrimidin-5-yl)-N,N-dimethylbenzene-sulfonamide | ¹H NMR (500 MHz, MeOD): δ 7.82 (d, J = 8.4 Hz, 2H), 7.70 (d, J = 8.5 Hz, 2H), 7.67 (d, J = 8.4 Hz, 2H), 7.15 (d, J = 8.5 Hz, 2H), 7.12 (s, 1H), 3.99 (s, 3H), 3.39 (s, 2H), 2.83 (d, J = 11.4 Hz, 2H), 2.64 (s, 6H), 1.93 (t, J = 11.4 Hz, 2H), 1.54 (d, J = 11.9 Hz, 2H), 1.27-1.30 (m, 1H), 1.15-1.20 (m, 2H), 0.85 (d, J = 6.4 Hz, 3H); Mass (ESI): m/z 535.25 [M + H⁺] |
| 6 | 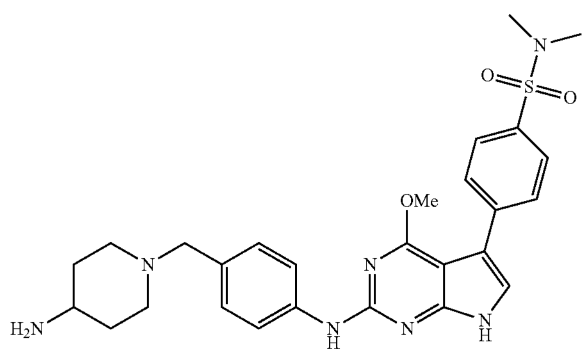 [SMILES: COc1nc(Nc2ccc(CN3CCC(N)CC3)cc2)nc2[nH]cc(-c3ccc(S(=O)(=O)N(C)C)cc3)c12] | 4-(2-((4-((4-aminopiperidin-1-yl)methyl)phenyl)amino)-4-methoxy-7H-pyrrolo[2,3-d]pyrimidin-5-yl)-N,N-dimethylbenzene-sulfonamide | ¹H NMR (500 MHz, DMSO) δ 11.94 (s, 1H), 9.54 (s, 1H), 8.05 (s, 2H), 7.97-7.96 (d, J = 8.3 Hz, 4H), 7.73-7.72 (d, J = 8.4 Hz, 2H), 7.55 (s, 1H), 7.38 2H), 4.21 (bs, 2H), 4.07 (s, 3H), 3.34 (bs, 2H), 3.01 (bs, 2H), 2.64 (s, 6H), 2.09 (bs, 2H), 1.72 (m, 2H); Mass (ESI): m/z 535.97 [M + H⁺] |
| 7 | 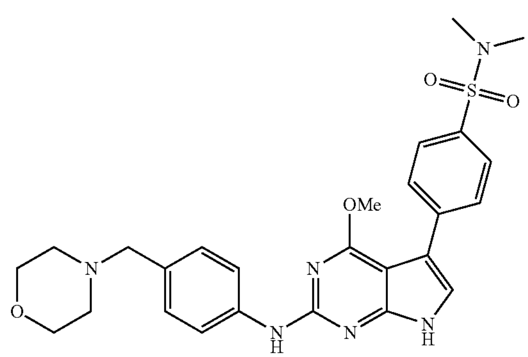 [SMILES: COc1nc(Nc2ccc(CN3CCOCC3)cc2)nc2[nH]cc(-c3ccc(S(=O)(=O)N(C)C)cc3)c12] | 4-(4-methoxy-2-((4-(morpholinomethyl)phenyl)amino)-7H-pyrrolo[2,3-d]pyrimidin-5-yl)-N,N-dimethylbenzene-sulfonamide | ¹H NMR (500 MHz, DMSO) δ 11.94 (s, 1H), 9.54 (s, 1H), 7.97-7.95 (m, 4H), 7.73-7.72 (d, J = 8.5 Hz, 2H), 7.55-7.54 (d, J = 2.5 Hz, 1H), 7.4-7.39 (d, J = 8.5 Hz, 2H), 4.27 (bs, 2H), 4.07 (s, 3H), 3.99-3.96 (d, 12.6 Hz, 2H), 3.65-3.6 (t, J = 12.1 Hz, 2H), 3.13 (bs, 2H), 2.65 (s, 6H); Mass (ESI): m/z 523.43 [M + H⁺] |
| 8 | 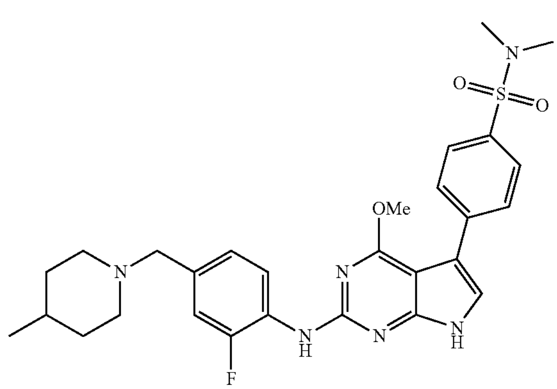 | 4-(2-((2-fluoro-4-((4-methylpiperidin-1-yl)methyl)phenyl)amino)-4-methoxy-7H-pyrrolo[2,3-d]pyrimidin-5-yl)-N,N-dimethylbenzene-sulfonamide | ¹H NMR (500 MHz, DMSO) δ 11.9 (s, 1H), 9.17 (s, 1H), 8.84 (s, 1H), 8.23 (s, 1H), 7.95 (d, J = 8.4 Hz, 1H), 7.71 (d, J = 8.5 Hz, 2H), 7.53 (s, 1H), 7.40 (s, 1H), 7.28 (s, 1H), 4.25 (s, 2H), 4.02 (s, 3H), 3.3 (m, 2H), 2.9 (s, 2H), 2.64 (s, 6H), 1.80 (m, 2H), 1.6 (bs, 1H), 1.26 (m, 2H), 0.91 (d, J = 6.4 Hz, 2H); Mass (ESI): m/z 553.2 [M + H⁺] |

TABLE 1-continued

| Cpd | Structure | Name | Mass |
|---|---|---|---|
| 9 | 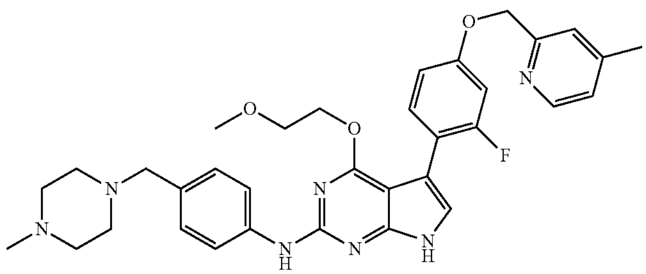 | 5-(2-fluoro-4-((4-methylpyridin-2-yl)methoxy)phenyl)-4-(2-methoxyethoxy)-N-(4-((4-methylpiperazin-1-yl)methyl)phenyl)-7H-pyrrolo[2,3-d]pyrimidin-2-amine | $^1$H NMR (600 MHz, MeOD): δ (ppm) 8.39 (d, J = 5.1 Hz, 1H), 7.72 (d, J = 8.5 Hz, 2H), 7.61 (dd, J = 8.0, 9.4 Hz, 1H), 7.45 (s, 1H), 7.21-7.24 (m, 3H), 7.00 (d, J = 1.8 Hz, 1H), 6.80-6.84 (m, 2H), 5.16 (s, 2H), 4.54 (dd, J = 4.5, 4.8 Hz, 2H), 3.67 (dd, J = 4.5, 4.8 Hz, 2H), 3.48 (s, 2H), 3.29 (s, 3H), 2.50 (br, 8H), 2.40 (s, 3H), 2.28 (s, 3H); Mass (ESI): m/z 612.66 [M + H$^+$] |
| 10 | 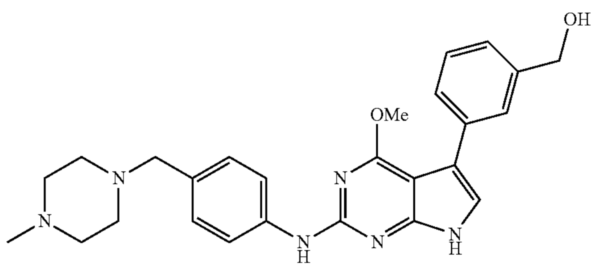 [SMILES: COc1nc(Nc2ccc(CN3CCN(C)CC3)cc2)nc2[nH]cc(-c3cccc(CO)c3)c12] | (3-(4-methoxy-2-((4-((4-methylpiperazin-1-yl)methyl)phenyl)amino)-7H-pyrrolo[2,3-d]pyrimidin-5-yl)phenyl)methanol | $^1$H NMR (500 MHz, MeOD) δ 7.83 (d, J = 8.3 Hz, 2H), 7.67 (s, 1H), 7.56 (d, J = 9.3 Hz, 1H), 7.34-7.23 (m, 4H), 7.08 (s, 1H), 4.65 (s, 2H), 4.06 (s, 3H), 3.79 (s, 2H), 3.6 (s, 2H), 3.35-3.17 (m, 8H), 2.77 (s, 3H); Mass (ESI): m/z 458.71 [M + H$^+$] |
| 11 | 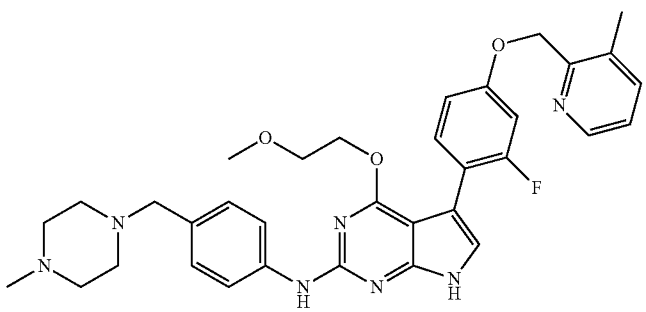 [SMILES: COCCOc1nc(Nc2ccc(CN3CCN(C)CC3)cc2)nc2[nH]cc(-c3ccc(OCc4ncccc4C)cc3F)c12] | 5-(2-fluoro-4-((3-methylpyridin-2-yl)methoxy)phenyl)-4-(2-methoxyethoxy)-N-(4-((4-methylpiperazin-1-yl)methyl)phenyl)-7H-pyrrolo[2,3-d]pyrimidin-2-amine | $^1$H NMR (600 MHz, MeOD): δ (ppm) 8.36 (dd, J = 1.2, 4.9 Hz, 1H), 7.71 (d, J = 8.8 Hz, 2H), 7.67 (d, J = 7.6 Hz, 1H), 7.58 (dd, J = 8.5, 9.1 Hz, 1H), 7.31 (dd, J = 5.2, 7.9 Hz, 1H), 7.20 (d, J = 8.5 Hz, 2H), 6.98 (d, J = 1.8 Hz, 1H), 6.81-6.84 (m, 2H), 5.20 (s, 2H), 4.52 (dd, J = 4.5, 4.8 Hz, 2H), 3.66 (dd, J = 4.5, 4.8 Hz, 2H), 3.45 (s, 2H), 3.28 (s, 3H), 2.51 (br, 8H), 2.42 (s, 3H), 2.25 (s, 3H); Mass (ESI): m/z 612.55 [M + H$^+$] |
| 12 | 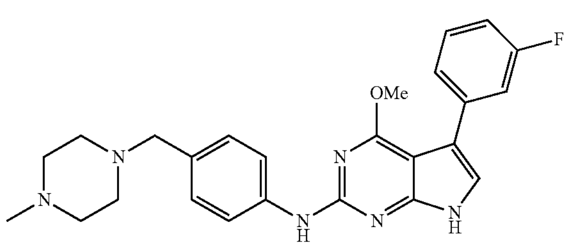 [SMILES: COc1nc(Nc2ccc(CN3CCN(C)CC3)cc2)nc2[nH]cc(-c3cccc(F)c3)c12] | 5-(3-fluorophenyl)-4-methoxy-N-(4-((4-methylpiperazin-1-yl)methyl)phenyl)-7H-pyrrolo[2,3-d]pyrimidin-2-amine | $^1$H NMR (500 MHz, MeOD) δ 7.83 (bs, 2H), 7.47-7.42 (m, 2H), 7.36-7.3 (m, 3H), 7.14 (s, 1H), 6.95 (t, J = 8.4 Hz, 1H), 4.08 (s, 3H), 3.6 (s, 2H), 3.2-2.83 (m, 8H), 2.16 (s, 3H); Mass (ESI): m/z 447.97 [M + H$^+$] |
| 13 | 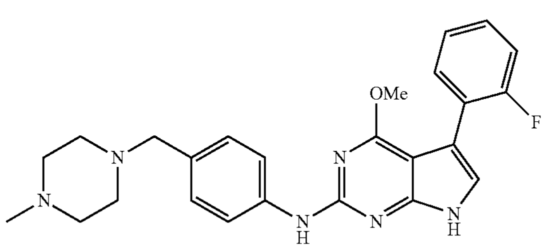 [SMILES: COc1nc(Nc2ccc(CN3CCN(C)CC3)cc2)nc2[nH]cc(-c3ccccc3F)c12] | 5-(2-fluorophenyl)-4-methoxy-N-(4-((4-methylpiperazin-1-yl)methyl)phenyl)-7H-pyrrolo[2,3-d]pyrimidin-2-amine | $^1$H NMR (500 MHz, MeOD) δ 7.82 (bs, 2H), 7.6-7.58 (m, 1H), 7.18-7.07 (m, 6H), 4.00 (s, 3H), 3.59 (s, 2H), 3.1-2.8 (m, 8H), 2.4 (s, 3H); Mass (ESI): m/z 463.78 [M + H$^+$] |

TABLE 1-continued

| Cpd | Structure | Name | Mass |
|---|---|---|---|
| 14 | 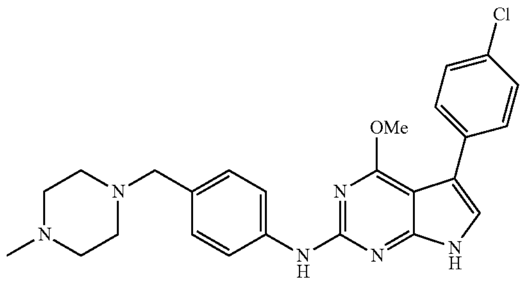 [SMILES: COc1nc(Nc2ccc(CN3CCN(C)CC3)cc2)nc2[nH]cc(-c3ccc(Cl)cc3)c12] | 5-(4-chlorophenyl)-4-methoxy-N-(4-((4-methylpiperazin-1-yl)methyl)phenyl)-7H-pyrrolo[2,3-d]pyrimidin-2-amine | $^1$H NMR (500 MHz, MeOD) δ 7.76 (d, J = 8.5 Hz, 2H), 7.63 (d, J = 8.5 Hz, 2H), 7.33 (d, J = 8.5 Hz, 2H), 7.24 (d, J = 8.4 Hz, 2H), 7.08 (s, 1H), 4.06 (s, 3H), 3.5 (s, 2H), 3.0-2.6 (m, 8H), 2.29 (s, 3H); Mass (ESI): m/z 462.98 [M + H$^+$] |
| 15 | 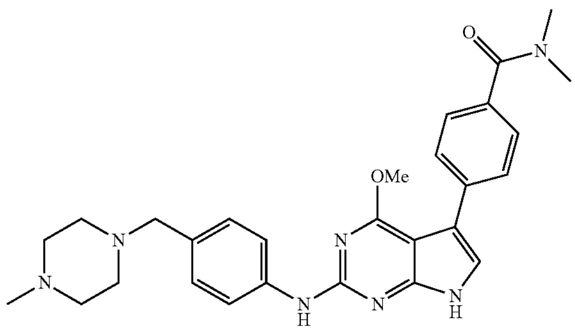 | 4-(4-methoxy-2-((4-((4-methylpiperazin-1-yl)methyl)phenyl)amino)-7H-pyrrolo[2,3-d]pyrimidin-5-yl)-N,N-dimethylbenzamide | $^1$H NMR (500 MHz, MeOD) δ 7.83 (d, J = 8.3 Hz, 2H), 7.77 (d, J = 8.1 Hz, 2H), 7.44 (d, J = 8.2 Hz, 2H), 7.29 (d, J = 8.3 Hz, 2H), 7.17 (s, 1H), 4.07 (s, 3H), 3.77 (s, 2H), 3.13-3.1 (m, 8H), 2.77 (s, 3H); Mass (ESI): m/z 400.4 [M + H$^+$] |
| 16 | 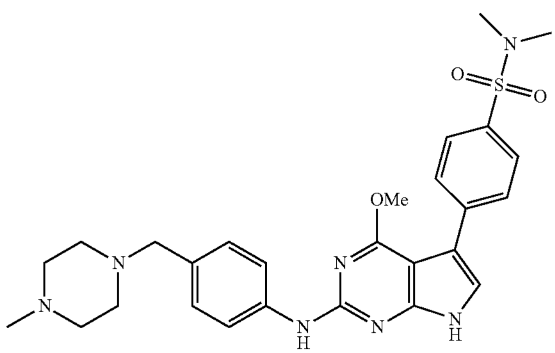 | 4-(4-methoxy-2-((4-((4-methylpiperazin-1-yl)methyl)phenyl)amino)-7H-pyrrolo[2,3-d]pyrimidin-5-yl)-N,N-dimethylbenzene-sulfonamide | $^1$H NMR (500 MHz, CDCl$_3$) δ ppm 2.13 (s, 3H), 2.32 (s, 8H), 2.64 (s, 6H), 4.05 (s, 3H), 7.16 (d, J = 8.3 Hz, 2H), 7.48 (s, 1H), 7.71 (d, J = 8.3 Hz, 2H), 7.78 (d, J = 8.3 Hz, 2H), 7.96 (d, J = 8.3 Hz, 2H), 9.23 (s, 1H), 11.87 (s, 1H); Mass (ESI): m/z 536.29 [M + H$^+$] |
| 17 | 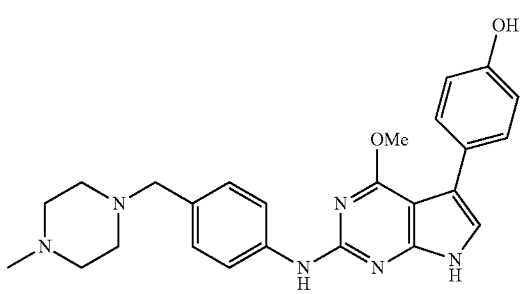 [SMILES: COc1nc(Nc2ccc(CN3CCN(C)CC3)cc2)nc2[nH]cc(-c3ccc(O)cc3)c12] | 4-(4-methoxy-2-((4-((4-methylpiperazin-1-yl)methyl)phenyl)amino)-7H-pyrrolo[2,3-d]pyrimidin-5-yl)phenol | $^1$H NMR (500 MHz, CDCl$_3$) δ ppm 2.26 (s, 3H), 2.32 (s, 8H), 3.47 (s, 2H), 4.02 (s, 3H), 6.77 (d, J = 2.1 Hz, 2H), 6.89 (s, 1H), 7.20-7.24 (m, 2H), 7.44-7.46 (m, 2H), 7.72-7.78 (m, 2H); Mass (ESI): m/z 445.48 [M + H$^+$] |
| 18 | 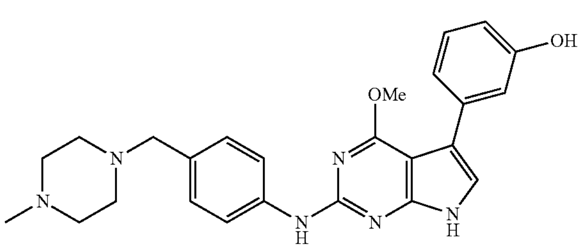 [SMILES: COc1nc(Nc2ccc(CN3CCN(C)CC3)cc2)nc2[nH]cc(-c3cccc(O)c3)c12] | 3-(4-methoxy-2-((4-((4-methylpiperazin-1-yl)methyl)phenyl)amino)-7H-pyrrolo[2,3-d]pyrimidin-5-yl)phenol | $^1$H NMR (500 MHz, CDCl$_3$) δ ppm 2.28 (s, 3H), 2.49 (s, 8H), 3.50 (s, 2H), 4.06 (s, 3H), 6.77 (d, J = 7.8 Hz, 2H), 7.01 (s, 1H), 7.12-7.16 (m, 3H), 7.24 (d, J = 8.4 Hz, 2H), 7.72-7.78 (d, J = 8.4 Hz, 2H); Mass (ESI): m/z 445.43 [M + H$^+$] |

TABLE 1-continued

| Cpd | Structure | Name | Mass |
|---|---|---|---|
| 19 | 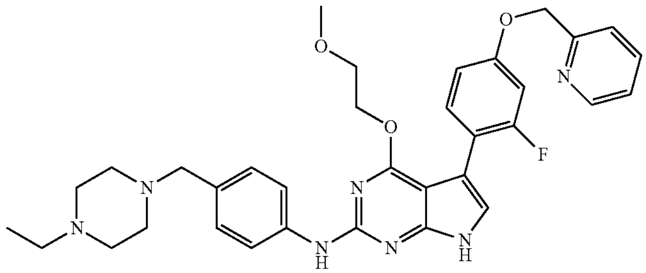 [SMILES: CCN1CCN(Cc2ccc(Nc3nc(OCCOC)c4c(-c5ccc(OCc6ccccn6)cc5F)c[nH]c4n3)cc2)CC1] | N-(4-((4-ethylpiperazin-1-yl)methyl)phenyl)-5-(2-fluoro-4-(pyridin-2-ylmethoxy)phenyl)-4-(2-methoxyethoxy)-7H-pyrrolo[2,3-d]pyrimidin-2-amine | 1H NMR (600 MHz, MeOD) δ 8.63 (d, J = 4.5 Hz, 1H), 8.02 (ddd, J = 7.8, 6.3, 1.7 Hz, 1H), 7.83 (d, J = 8.6 Hz, 2H), 7.73 (d, J = 7.9 Hz, 1H), 7.65 (dd, J = 12.5, 5.0 Hz, 1H), 7.54-7.46 (m, 1H), 7.33 (d, J = 8.6 Hz, 2H), 7.06 (d, J = 1.9 Hz, 1H), 6.89 (d, J = 2.4 Hz, 1H), 6.87 (dd, J = 4.4, 1.9 Hz, 1H), 5.29 (s, 2H), 4.61-4.53 (m, 2H), 3.87 (s, 2H), 3.75-3.65 (m, 2H), 3.37 (s, 1H), 3.26 (s, 2H), 3.14 (q, J = 7.3 Hz, 3H), 3.02 (s, 4H), 1.33 (t, J = 7.3 Hz, 3H). Mass (ESI): m/z 612.48 [M + H$^+$] |
| 20 | 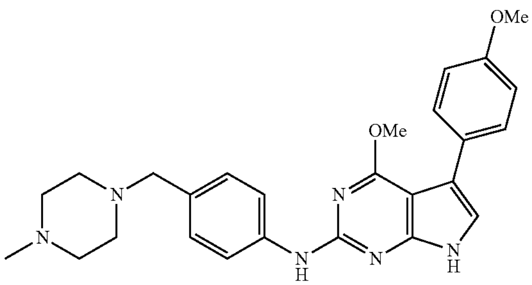 [SMILES: COc1ccc(-c2c[nH]c3nc(Nc4ccc(CN5CCN(C)CC5)cc4)nc(OC)c23)cc1] | 4-methoxy-5-(4-methoxyphenyl)-N-(4-((4-methyl piperazin-1-yl) methyl)phenyl)-7H-pyrrolo[2,3-d] pyrimidin-2-amine | $^1$H NMR (500 MHz, CDCl$_3$) δ ppm 2.28 (s, 3H), 2.51 (s, 8H), 3.49 (s, 2H), 3.79 (s, 3H), 3.95 (s, 3H), 5.49 (s, 1H), 6.89-6.93 (m, 3H), 7.21-7.24 (m, 2H), 7.53-7.55 (m, 2H), 7.77-7.78 (m, 2H); Mass (ESI): m/z 459.4 [M + H$^+$] |
| 21 | 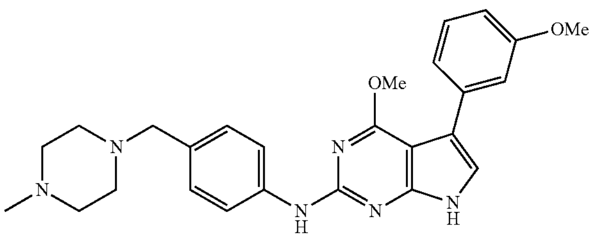 [SMILES: COc1cccc(-c2c[nH]c3nc(Nc4ccc(CN5CCN(C)CC5)cc4)nc(OC)c23)c1] | 4-methoxy-5-(3-methoxyphenyl)-N-(4-((4-methyl piperazin-1-yl) methyl)phenyl)-7H-pyrrolo[2,3-d] pyrimidin-2-amine | $^1$H NMR (500 MHz, CDCl$_3$) δ ppm 2.28 (s, 3H), 2.51 (s, 8H), 3.49 (s, 2H), 3.79 (s, 3H), 3.95 (s, 3H), 5.49 (s, 1H), 6.77-6.79 (m, 1H), 7.04 (s, 1H), 7.19-7.24 (m, 4H), 7.28 (s, 1H), 7.74 (d, J = 8.36 Hz, 2H); Mass (ESI): m/z 459.08 [M + H$^+$] |
| 22 | 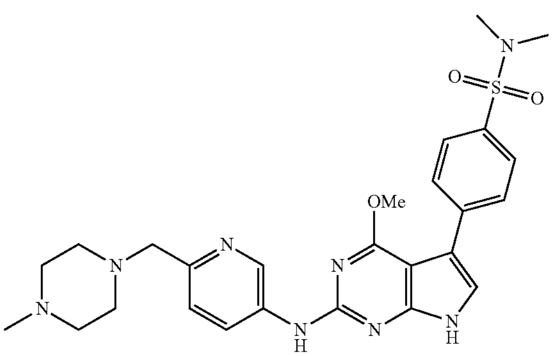 | 4-(4-methoxy-2-((6-((4-methylpiperazin-1-yl)methyl)pyridin-3-yl)amino)-7H-pyrrolo[2,3-d]pyrimidin-5-yl)-N,N-dimethylbenzenesulfonamide | $^1$H NMR (500 MHz, CDCl$_3$) δ ppm 2.28 (s, 3H), 2.57 (s, 8H), 2.71 (s, 6H), 3.62 (s, 2H), 4.05 (s, 3H), 7.29 (s, 1H), 7.40 (d, J = 8.3 Hz, 2H), 7.74 (d, J = 8.3 Hz, 2H), 7.91 (d, J = 8.3 Hz, 2H), 8.31 (d, J = 6.0 Hz, 1H), 8.94 (d, J = 6.0 Hz, 1H); Mass (ESI): m/z 537.27 [M + H$^+$] |
| 23 | 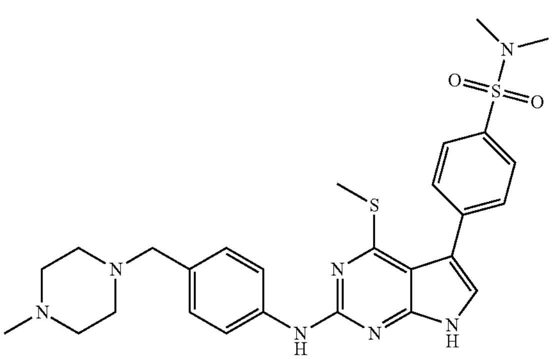 | N,N-dimethyl-4-(2-((4-((4-methylpiperazin-1-yl)methyl)phenyl)amino)-4-(methylthio)-7H-pyrrolo[2,3-d]pyrimidin-5-yl)benzenesulfonamide | $^1$NMR (500 MHz, DMSO-d6): δ 11.88 (s, 1H), 9.24 (s, 1H), 7.96 (d, J = 8.4 Hz, 2H), 7.78 (d, J = 8.4 Hz, 2H), 7.71 (d, J = 8.4 Hz, 2H), 7.48 (s, 1H), 7.17 (d, J = 8.4 Hz, 2H), 4.05 (s, 3H), 3.36 (s, 2H), 2.64 (s, 6H), 2.32 (br, 8H), 2.13 (s, 3H); Mass (ESI): m/z 552.51 [M + H$^+$] |

TABLE 1-continued

| Cpd | Structure | Name | Mass |
|---|---|---|---|
| 24 | 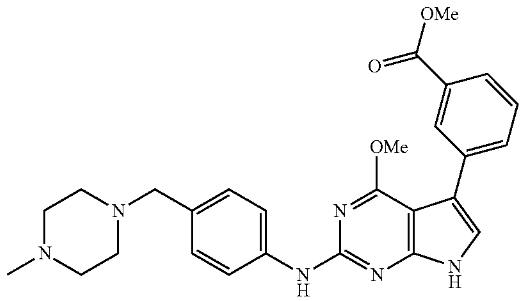 [SMILES: COC(=O)c1cccc(-c2c[nH]c3nc(Nc4ccc(CN5CCN(C)CC5)cc4)nc(OC)c23)c1] | methyl 3-(4-methoxy-2-((4-((4-methylpiperazin-1-yl)methyl)phenyl)amino)-7H-pyrrolo[2,3-d]pyrimidin-5-yl)Benzoate | $^1$H NMR (500 MHz, MeOD) δ ppm 2.28 (s, 3H), 2.51 (br, 8H), 3.50 (s, 2H), 3.93 (s, 3H), 4.07 (s, 3H), 4.73 (s, 2H), 7.14 (s, 1H), 7.24 (d, J = 8.23 Hz, 2H), 7.44-7.47 (m, 1H), 7.76 (d, J = 8.27 Hz, 2H), 7.86-7.90 (m, 1H), 8.39 (s, 1H); Mass (ESI): m/z 487.14 [M + H$^+$] |
| 25 | 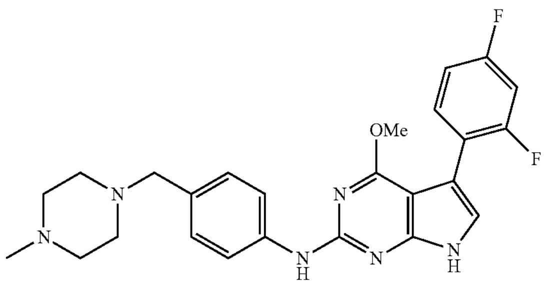 [SMILES: COc1nc(Nc2ccc(CN3CCN(C)CC3)cc2)nc2[nH]cc(-c3ccc(F)cc3F)c12] | 5-(2,4-difluorophenyl)-4-methoxy-N-(4-((4-methylpiperazin-1-yl)methyl)phenyl)-7H-pyrrolo[2,3-d]pyrimidin-2-amine | $^1$H NMR (500 MHz, CDCl$_3$) δ ppm 2.28 (s, 3H), 2.51 (br, 8H), 3.50 (s, 2H), 3.96 (s, 3H), 4.83 (s, 2H), 6.94-6.98 (m, 2H), 7.24 (d, J = 8.4 Hz, 2H), 7.59-7.60 (m, 1H), 7.75 (d, J = 8.4 Hz, 2H); Mass (ESI): m/z 465.23 [M + H$^+$] |
| 26 | 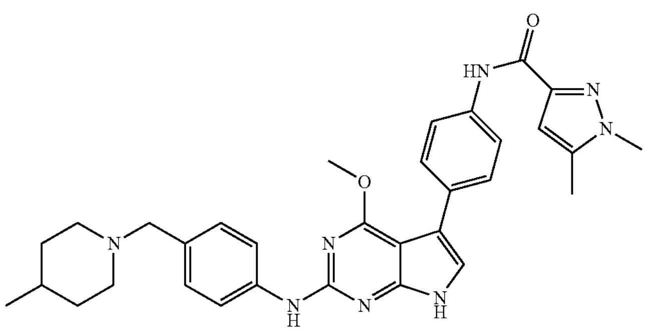 | N-(4-(4-methoxy-2-((4-((4-methylpiperidin-1-yl)methyl)phenyl)amino)-7H-pyrrolo[2,3-d]pyrimidin-5-yl)phenyl)-1,5-dimethyl-7H-pyrazole-3-carboxamide | $^1$H NMR (500 MHz, MeOD): δ 7.70 (d, J = 8.5 Hz, 2H), 7.63 (d, J = 8.5 Hz, 2H), 7.60 (d, J = 8.5 Hz, 2H), 7.17 (d, J = 8.5 Hz, 2H), 6.97 (s, 1H), 6.55 (s, 1H), 4.00 (s, 3H), 3.79 (s, 3H), 3.40 (s, 2H), 2.84 (d, J = 11.5 Hz, 2H), 2.27 (s, 3H), 1.97 (t, J = 11.5 Hz, 2H), 1.56 (d, J = 11.5 Hz, 2H), 1.27-1.31 (m, 1H), 1.15-1.22 (m, 2H), 0.87 (d, J = 6.4 Hz, 3H); Mass (ESI): m/z 565.27 [M + H$^+$] |
| 27 | 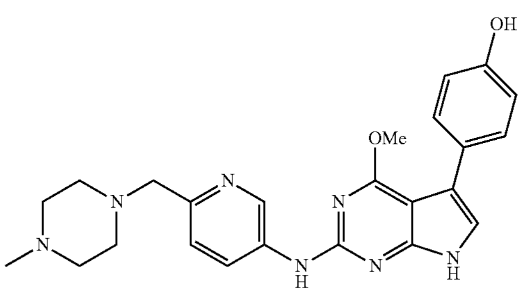 | 4-(4-methoxy-2-((6-((4-methylpiperazin-1-yl)methyl)pyridin-3-yl)amino)-7H-pyrrolo[2,3-d]pyrimidin-5-yl)phenol | $^1$H NMR (500 MHz, CDCl$_3$) δ ppm 2.28 (s, 3H), 2.55 (br, 8H), 3.63 (s, 2H), 4.05 (s, 3H), 6.78 (d, J = 8.5 Hz, 2H), 6.96 (s, 1H), 7.41 (d, J = 8.5 Hz, 1H), 7.45 (d, J = 8.5 Hz, 2H), 8.33 (d, J = 8.5 Hz, 1H), 8.94 (s, 1H); Mass (ESI): m/z 446.4 [M + H$^+$] |
| 28 | 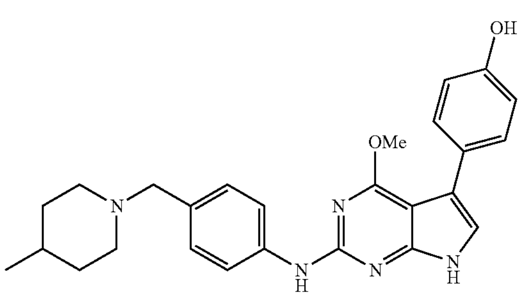 [SMILES: COc1nc(Nc2ccc(CN3CCC(C)CC3)cc2)nc2[nH]cc(-c3ccc(O)cc3)c12] | 4-(4-methoxy-2-((4-((4-methylpiperidin-1-yl)methyl)phenyl)amino)-7H-pyrrolo[2,3-d]pyrimidin-5-yl)phenol | $^1$H NMR (500 MHz, CDCl$_3$) δ ppm 0.90 (s, 3H), 1.19-1.27 (m, 2H), 1.35-1.37 (m, 1H), 1.61 (d, J = 12.4 Hz, 2H), 1.97-2.02 (m, 2H), 2.88 (d, J = 12.0 Hz, 2H), 3.45 (s, 2H), 4.03 (s, 3H), 6.78 (d, J = 8.5 Hz, 2H), 6.90 (s, 1H), 7.21 (d, J = 8.5 Hz, 1H), 7.45 (d, J = 8.5 Hz, 2H), 7.73 (d, J = 8.5 Hz, 2H); Mass (ESI): m/z 444.10 [M + H$^+$] |

TABLE 1-continued

| Cpd | Structure | Name | Mass |
|---|---|---|---|
| 29 | 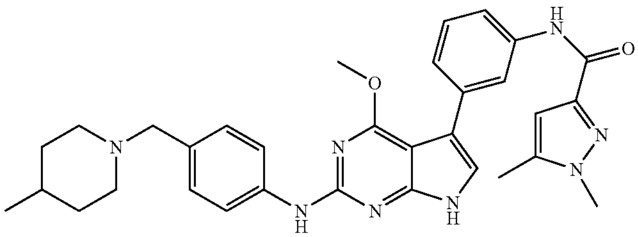 | N-(3-(4-methoxy-2-((4-((4-methyl piperidin-1-yl)methyl) phenyl)amino)-7H-pyrrolo[2,3-d] pyrimidin-5-yl) phenyl)-1,5-dimethyl-1H-pyrazole-3-carboxamide | $^1$H NMR (500 MHz, CDCl$_3$) δ 0.91 (s, 3H), 1.19-1.27 (m, 2H), 1.37 (m, 1H), 1.63 (d, 12.4 Hz, 2H), 1.98-2.03 (m, 2H), 2.90 (d, J = 12.4 Hz, 2H), 3.46 (s, 2H), 3.99 (s, 3H), 6.93-6.96 (m, 2H), 6.97 (s, 1H), 7.22 (d, J = 8.45 Hz, 2H), 7.56-7.61 (m, 1H), 7.74 (d, J = 8.4 Hz, 2H); Mass (ESI): m/z 464.47 [M + H$^+$] |
| 30 | 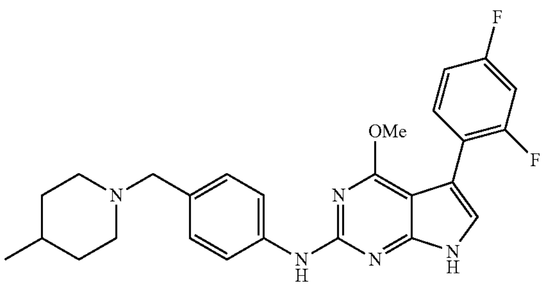 | 5-(2,4-difluorophenyl)-4-methoxy-N-(4-((4-methyl piperidin-1-yl) methyl)phenyl)-7H-pyrrolo[2,3-d]pyrimidin-2-amine | $^1$H NMR (500 MHz, DMSO) δ 11.5 (s, 1H), 9.11 (s, 1H), 7.77 (d, J = 8.5 Hz, 2H), 7.25-7.04 (m, 7H), 6.92 (d, J = 2.2 Hz, 1H), 3.87 (s, 3H), 3.44 (s, 2H), 2.76 (d, J = 11 Hz, 2H), 2.22 (s, 3H), 1.86 (m, 2H), 1.55 (d, J = 12.5 Hz, 2H), 1.3 (m, 1H), 1.11 (d, J = 9.2 Hz, 2H), 0.88 (d, J = 6.5 Hz, 3H); Mass (ESI): m/z 442.2 [M + H$^+$] |
| 31 | 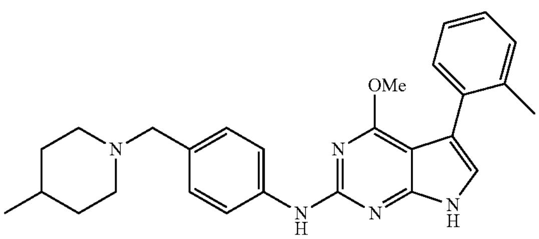 | 4-methoxy-N-(4-((4-methylpiperidin-1-yl)methyl)phenyl)-5-(o-tolyl)-7H-pyrrolo[2,3-d]pyrimidin-2-amine | $^1$H NMR (500 MHz, DMSO) δ 11.5 (s, 1H), 9.11 (s, 1H), 7.77 (d, J = 8.5 Hz, 2H), 7.25-7.04 (m, 7H), 6.92 (d, J = 2.2 Hz, 1H), 3.87 (s, 3H), 3.44 (s, 2H), 2.76 (d, J = 11 Hz, 2H), 2.22 (s, 3H), 1.86 (m, 2H), 1.55 (d, J = 12.5 Hz, 2H), 1.3 (m, 1H), 1.11 (d, J = 9.2 Hz, 2H), 0.88 (d, J = 6.5 Hz, 3H); Mass (ESI): m/z 442.2 [M + H$^+$] |
| 32 | 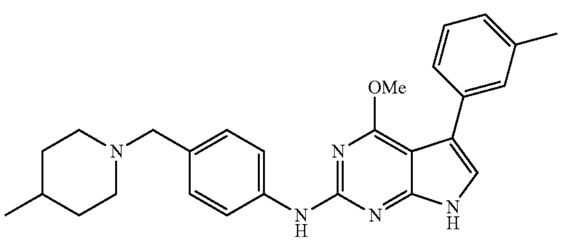 | 4-methoxy-N-(4-((4-methylpiperidin-1-yl)methyl)phenyl)-5-(m-tolyl)-7H-pyrrolo[2,3-d]pyrimidin-2-amine | $^1$H NMR (500 MHz, DMSO) δ 11.6 (s, 1H), 9.13 (s, 1H), 7.77 (d, J = 8.4 Hz, 1H), 7.47-7.43 (m, 1H), 7.24 (t, J = 7.7 Hz, 1H), 7.19-7.15 (m, 1H), 7.03 (d, J = 1.1 Hz, 1H), 4.0 (s, 3H), 3.54 (s, 2H), 2.76 (m, 2H), 2.36 (s, 3H), 1.9 (m, 2H), 1.54 (m, 2H), 1.23 (m, 1H), 1.11 (m, 2H), 0.88 (d, J = 6.5 Hz, 3H); Mass (ESI): m/z 442.21 [M + H$^+$] |
| 33 | 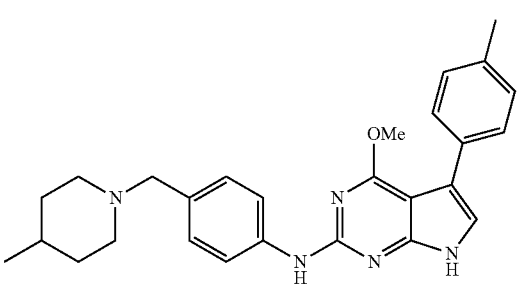 [SMILES: COc1nc(Nc2ccc(CN3CCC(C)CC3)cc2)nc2[nH]cc(-c3ccc(C)cc3)c12] | 4-methoxy-N-(4-((4-methylpiperidin-1-yl)methyl)phenyl)-5-(p-tolyl)-7H-pyrrolo[2,3-d]pyrimidin-2-amine | $^1$H NMR (500 MHz, DMSO) δ 11.5 (s, 1H), 9.08 (s, 1H), 7.73 (d, J = 8.5 Hz, 2H), 7.49 (d, J = 8.1 Hz, 2H), 7.14-7.11 (m, 5H), 3.96 (s, 3H), 3.39 (s, 2H), 2.72 (d, J = 11 Hz, 2H), 2.28 (s, 3H), 1.82 (m, 2H), 1.51 (d, J = 12 Hz, 2H), 1.3 (m, 1H), 1.1 (m, 2H), 0.84 (d, J = 6.5 Hz, 3H); Mass (ESI): m/z 442.16 [M + H$^+$] |

TABLE 1-continued

| Cpd | Structure | Name | Mass |
|---|---|---|---|
| 34 | 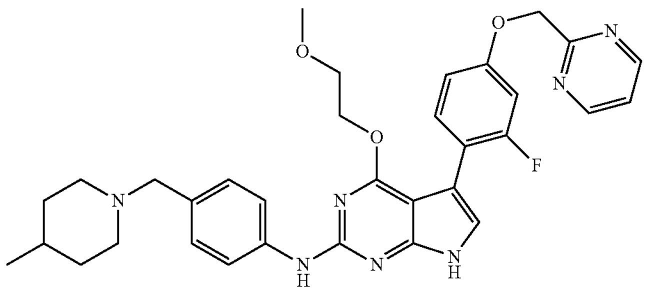 [SMILES: COCCOc1nc(Nc2ccc(CN3CCC(C)CC3)cc2)nc2[nH]cc(-c3ccc(OCc4ncccn4)cc3F)c12] | 5-(2-fluoro-4-(pyrimidin-2-ylmethoxy)phenyl)-4-(2-methoxyethoxy)-N-(4-((4-methylpiperidin-1-yl)methyl)phenyl)-7H-pyrrolo[2,3-d]pyrimidin-2-amine | $^1$H NMR (600 MHz, CDCl$_3$): δ (ppm) 9.84 (s, 1H), 8.80 (d, J = 4.8 Hz, 2H), 7.60 (t, J = 8.6 Hz, 1H), 7.55 (d, J = 8.6 Hz, 2H), 7.26 (t, J = 5.0 Hz, 1H), 7.23 (d, J = 8.5 Hz, 2H), 6.98 (s, 1H), 6.77-6.83 (m, 2H), 6.73 (s, 1H), 5.32 (s, 2H), 4.54 (dd, J = 4.6, 5.0 Hz, 2H), 3.66 (dd, J = 4.6, 5.0 Hz, 2H), 3.43 (s, 2H), 3.32 (s, 3H), 2.84 (d, J = 11.6 Hz, 2H), 1.89 (td, J = 11.6, 1.5 Hz, 2H), 1.54 (d, J = 11.6 Hz, 2H), 1.27-1.33 (m, 1H), 1.21 (dq, J = 3.5, 12.4 Hz, 2H), 0.88 (d, J = 6.6 Hz, 3H); Mass (ESI): m/z 598.39 [M + H$^+$] |
| 35 | 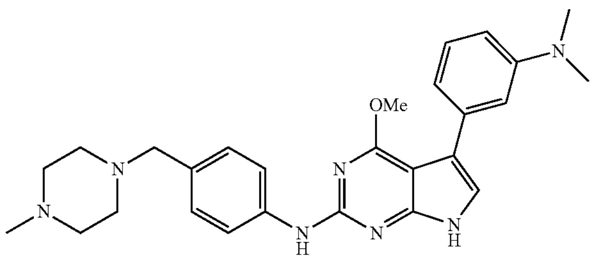 | 5-(3-(dimethylamino)phenyl)-4-methoxy-N-(4-((4-methylpiperazin-1-yl)methyl)phenyl)-7H-pyrrolo[2,3-d]pyrimidin-2-amine | $^1$H NMR (500 MHz, DMSO) δ 11.6 (s, 1H), 9.13 (s, 1H), 7.78 (d, J = 8.5 Hz, 2H), 7.19-7.12 (m, 5H), 6.93 (d, J = 7.6 Hz, 1H), 6.62-6.59 (m, 1H), 4.01 (s, 3H), 3.47 (s, 2H), 2.93 (s, 6H), 2.34 (m, 8H), 2.14 (s, 3H); Mass (ESI): m/z 472.24 [M + H$^+$] |
| 36 | 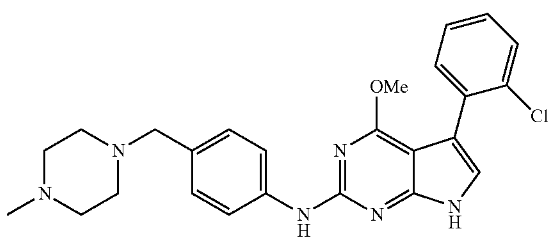 [SMILES: COc1nc(Nc2ccc(CN3CCN(C)CC3)cc2)nc2[nH]cc(-c3ccccc3Cl)c12] | 5-(2-chlorophenyl)-4-methoxy-N-(4-((4-methylpiperazin-1-yl)methyl)phenyl)-7H-pyrrolo[2,3-d]pyrimidin-2-amine | $^1$H NMR (500 MHz, DMSO) δ 11.6 (s, 1H), 9.14 (s, 1H), 7.77 (d, J = 8.4 Hz, 2H), 7.51-7.31 (m, 4H), 7.16 (d, J = 8.4 Hz, 1H), 7.07 (d, J = 2.2 Hz, 1H), 3.88 (s, 3H), 3.47 (s, 2H), 2.36 (m, 8H), 2.14 (s, 3H); Mass (ESI): m/z 463.5 [M + H$^+$] |
| 37 | 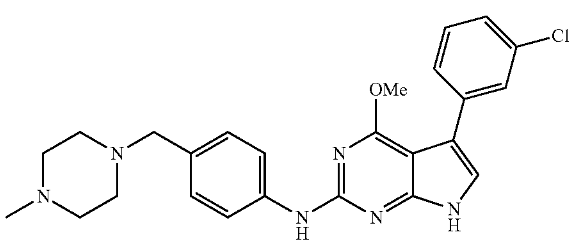 [SMILES: COc1nc(Nc2ccc(CN3CCN(C)CC3)cc2)nc2[nH]cc(-c3cccc(Cl)c3)c12] | 5-(3-chlorophenyl)-4-methoxy-N-(4-((4-methylpiperazin-1-yl)methyl)phenyl)-7H-pyrrolo[2,3-d]pyrimidin-2-amine | $^1$H NMR (500 MHz, DMSO) δ 9.15 (s, 1H), 7.74-7.70 (m, 3H), 7.6 (d, J = 7.8 Hz, 1H), 7.36-7.32 (m, 2H), 7.22 (d, J = 7.9 Hz, 1H), 7.13 (d, J = 8.5 Hz, 2H), 3.99 (s, 3H), 3.47 (s, 2H), 2.32 (m, 8H), 2.1 (s, 3H); Mass (ESI): m/z 463.4 [M + H$^+$] |
| 38 | 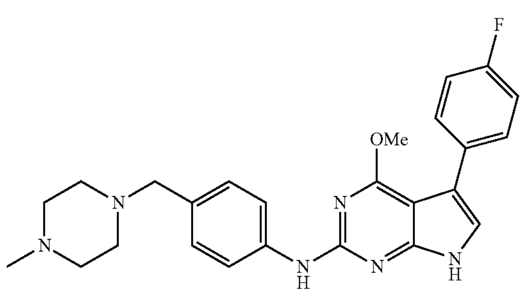 [SMILES: COc1nc(Nc2ccc(CN3CCN(C)CC3)cc2)nc2[nH]cc(-c3ccc(F)cc3)c12] | 5-(4-fluorophenyl)-4-methoxy-N-(4-((4-methylpiperazin-1-yl)methyl)phenyl)-7H-pyrrolo[2,3-d]pyrimidin-2-amine | $^1$H NMR (500 MHz, MeOD) δ 9.15 (s, 1H), 7.78 (d, J = 8.4 Hz, 1H), 7.68-7.65 (m, 2H), 7.2-7.15 (m, 5H), 4.0 (s, 3H), 3.47 (s, 2H), 2.36 (m, 8H), 2.14 (s, 3H); Mass (ESI): m/z 447.6 [M + H$^+$] |

TABLE 1-continued

| Cpd | Structure | Name | Mass |
|---|---|---|---|
| 39 | 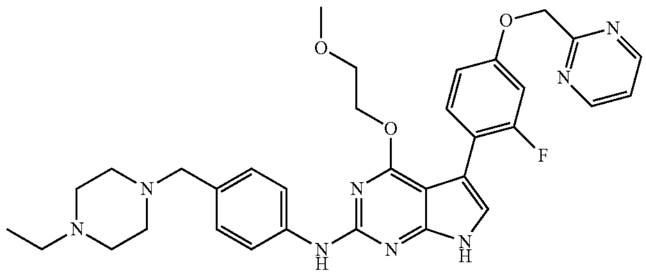 [SMILES: CCN1CCN(Cc2ccc(Nc3nc(OCCOC)c4c(-c5ccc(OCc6ncccn6)cc5F)c[nH]c4n3)cc2)CC1] | N-(4-((4-ethylpiperazin-1-yl)methyl)phenyl)-5-(2-fluoro-4-(pyrimidin-2-ylmethoxy)phenyl)-4-(2-methoxyethoxy)-7H-pyrrolo[2,3-d]pyrimidin-2-amine | ¹H NMR (600 MHz, CDCl₃): δ (ppm) 10.30 (s, 1H), 8.80 (d, J = 5.0 Hz, 2H), 7.61 (t, J = 8.6 Hz, 1H), 7.56 (d, J = 8.6 Hz, 2H), 7.27 (d, J = 5.3 Hz, 1H), 7.23 (d, J = 8.5 Hz, 2H), 7.05 (s, 1H), 6.78-6.83 (m, 2H), 6.74 (d, J = 1.7 Hz, 1H), 5.33 (s, 2H), 4.54 (dd, J = 4.6, 5.0 Hz, 2H), 3.66 (dd, J = 4.6, 5.0 Hz, 2H), 3.46 (s, 2H), 3.32 (s, 3H), 2.46 (br, 8H), 2.41 (q, J = 7.3 Hz, 4H), 1.07 (t, J = 7.3 Hz, 3H); Mass (ESI): m/z 613.70 [M + H⁺] |
| 40 | DA0191 | 3-(4-methoxy-2-((4-((4-methylpiperazin-1-yl)methyl)phenyl)amino)-7H-pyrrolo[2,3-d]pyrimidin-5-yl)-N,N-dimethylbenzamide | ¹H NMR (500 MHz, MeOD) δ 11.7 (s, 1H), 9.17 (s, 1H), 7.78 (d, J = 8.5 Hz, 2H), 7.71 (d, J = 7.9 Hz, 1H), 7.65 (s, 1H), 7.42 (t, J = 7.7 Hz, 1H), 7.29 (d, J = 2.3 Hz, 1H), 7.23 (d, J = 7.6 Hz, 1H), 7.16 (d, J = 8.5 Hz, 2H), 6.8 (t, J = 7.4 Hz, 1H), 4.0 (s, 3H), 3.47 (s, 2H), 3.0 (s, 6H), 2.36 (m, 8H), 2.14 (s, 3H); Mass (ESI): m/z 500.4 [M + H⁺] |
| 41 | 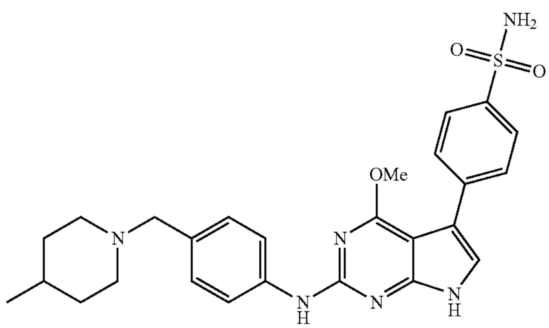 [SMILES: COc1nc(Nc2ccc(CN3CCC(C)CC3)cc2)nc2[nH]cc(-c3ccc(S(N)(=O)=O)cc3)c12] | 4-(4-methoxy-2-((4-((4-methylpiperidin-1-yl)methyl)phenyl)amino)-7H-pyrrolo[2,3-d]pyrimidin-5-yl)benzenesulfonamide | ¹H NMR (500 MHz, MeOD) δ 11.8 (s, 1H), 9.19 (s, 1H), 7.85-7.76 (m, 6H), 7.39 (s, 1H), 7.31 (bs, 2H), 7.16 (d, J = 8.5 Hz, 2H), 4.03 (s, 3H), 3.47 (s, 2H), 2.76 (d, J = 11.3 Hz, 2H), 1.86 (t, J = 10.5 Hz, 2H), 1.55 (d, J = 12.7 Hz, 2H), 1.3 (m, 1H), 1.1 (m, 2H), 0.88 (s, 3H); Mass (ESI): m/z 507.3 [M + H⁺] |
| 42 | 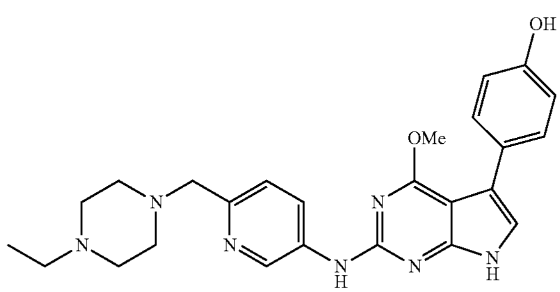 [SMILES: CCN1CCN(Cc2ccc(Nc3nc(OC)c4c(-c5ccc(O)cc5)c[nH]c4n3)cn2)CC1] | 4-(2-((6-((4-ethylpiperazin-1-yl)methyl)pyridin-3-yl)amino)-4-methoxy-7H-pyrrolo[2,3-d]pyrimidin-5-yl)phenol | ¹H NMR (500 MHz, CDCl₃) δ ppm 1.07-1.10 (m, 3H), 2.41-2.45 (m, 2H), 2.57 (br, 8H), 3.61 (s, 2H), 4.04 (s, 3H), 6.78 (d, J = 8.5 Hz, 2H), 6.95 (s, 1H), 7.39 (d, J = 8.5 Hz, 1H), 7.45 (d, J = 8.5 Hz, 2H), 8.30-8.32 (m, 1H), 8.92 (s, 1H); Mass (ESI): m/z 460.1 [M + H⁺] |
| 43 | 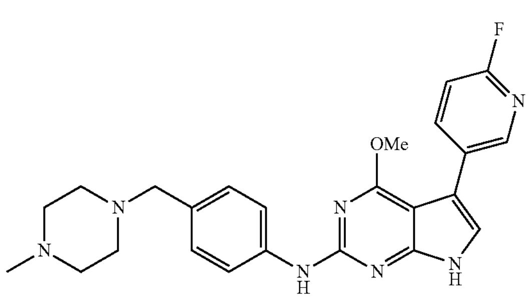 [SMILES: COc1nc(Nc2ccc(CN3CCN(C)CC3)cc2)nc2[nH]cc(-c3ccc(F)nc3)c12] | 5-(6-fluoropyridin-3-yl)-4-methoxy-N-(4-((4-methylpiperazin-1-yl)methyl)phenyl)-7H-pyrrolo[2,3-d]pyrimidin-2-amine | ¹H NMR (500 MHz, MeOD) δ 8.44 (d, J = 2 Hz, 1H), 8.22-8.18 (m, 1H), 7.79 (d, J = 8.5 Hz, 2H), 7.26 (d, J = 8.4 Hz, 2H), 7.17 (s, 1H), 7.07-7.05 (m, 1H), 4.06 (s, 3H), 3.66 (s, 2H), 2.95-2.75 (m, 8H), 2.61 (s, 3H); Mass (ESI): m/z 448.5 [M + H⁺] |

TABLE 1-continued

| Cpd | Structure | Name | Mass |
|---|---|---|---|
| 44 | 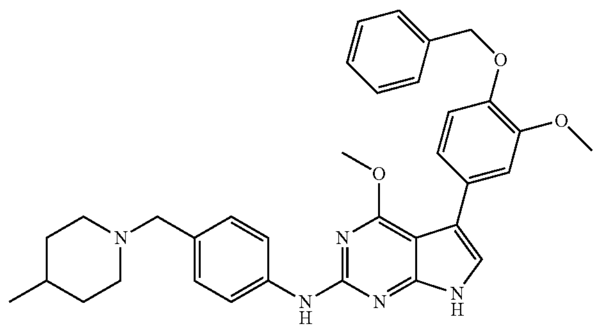 | 5-(4-(benzyloxy)-3-methoxyphenyl)-4-methoxy-N-(4-((4-methylpiperidin-1-yl)methyl)phenyl)-7H-pyrrolo[2,3-d]pyrimidin-2-amine | $^1$H NMR (500 MHz, MeOD): δ 7.77 (d, J = 8.4 Hz, 2H), 7.45 (d, J = 13 Hz, 2H), 7.36 (d, J = 8.3 Hz, 2H), 7.35 (d, J = 13 Hz, 1H), 7.30 (d, J = 13 Hz, 1H), 7.24 (d, J = 8.4 Hz, 2H), 7.11 (d, J = 8.3 Hz, 1H), 6.99 (s, 1H), 6.93 (d, J = 8.3 Hz, 1H), 5.08 (s, 2H), 4.08 (s, 3H), 3.59 (s, 2H), 2.99 (d, J = 11.4 Hz, 2H), 2.78 (t, J = 8.0 Hz, 2H), 2.18 (t, J = 11.4 Hz, 2H), 1.67 (d, J = 12.7 Hz, 2H) 1.34-1.38 (m, 1H), 1.22-1.27 (m, 2H), 0.93 (d, J = 6.4 Hz, 3H); Mass (ESI): m/z 564.2 [M + H$^+$] |
| 45 | 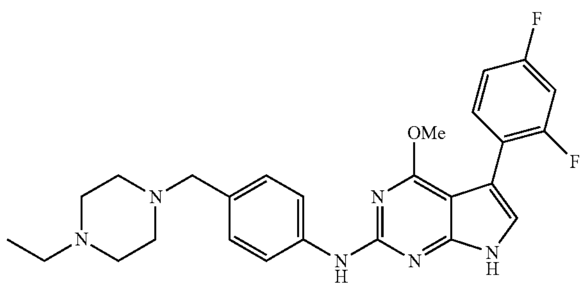 [SMILES: CCN1CCN(Cc2ccc(Nc3nc(OC)c4c(-c5ccc(F)cc5F)c[nH]c4n3)cc2)CC1] | 5-(2,4-difluorophenyl)-N-(4-((4-ethylpiperazin-1-yl)methyl)phenyl)-4-methoxy-7H-pyrrolo[2,3-d]pyrimidin-2-amine | $^1$H NMR (500 MHz, CDCl$_3$) δ ppm 106-1.09 (m, 2H), 2.40-2.44 (m, 3H), 2.51 (br, 8H), 3.49 (s, 2H), 3.98 (s, 3H), 6.93-6.97 (m, 2H), 7.01 (s, 1H), 7.22 (d, J = 8.4 Hz, 2H), 7.57-7.59 (m, 1H), 7.74 (d, J = 8.4 Hz, 2H); Mass (ESI): m/z 479.2 [M + H$^+$] |
| 46 | 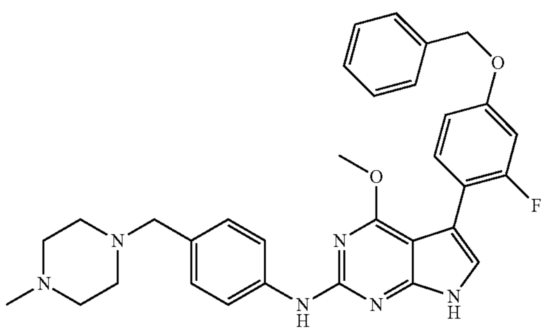 [SMILES: COc1nc(Nc2ccc(CN3CCN(C)CC3)cc2)nc2[nH]cc(-c3ccc(OCc4ccccc4)cc3F)c12] | 5-(4-(benzyloxy)-2-fluorophenyl)-4-methoxy-N-(4-((4-methylpiperazin-1-yl)methyl)phenyl)-7H-pyrrolo[2,3-d]pyrimidin-2-amine | $^1$H NMR (500 MHz, CDCl$_3$): δ 9.46 (s, 1H), 7.61 (d, J = 8.4 Hz, 2H), 7.45 (t, J = 7.2 Hz, 1H), 7.34-7.42 (m, 5H), 7.26 (d, J = 8.4 Hz, 2H), 6.97 (s, 1H), 6.76-6.82 (m, 3H), 5.08 (s, 2H), 4.00 (s, 3H), 3.49 (s, 2H), 2.55 (br, 8H), 2.34 (s, 3H); Mass (ESI): m/z 553.3 [M + H$^+$] |
| 47 | 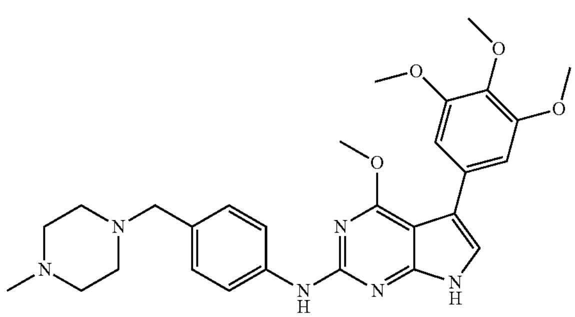 | 4-methoxy-N-(4-((4-methylpiperazin-1-yl)methyl)phenyl)-5-(3,4,5-trimethoxyphenyl)-7H-pyrrolo[2,3-d]pyrimidin-2-amine | $^1$H NMR (500 MHz, MeOD): δ 7.76 (d, J = 8.5 Hz, 2H), 7.24 (d, J = 8.5 Hz, 2H), 7.10 (s, 1H), 7.01 (s, 2H), 4.09 (s, 3H), 3.90 (s, 6H), 3.80 (s, 3H), 3.49 (s, 2H), 2.50 (br, 8H), 2.28 (s, 3H); Mass (ESI): m/z 519.4 [M + H$^+$] |
| 48 | 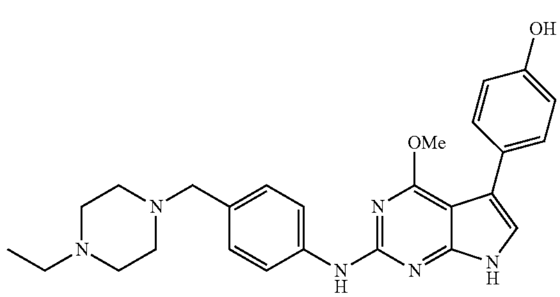 | 4-(2-((4-((4-ethylpiperazin-1-yl)methyl)phenyl)amino)-4-methoxy-7H-pyrrolo[2,3-d]pyrimidin-5-yl)phenol | $^1$H NMR (500 MHz, CDCl$_3$) δ ppm 2.15 (s, 3H), 2.51 (br, 8H), 3.49 (s, 2H), 4.03 (s, 3H), 6.78 (d, J = 8.5 Hz, 2H), 6.90 (s, 1H), 7.22 (d, J = 8.5 Hz, 2H), 7.45 (d, J = 8.5 Hz, 2H), 7.74 (d, J = 8.5 Hz, 2H); Mass (ESI): m/z 459.2 [M + H$^+$] |

TABLE 1-continued

| Cpd | Structure | Name | Mass |
|---|---|---|---|
| 49 | 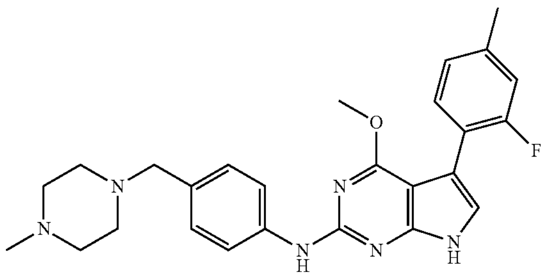 [SMILES: COc1nc(Nc2ccc(CN3CCN(C)CC3)cc2)nc2[nH]cc(-c3ccc(C)cc3F)c12] | 5-(2-fluoro-4-methylphenyl)-4-methoxy-N-(4-((4-methylpiperazin-1-yl)methyl)phenyl)-7H-pyrrolo[2,3-d]pyrimidin-2-amine | $^1$H NMR (500 MHz, CDCl$_3$): δ 9.72 (s, 1H), 7.60 (d, J = 8.4 Hz, 2H), 7.48 (t, J = 7.9 Hz, 1H), 7.26 (d, J = 8.4 Hz, 2H), 6.92-6.98 (m, 3H), 6.79 (s, 1H), 4.00 (s, 3H), 3.47 (s, 2H), 2.50 (br, 8H), 2.37 (s, 3H), 2.31 (s, 3H); Mass (ESI): m/z 461.1 [M + H$^+$] |
| 50 | 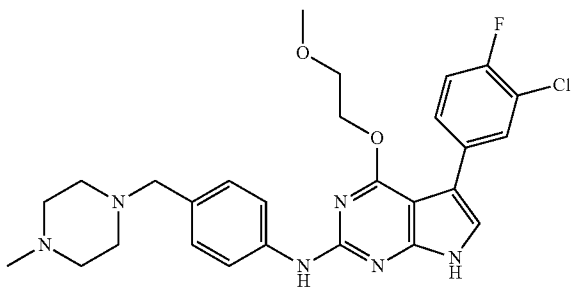 [SMILES: COCCOc1nc(Nc2ccc(CN3CCN(C)CC3)cc2)nc2[nH]cc(-c3ccc(F)c(Cl)c3)c12] | 5-(3-chloro-4-fluorophenyl)-4-(2-methoxyethoxy)-N-(4-((4-methylpiperazin-1-yl)methyl)phenyl)-7H-pyrrolo[2,3-d]pyrimidin-2-amine | $^1$H NMR (500 MHz, MeOD): δ 7.76 (d, J = 7.2 Hz, 1H), 7.64 (d, J = 8.5 Hz, 2H), 7.48-7.51 (m, 1H), 7.14 (d, J = 8.5 Hz, 2H), 7.08 (t, J = 8.9 Hz, 1H), 6.93 (s, 1H), 4.51 (t, J = 4.5 Hz, 2H), 3.70 (t, J = 4.5 Hz, 2H), 3.39 (s, 2H), 3.35 (s, 3H), 2.43 (br, 8H), 2.21 (s, 3H); Mass (ESI): m/z 525.2 [M + H$^+$] |
| 51 | 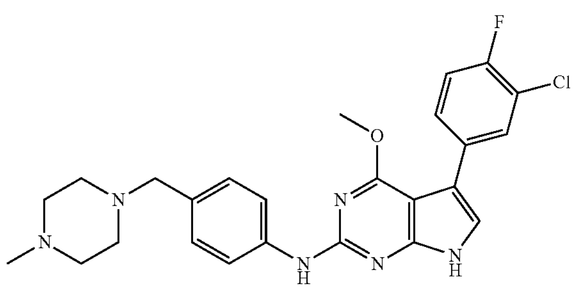 [SMILES: COc1nc(Nc2ccc(CN3CCN(C)CC3)cc2)nc2[nH]cc(-c3ccc(F)c(Cl)c3)c12] | 5-(3-chloro-4-fluorophenyl)-4-methoxy-N-(4-((4-methylpiperazin-1-yl)methyl)phenyl)-7H-pyrrolo[2,3-d]pyrimidin-2-amine | $^1$H NMR (500 MHz, MeOD): δ 7.64 (d, J = 7.2 Hz, 1H), 7.58 (d, J = 8.4 Hz, 2H), 7.41-7.43 (m, 1H), 7.20 (d, J = 8.4 Hz, 2H), 7.07 (t, J = 8.8 Hz, 1H), 6.82 (s, 1H), 4.00 (s, 3H), 3.87 (s, 3H), 3.43 (s, 2H), 2.46 (br, 8H), 2.24 (s, 3H); Mass (ESI): m/z 481.3 [M + H$^+$] |
| 52 | 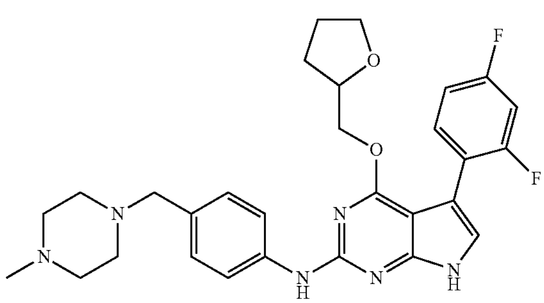 [SMILES: CN1CCN(Cc2ccc(Nc3nc(OCC4CCCO4)c4c(-c5ccc(F)cc5F)c[nH]c4n3)cc2)CC1] | 5-(2,4-difluoro phenyl)-N-(4-((4-methylpiperazin-1-yl)methyl)phenyl)-4-((tetrahydrofuran-2-yl)methoxy)-7H-pyrrolo[2,3-d]pyrimidin-2-amine | $^1$H NMR (500 MHz, MeOD) δ 7.77 (d, J = 8.5 Hz, 2H), 7.64-7.63 (m, 1H), 7.27 (d, J = 8.4 Hz, 2H), 7.04-6.93 (m, 3H), 4.46-4.45 (m, 2H), 4.19-4.17 (m, 1H), 3.73-3.69 (m, 4H), 3.02-2.79 (m, 8H), 2.67 (s, 3H), 1.87-1.7 (m, 4H); Mass (ESI): m/z 535.2 [M + H$^+$] |
| 53 | 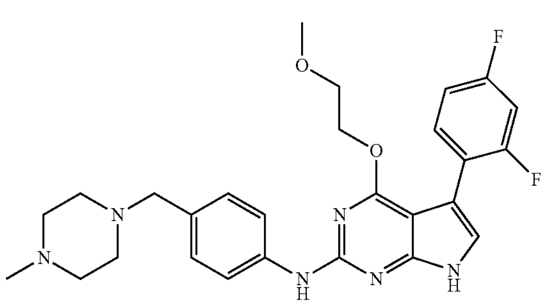 [SMILES: COCCOc1nc(Nc2ccc(CN3CCN(C)CC3)cc2)nc2[nH]cc(-c3ccc(F)cc3F)c12] | 5-(2,4-difluoro phenyl)-4-(2-methoxyethoxy)-N-(4-((4-methylpiperazin-1-yl)methyl)phenyl)-7H-pyrrolo[2,3-d]pyrimidin-2-amine | $^1$H NMR (500 MHz, MeOD) δ 7.77 (d, J = 8.4 Hz, 2H), 7.73-7.69 (m, 1H), 7.26 (d, J = 8.4 Hz, 2H), 7.07 (m, 1H), 6.98-6.93 (m, 2H), 4.56 (t, J = 4.7 Hz, 2H), 3.7 (t, J = 4.7 Hz, 2H), 3.04 (s, 2H), 3.34 (bs, 2H), 2.88-2.72 (m, 8H), 2.56 (s, 3H); Mass (ESI): m/z 509.3 [M + H$^+$] |

TABLE 1-continued

| Cpd | Structure | Name | Mass |
|---|---|---|---|
| 54 | 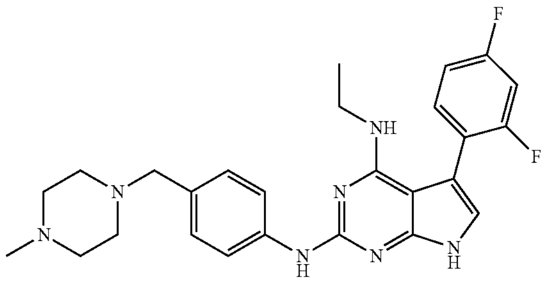 [SMILES: CCNc1nc(Nc2ccc(CN3CCN(C)CC3)cc2)nc2[nH]cc(-c3ccc(F)cc3F)c12] | 5-(2,4-difluoro phenyl)-N4-ethyl-N2-(4-((4-methyl piperazin-1-yl) methyl)phenyl)-7H-pyrrolo[2,3-d] pyrimidine-2,4-diamine | $^1$H NMR (500 MHz, MeOD) δ 7.74 (d, J = 8.4 Hz, 2H), 7.46-7.43 (m, 1H), 7.23 (d, J = 8.4 Hz, 2H), 7.11-7.1 (m, 2H), 6.83 (s, 1H), 3.66 (s, 2H), 3.53-3.49 (m, 2H), 2.96-2.76 (m, 8H), 2.61 (s,3H), 1.15 (t, J = 7.2 Hz, 3H); Mass (ESI): m/z 478.3 [M + H$^+$] |
| 55 | 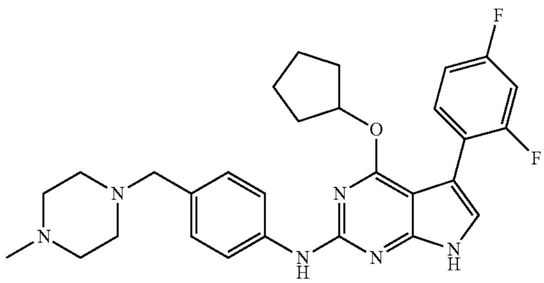 [SMILES: CN1CCN(Cc2ccc(Nc3nc(OC4CCCC4)c4c(-c5ccc(F)cc5F)c[nH]c4n3)cc2)CC1] | 4-(cyclopentyloxy)-5-(2,4-difluorophenyl)-N-(4-((4-methylpiperazin-1-yl)methyl)phenyl)-7H-pyrrolo[2,3-d]pyrimidin-2-amine | $^1$H NMR (500 MHz, MeOD) δ 7.83 (d, J = 8.4 Hz, 2H), 7.58-7.57 (m, 1H), 7.33 (d, J = 8.4 Hz, 2H), 7.04 (s, 1H), 6.99-6.93 (m, 2H), 3.92 (bs, 1H), 3.35 (bs, 2H), 3.06 (m, 8H), 2.83 (s, 3H), 2.15-1.91 (m, 2H), 1.81 (m, 2H), 1.67-1.63 (m, 2H); Mass (ESI): m/z 519.5 [M + H$^+$] |
| 56 | 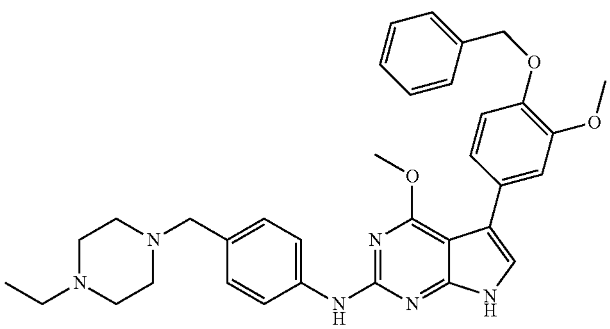 [SMILES: CCN1CCN(Cc2ccc(Nc3nc(OC)c4c(-c5ccc(OCc6ccccc6)c(OC)c5)c[nH]c4n3)cc2)CC1] | 5-(4-(benzyloxy)-3-methoxyphenyl)-N-(4-((4-ethylpiperazin-1-yl)methyl)phenyl)-4-methoxy-7H-pyrrolo[2,3-d] pyrimidin-2-amine | $^1$H NMR (500 MHz, MeOD): δ 7.71 (d, J = 8.4 Hz, 2H), 7.40 (d, J = 7.2 Hz, 2H), 7.30-7.34 (m, 3H), 7.26 (d, J = 7.2 Hz, 1H), 7.17 (d, J = 8.4 Hz, 2H), 7.06 (d, J = 8.3 Hz, 1H), 6.91 (s, 1H), 6.86 (d, J = 8.3 Hz, 1H), 5.01 (s, 2H), 3.99 (s, 3H), 3.84 (s, 3H), 3.41 (s, 2H), 2.46 (br, 8H), 2.37 (q, J = 7.2 Hz, 2H), 1.03 (t, J = 7.2 Hz, 3H); Mass (ESI): m/z 579.3 [M + H$^+$] |
| 57 | 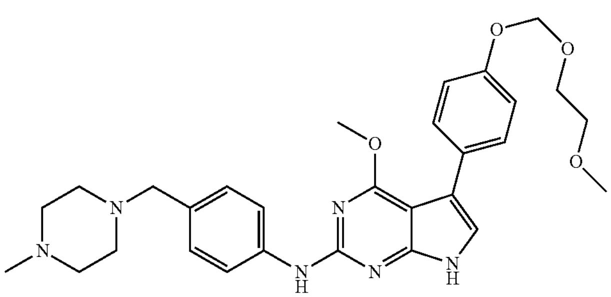 | 4-methoxy-5-(4-((2-methoxy ethoxy)methoxy)phenyl)-N-(4-((4-methyl piperazin-1-yl)methyl)phenyl)-7H-pyrrolo[2,3-d]pyrimidin-2-amine | $^1$H NMR (500 MHz, MeOD): δ 7.70 (d, J = 8.5 Hz, 2H), 7.51 (d, J = 8.7 Hz, 2H), 7.17 (d, J = 8.5 Hz, 2H), 6.98 (d, J = 8.7 Hz, 2H), 6.88 (s, 1H), 5.22 (s, 2H), 3.98 (s, 3H), 3.77 (dd, J = 4.7, 6.1 Hz, 2H), 3.53 (dd, J = 4.7, 6.1 Hz, 2H), 3.41 (s, 2H), 2.43 (br, 8H), 2.21 (s, 3H); Mass (ESI): m/z 533.4 [M + H$^+$] |
| 58 | 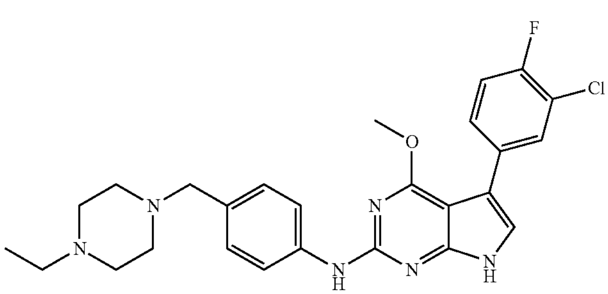 [SMILES: CCN1CCN(Cc2ccc(Nc3nc(OC)c4c(-c5ccc(F)c(Cl)c5)c[nH]c4n3)cc2)CC1] | 5-(3-chloro-4-fluorophenyl)-N-(4-((4-ethylpiperazin-1-yl)methyl)phenyl)-4-methoxy-7H-pyrrolo[2,3-d]pyrimidin-2-amine | $^1$H NMR (500 MHz, CDCl$_3$): δ 7.63 (d, J = 7.2 Hz, 1H), 7.56 (d, J = 8.4 Hz, 2H), 7.39-7.41 (m, 1H), 7.23 (d, J = 8.4 Hz, 2H), 7.08 (t, J = 8.8 Hz, 1H), 6.41 (s, 1H), 4.01 (s, 3H), 3.44 (s, 2H), 2.47 (br, 8H), 2.39 (q, J = 7.2 Hz, 2H), 1.05 (t, J = 7.2 Hz, 3H); Mass (ESI): m/z 495.5 [M + H$^+$] |

TABLE 1-continued

| Cpd | Structure | Name | Mass |
|---|---|---|---|
| 59 | 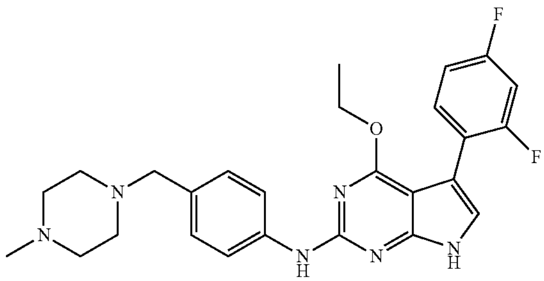 [SMILES: CCOc1nc(Nc2ccc(CN3CCN(C)CC3)cc2)nc2[nH]cc(-c3ccc(F)cc3F)c12] | 5-(2,4-difluoro phenyl)-4-ethoxy-N-(4-((4-methyl piperazin-1-yl) methyl)phenyl)-7H-pyrrolo[2,3-d] pyrimidin-2-amine | ¹H NMR (500 MHz, MeOD) δ 7.76 (d, J = 8.5 Hz, 2H), 7.63-7.58 (m, 1H), 7.24 (d, J = 8.4 Hz, 2H), 7.02 (s, 1H), 6.97-6.92 (m, 2H), 4.51 (m, 2H), 3.63 (s, 2H), 2.93-2.74 (m, 8H), 2.59 (s, 3H), 1.32 (t, J = 1.1 Hz, 3H); Mass (ESI): m/z 479.2 [M + H⁺] |
| 60 | 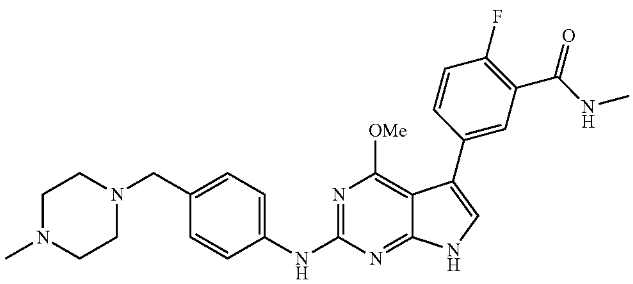 | 2-fluoro-5-(4-methoxy-2-((4-((4-methylpiperazin-1-yl)methyl)phenyl)amino)-7H-pyrrolo[2,3-d]pyrimidin-5-yl)-N-methylbenzamide | ¹H NMR (500 MHz, MeOD) δ 8.08-8.06 (m, 1H), 7.81-7.79 (m, 1H), 7.76 (d, J = 8.4 Hz, 2H), 7.25 (d, J = 8.4 Hz, 2H), 7.2-7.17 (m, 1H), 7.11 (s, 1H), 4.06 (s, 3H), 3.51 (s, 2H), 2.96 (s, 3H), 2.54 (bs, 8H), 2.3 (s, 3H); Mass (ESI): m/z 504.5 [M + H⁺] |
| 61 | 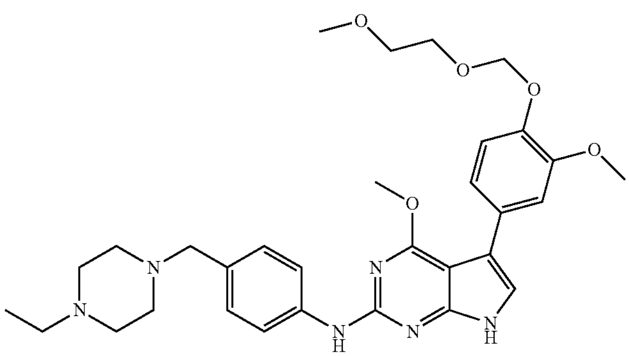 [SMILES: CCN1CCN(Cc2ccc(Nc3nc(OC)c4c(-c5ccc(OCOCCOC)c(OC)c5)c[nH]c4n3)cc2)CC1] | N-(4-((4-ethyl piperazin-1-yl) methyl)phenyl)-4-methoxy-5-(3-methoxy-4-((2-methoxy ethoxy)methoxy)phenyl)-7H-pyrrolo[2,3-d]pyrimidin-2-amine | ¹H NMR (500 MHz, CDCl₃): δ 9.95 (s, 1H), 7.60 (d, J = 8.3 Hz, 2H), 7.18-7.29 (m, 4H), 7.08-7.10 (m, 1H), 7.04 (s, 1H), 6.68 (s, 1H), 5.34 (s, 2H), 4.04 (s, 3H), 3.89-3.91 (m, 5H), 3.58 (t, J = 4.7 Hz, 2H), 3.45 (s, 2H), 3.38 (s, 3H), 2.49 (br, 8H), 2.41 (q, J = 7.2 Hz, 2H), 1.06 (t, J = 7.2 Hz, 3H); Mass (ESI): m/z 577.4 [M + H⁺] |
| 62 | 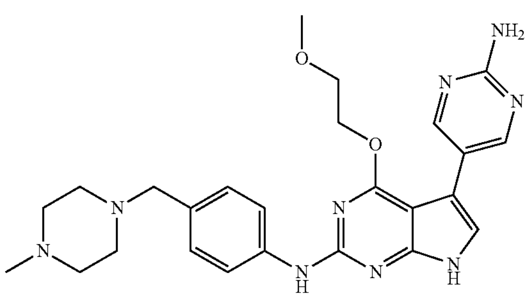 [SMILES: COCCOc1nc(Nc2ccc(CN3CCN(C)CC3)cc2)nc2[nH]cc(-c3cnc(N)nc3)c12] | 5-(2-aminopyrimidin-5-yl)-4-(2-methoxyethoxy)-N-(4-((4-methylpiperazin-1-yl) methyl)phenyl)-7H-pyrrolo [2,3-d]pyrimidin-2-amine | ¹H NMR (500 MHz, CDCl₃) δ ppm 2.29 (s, 3H), 2.70 (br, 8H), 3.40 (s, 3H), 3.74-3.76 (m, 2H), 4.59-4.61 (m, 2H), 5.29 (s, 2H), 6.86 (s, 1H), 7.25 (s, 2H), 7.59 (d, J = 8.3 Hz, 2H), 8.57-8.58 (m, 2H); Mass (ESI): m/z 490.2 [M + H⁺] |
| 63 | 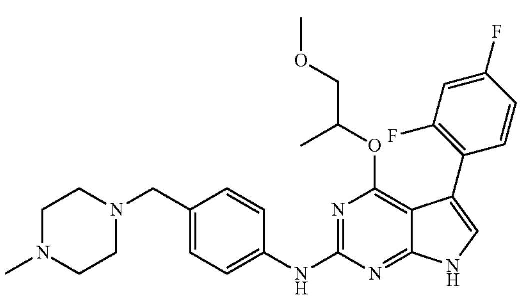 [SMILES: COCC(C)Oc1nc(Nc2ccc(CN3CCN(C)CC3)cc2)nc2[nH]cc(-c3ccc(F)cc3F)c12] | 5-(2,4-difluorophenyl)-4-((1-methoxypropan-2-yl)oxy)-N-(4-((4-methylpiperazin-1-yl)methyl)phenyl)-7H-pyrrolo[2,3-d]pyrimidin-2-amine | ¹H NMR (500 MHz, DMSO) δ 11.7 (s, 1H), 9.17 (s, 1H), 7.78 (d, J = 8.4 Hz, 2H), 7.66 (m, 1H), 7.27-7.07 (m, 5H), 5.52-5.49 (m, 2H), 3.41 (m, 4H), 3.22 (s, 3H), 2.73 (m, 8H), 2.44 (s, 3H), 1.26 (d, J = 6.4 Hz, 3H); Mass (ESI): m/z 523.3 [M + H⁺] |

TABLE 1-continued

| Cpd | Structure | Name | Mass |
|---|---|---|---|
| 64 | 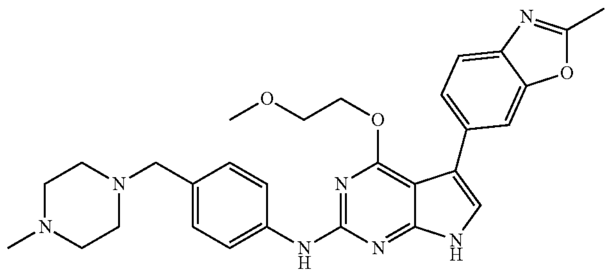 | 4-(2-methoxyethoxy)-5-(2-methylbenzo[d]oxazol-6-yl)-N-(4-((4-methylpiperazin-1-yl)methyl)phenyl)-7H-pyrrolo[2,3-d]pyrimidin-2-amine | $^1$H NMR (500 MHz, MeOD): δ 7.92 (s, 1H), 7.70 (d, J = 8.4 Hz, 2H), 7.63 (d, J = 8.3 Hz, 1H), 7.50 (d, J = 8.3 Hz, 1H), 7.19 (d, J = 8.4 Hz, 2H), 7.06 (s, 1H), 4.56 (t, J = 4.5 Hz, 2H), 3.71 (t, J = 4.5 Hz, 2H), 3.44 (s, 2H), 3.37 (s, 3H), 2.60 (s, 3H), 2.46 (br, 8H), 2.25 (s, 3H); Mass (ESI): m/z 528.4 [M + H$^+$] |
| 65 | 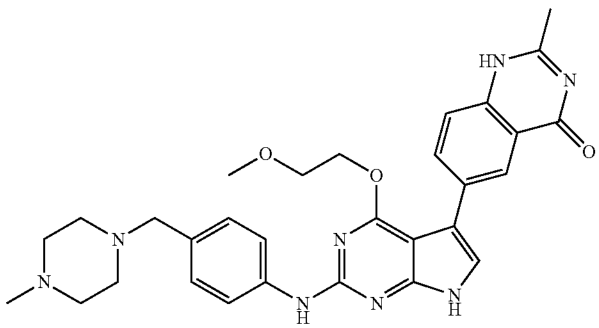 [SMILES: COCCOc1nc(Nc2ccc(CN3CCN(C)CC3)cc2)nc2[nH]cc(-c3ccc4[nH]c(C)nc(=O)c4c3)c12] | 6-(4-(2-methoxyethoxy)-2-((4-((4-methylpiperazin-1-yl)methyl)phenyl)amino)-7H-pyrrolo[2,3-d]pyrimidin-5-yl)-2-methylquinazolin-4(1H)-one | $^1$H NMR (500 MHz, MeOD): δ 8.49 (d, J = 2.0 Hz, 1H), 8.15 (dd, J = 2.0, 8.5 Hz, 1H), 7.74 (d, J = 8.5 Hz, 2H), 7.55 (d, J = 8.5 Hz, 1H), 7.23 (d, J = 8.5 Hz, 2H), 7.17 (s, 1H), 4.60 (t, J = 4.6 Hz, 2H), 3.82 (t, J = 4.6 Hz, 2H), 3.59 (s, 2H), 3.33 (s, 3H), 2.68 (br, 8H), 2.51 (s, 3H), 2.43 (s, 3H); Mass (ESI): m/z 555.5 [M + H$^+$] |
| 66 | 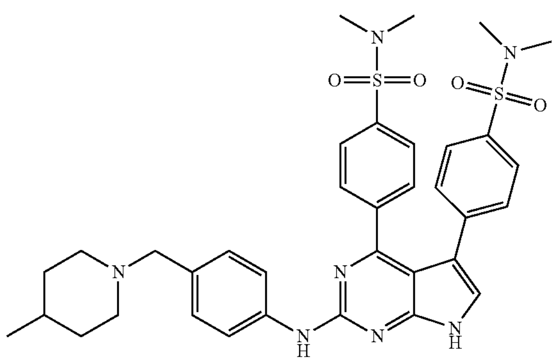 | 4,4'-(2-((4-((4-methylpiperidin-1-yl)methyl)phenyl)amino)-7H-pyrrolo[2,3-d]pyrimidine-4,5-diyl)bis(N,N-dimethylbenzenesulfonamide) | $^1$H NMR (500 MHz, DMSO-d6): δ 9.56 (s, 1H), 7.81 (d, J = 8.5 Hz, 2H), 7.60 (d, J = 8.5 Hz, 2H), 7.59 (s, 1H), 7.57 (d, J = 8.3 Hz, 2H), 7.40 (d, J = 8.3 Hz, 2H), 7.19 (d, J = 8.1 Hz, 2H), 7.18 (d, J = 8.1 Hz, 2H), 3.37 (s, 2H), 2.76 (d, J = 11.3 Hz, 2H), 2.56 (s, 6H), 2.54 (s, 6H), 1.85 (t, J = 10.7 Hz, 2H), 1.54 (d, J = 11.3 Hz, 2H), 1.30 (br, 1H), 1.09-1.14 (m, 2H), 0.87 (d, J = 6.5 Hz, 3H); Mass (ESI): m/z 688.59 [M + H$^+$] |
| 67 | 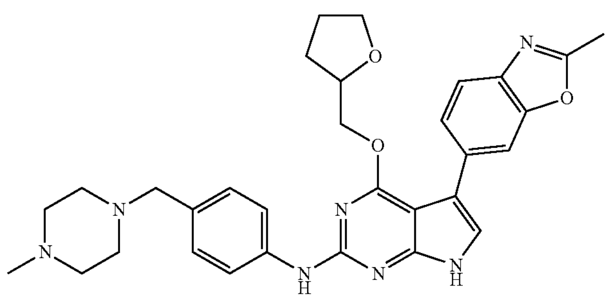 | 5-(2-methylbenzo[d]oxazol-6-yl)-N-(4-((4-methylpiperazin-1-yl)methyl)phenyl)-4-((tetrahydrofuran-2-yl)methoxy)-7H-pyrrolo[2,3-d]pyrimidin-2-amine | $^1$H NMR (500 MHz, MeOD): δ 7.91 (s, 1H), 7.74 (d, J = 8.0 Hz, 2H), 7.65 (d, J = 8.4 Hz, 1H), 7.54 (d, J = 8.4 Hz, 1H), 7.24 (d, J = 8.0 Hz, 2H), 7.10-7.11 (m, 1H), 4.51-4.53 (m, 2H), 4.21-4.26 (m, 1H), 3.71-3.80 (m, 2H), 3.49 (s, 2H), 2.64 (s, 3H), 2.50 (br, 8H), 2.28 (s, 3H), 1.97-2.02 (m, 1H), 1.80-1.87 (m, 1H), 1.72-1.80 (m, 2H); Mass (ESI): m/z 554.3 [M + H$^+$] |
| 68 | 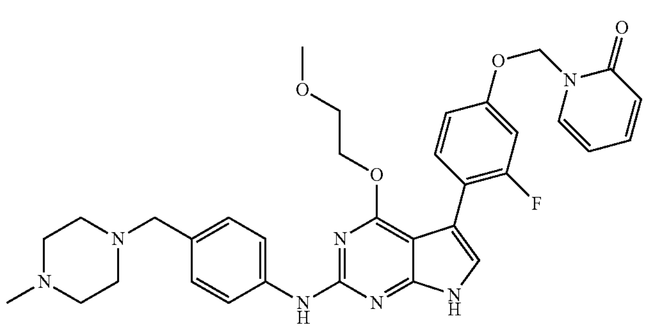 [SMILES: COCCOc1nc(Nc2ccc(CN3CCN(C)CC3)cc2)nc2[nH]cc(-c3ccc(OCn4ccccc4=O)cc3F)c12] | 1-((3-fluoro-4-(4-(2-methoxyethoxy)-2-((4-((4-methylpiperazin-1-yl)methyl)phenyl)amino)-7H-pyrrolo[2,3-d]pyrimidin-5-yl)phenoxy)methyl)pyridin-2(1H)-one | $^1$H NMR (600 MHz, MeOD) δ 7.79-7.73 (m, 2H), 7.66 (s, 1H), 7.58 (s, 1H), 7.26 (d, J = 8.5 Hz, 2H), 7.05 (d, J = 1.9 Hz, 1H), 6.93 (dd, J = 13.1, 10.1 Hz, 2H), 6.61 (d, J = 9.2 Hz, 1H), 6.45 (d, J = 1.3 Hz, 1H), 6.00 (s, 2H), 4.60-4.53 (m, 2H), 3.71 (dd, J = 5.3, 4.0 Hz, 2H), 3.53 (s, 2H), 3.32-3.30 (m, 3H), 2.52 (s, 8H), 2.35-2.27 (m, 3H). Mass (ESI): m/z 614.46 [M + H$^+$] |

TABLE 1-continued

| Cpd | Structure | Name | Mass |
|---|---|---|---|
| 69 | 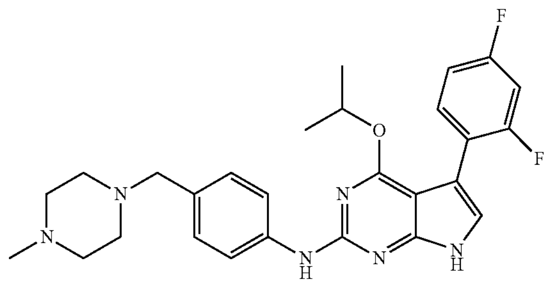 [SMILES: CC(C)Oc1nc(Nc2ccc(CN3CCN(C)CC3)cc2)nc2[nH]cc(-c3ccc(F)cc3F)c12] | 5-(2,4-difluorophenyl)-4-isopropoxy-N-(4-((4-methylpiperazin-1-yl)methyl)phenyl)-7H-pyrrolo[2,3-d]pyrimidin-2-amine | $^1$H NMR (500 MHz, MeOD) δ 7.76-7.75 (m, 2H), 7.65-7.62 (m, 1H), 7.26 (d, J = 8.7 Hz, 2H), 7.03 (d, J = 1.6 Hz, 1H), 6.99-6.95 (m, 2H), 5.53-5.51 (m, 1H), 3.63 (bs, 2H), 2.61 (m, 8H), 2.55 (s, 3H), 1.35 (d, J = 6.4 Hz, 6H); |
| 70 | 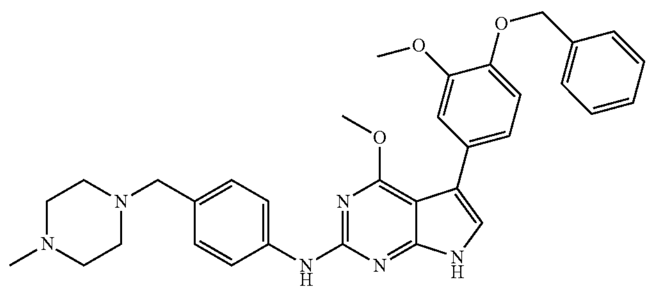 [SMILES: COc1cc(-c2c[nH]c3nc(Nc4ccc(CN5CCN(C)CC5)cc4)nc(OC)c23)ccc1OCc1ccccc1] | 5-(4-(benzyloxy)-3-methoxyphenyl)-4-methoxy-N-(4-((4-methylpiperazin-1-yl)methyl)phenyl)-7H-pyrrolo[2,3-d]pyrimidin-2-amine | $^1$H NMR (500 MHz, MeOD): δ (ppm) 7.74 (d, J = 8.0 Hz, 2H), 7.46 (d, J = 6.5 Hz, 2H), 7.35-7.37 (m, 3H), 7.28-7.31 (m, 1H), 7.23 (d, J = 6.5 Hz, 2H), 7.12 (d, J = 8.0 Hz, 1H), 6.99 (s, 1H), 6.54 (d, J = 8.6 Hz, 1H), 5.10 (s, 2H), 4.05 (s, 3H), 3.90 (s, 3H), 3.48 (s, 2H), 2.49 (br, 8H), 2.27 (s, 3H); Mass (ESI): m/z 565.2 [M + H$^+$] |
| 71 | 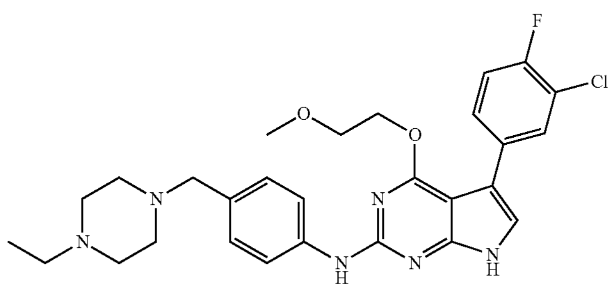 [SMILES: CCN1CCN(Cc2ccc(Nc3nc(OCCOC)c4c(-c5ccc(F)c(Cl)c5)c[nH]c4n3)cc2)CC1] | 5-(3-chloro-4-fluorophenyl)-N-(4-((4-ethylpiperazin-1-yl)methyl)phenyl)-4-(2-methoxyethoxy)-7H-pyrrolo[2,3-d]pyrimidin-2-amine | $^1$H NMR (500 MHz, CDCl$_3$): δ (ppm) 7.73 (dd, J = 2.1, 7.2 Hz, 1H), 7.55 (d, J = 8.4 Hz, 2H), 7.44-7.46 (m, 1H), 7.25 (d, J = 8.4 Hz, 2H), 7.08 (t, J = 8.7 Hz, 1H), 7.00 (s, 1H), 6.49 (s, 1H), 4.60 (t, J = 4.7 Hz, 2H), 3.76 (t, J = 4.7 Hz, 2H), 3.46 (s, 2H), 3.41 (s, 3H), 2.49 (br, 8H), 2.43 (q, J = 7.2 Hz, 2H), 1.08 (t, J = 1.2 Hz, 3H); Mass (ESI): m/z 539.3 [M + H$^+$] |
| 72 | 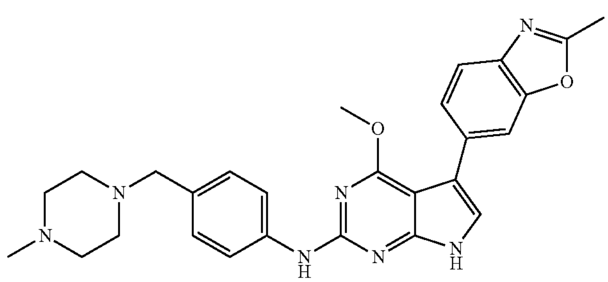 | 4-methoxy-5-(2-methylbenzo[d]oxazol-6-yl)-N-(4-((4-methylpiperazin-1-yl)methyl)phenyl)-7H-pyrrolo[2,3-d]pyrimidin-2-amine | $^1$H NMR (500 MHz, MeOD): δ (ppm) 7.69 (d, J = 7.8 Hz, 2H), 7.53 (d, J = 8.3 Hz, 1H), 7.23 (s, 1H), 7.17 (d, J = 7.8 Hz, 2H), 7.10 (d, J = 8.3 Hz, 1H), 6.94 (s, 1H), 4.02 (s, 3H), 3.41 (s, 2H), 2.44 (br, 8H), 2.22 (s, 3H), 2.18 (s, 3H); Mass (ESI): m/z 484.1 [M + H$^+$] |
| 73 | 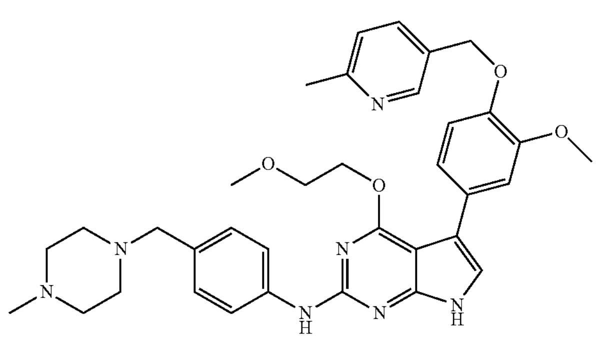 | 5-(3-methoxy-4-((6-methylpyridin-3-yl)methoxy)phenyl)-4-(2-methoxyethoxy)-N-(4-((4-methylpiperazin-1-yl)methyl)phenyl)-7H-pyrrolo[2,3-d]pyrimidin-2-amine | $^1$H NMR (500 MHz, DMSO-d6): δ (ppm) 11.55 (s, 1H), 9.09 (s, 1H), 8.51 (s, 1H), 7.74 (d, J = 8.2 Hz, 3H), 7.29 (s, 1H), 7.27 (d, J = 8.2 Hz, 1H), 7.21 (d, J = 8.2 Hz, 1H), 7.18 (s, 1H), 7.15 (d, J = 8.2 Hz, 2H), 6.99 (d, J = 8.2 Hz, 1H), 5.09 (s, 2H), 4.59 (t, J = 4.3 Hz, 2H), 3.83 (s, 3H), 3.68 (t, J = 4.3 Hz, 2H), 3.36 (s, 2H), 3.24 (s, 3H), 2.46 (s, 3H), 2.33 (br, 8H), 2.13 (s, 3H); Mass (ESI): m/z 624.5 [M + H$^+$] |

TABLE 1-continued

| Cpd | Structure | Name | Mass |
|---|---|---|---|
| 74 | 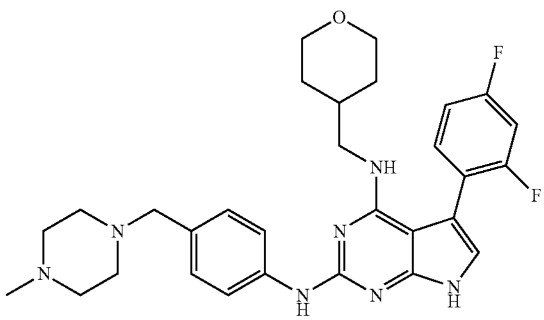 [SMILES: CN1CCN(Cc2ccc(Nc3nc(NCC4CCOCC4)c4c(-c5ccc(F)cc5F)c[nH]c4n3)cc2)CC1] | 5-(2,4-difluorophenyl)-N2-(4-((4-methylpiperazin-1-yl)methyl)phenyl)-N4-((tetrahydro-2H-pyran-4-yl)methyl)-7H-pyrrolo[2,3-d]pyrimidine-2,4-diamine | $^1$H NMR (600 MHz, CDCl$_3$) δ (ppm) 7.59 (d, J = 8.7 Hz, 2H), 7.35-7.39 (m, 1H), 7.24 (d, J = 8.2 Hz, 2H), 6.94-6.99 (m, 2H), 6.82 (s, 1H), 6.70 (s, 1H), 4.73 (t, J = 6.1 Hz, 1H), 3.97 (dd, J = 3.9, 11.7 Hz, 2H), 3.48 (s, 2H), 3.39 (t, J = 6.5 Hz, 2H), 3.35 (td, J = 1.7, 11.7 Hz, 2H), 2.54 (br, 8H), 2.33 (s, 3H), 1.81-1.88 (m, 1H), 1.56-1.58 (m, 2H), 1.26-1.33 (m, 2H); Mass (ESI): m/z 548.42 [M + H$^+$] |
| 75 | 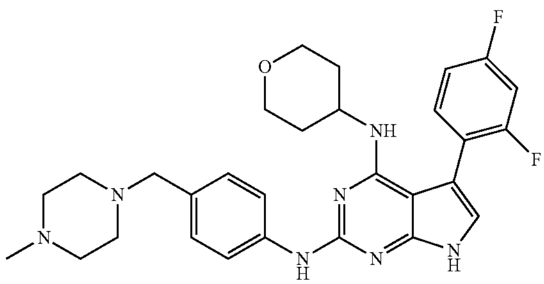 [SMILES: CN1CCN(Cc2ccc(Nc3nc(NC4CCOCC4)c4c(-c5ccc(F)cc5F)c[nH]c4n3)cc2)CC1] | 5-(2,4-difluorophenyl)-N2-(4-((4-methylpiperazin-1-yl)methyl)phenyl)-N4-(tetrahydro-2H-pyran-4-yl)-7H-pyrrolo[2,3-d]pyrimidine-2,4-diamine | $^1$H NMR (600 MHz, MeOD) δ (ppm) 7.72 (d, J = 8.6 Hz, 2H), 7.55-7.60 (m, 1H), 7.22 (d, J = 8.5 Hz, 2H), 6.99 (d, J = 1.5 Hz, 1H), 6.89-6.94 (m, 2H), 5.62-5.65 (m, 1H), 3.48 (s, 2H), 2.50 (br, 8H), 2.27 (s, 3H), 1.89-1.95 (m, 2H), 1.78-1.83 (m, 2H), 1.58-1.70 (m, 4H); Mass (ESI): m/z 534.22 [M + H$^+$] |
| 76 | 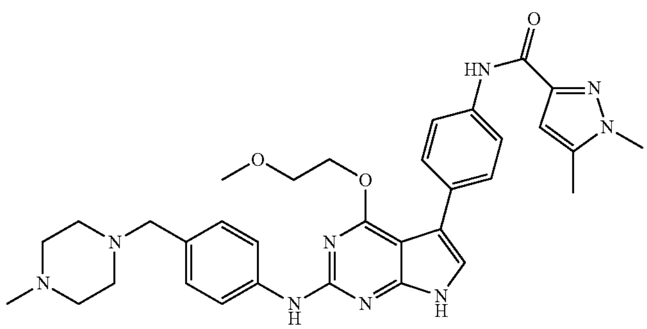 | N-(4-(4-(2-methoxyethoxy)-2-((4-((4-methylpiperazin-1-yl)methyl)phenyl)amino)-7H-pyrrolo[2,3-d]pyrimidin-5-yl)phenyl)-1,5-dimethyl-7H-pyrazole-3-carboxamide | $^1$H NMR (600 MHz, CDCl$_3$, rotamer observed): δ (ppm) 8.67 (s, 1H), 7.62-7.66 (m, 4H), 7.55 (d, J = 8.3 Hz, 2H), 7.20 (d, J = 8.3 Hz, 2H), 6.61 (s, 1H), 4.56 (t, J = 4.7 Hz, 2H), 3.80 (s, 3H), 3.72 (t, J = 4.7 Hz, 2H), 3.43 (s, 2H), 3.40 (s, 3H), 2.50 (br, 8H), 2.29 (s, 3H), 2.28 (s, 3H); Mass (ESI): m/z 610.4 [M + H$^+$] |
| 77 | 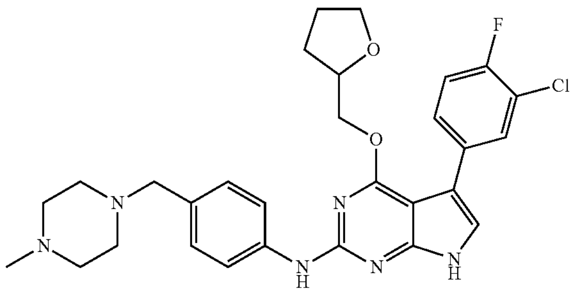 [SMILES: CN1CCN(Cc2ccc(Nc3nc(OCC4CCCO4)c4c(-c5ccc(F)c(Cl)c5)c[nH]c4n3)cc2)CC1] | 5-(3-chloro-4-fluorophenyl)-N-(4-((4-methylpiperazin-1-yl)methyl)phenyl)-4-((tetrahydrofuran-2-yl)methoxy)-7H-pyrrolo[2,3-d]pyrimidin-2-amine | $^1$H NMR (600 MHz, MeOD): δ (ppm) 7.84-7.83 (m, 1H), 7.76-7.74 (m, 2H), 7.62-7.6 (m, 1H), 7.27 (m, 2H), 7.21 (m, 1H), 7.10 (d, J = 3.8 Hz, 1H), 4.55-4.52 (m, 2H), 4.32 (m, 2H), 3.84-3.8 (m, 2H), 3.53 (s, 3H), 2.6 (bs, 8H), 2.33 (s, 3H), 2.08 (m, 2H), 1.91 (m, 2H), 1.77 (m, 1H); Mass (ESI): m/z 551.2 [M + H$^+$] |
| 78 | 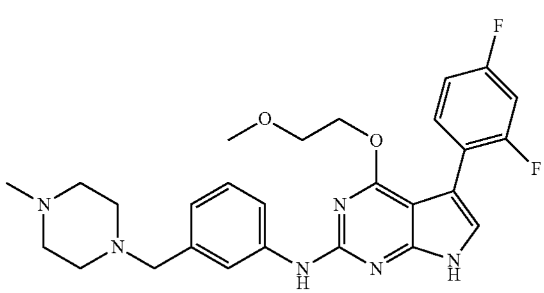 [SMILES: COCCOc1nc(Nc2cccc(CN3CCN(C)CC3)c2)nc2[nH]cc(-c3ccc(F)cc3F)c12] | 5-(2,4-difluorophenyl)-4-(2-methoxyethoxy)-N-(3-((4-methylpiperazin-1-yl)methyl)phenyl)-7H-pyrrolo[2,3-d]pyrimidin-2-amine | $^1$H NMR (600 MHz, MeOD): δ (ppm) 7.83 (s, 1H), 7.69 (d, J = 9.6 Hz, 2H), 7.27 (m, 2H), 7.1 (s, 1H), 6.98 (m, 3H), 4.62 (d, J = 3 Hz, 2H), 3.73 (d, J = 3 Hz, 2H), 3.65 (s, 2H), 3.36 (s, 3H), 2.9 (bs, 8H), 2.59 (s, 3H); Mass (ESI): m/z 509.3 [M + H$^+$] |

TABLE 1-continued

| Cpd | Structure | Name | Mass |
|---|---|---|---|
| 79 | 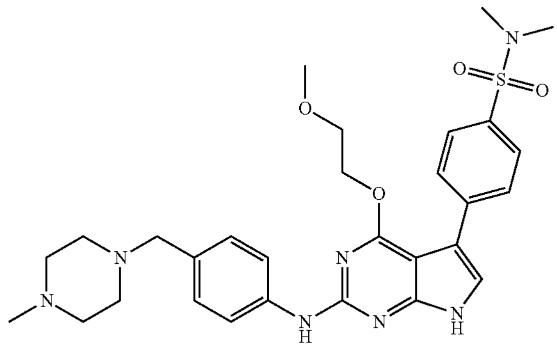 | 4-(4-(2-methoxyethoxy)-2-((4-((4-methylpiperazin-1-yl)methyl)phenyl)amino)-7H-pyrrolo[2,3-d]pyrimidin-5-yl)-N,N-dimethylbenzenesulfonamide | $^1$H NMR (600 MHz, MeOD/CDCl$_3$): δ (ppm) 7.97 (d, J = 8.8 Hz, 2H), 7.70-7.73 (m, 4H), 7.24 (d, J = 8.8 Hz, 2H), 7.22 (s, 1H), 4.63 (dd, J = 4.4, 4.4 Hz, 2H), 3.78 (dd, J = 4.4, 4.4 Hz, 2H), 3.49 (s, 2H), 3.42 (s, 3H), 2.72 (s, 6H), 2.51 (br, 8H), 2.28 (s, 3H); Mass (ESI): m/z 580.66 [M + H$^+$] |
| 80 | 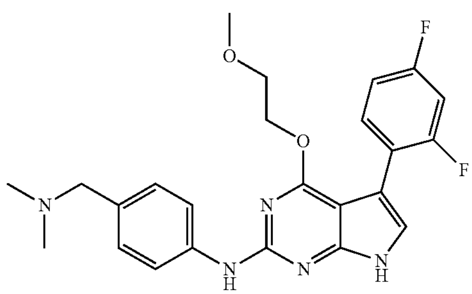 [SMILES: COCCOc1nc(Nc2ccc(CN(C)C)cc2)nc2[nH]cc(-c3ccc(F)cc3F)c12] | 5-(2,4-difluorophenyl)-N-(4-((dimethylamino)methyl)phenyl)-4-(2-methoxyethoxy)-7H-pyrrolo[2,3-d]pyrimidin-2-amine | $^1$H NMR (600 MHz, MeOD): δ (ppm) 7.90 (d, J = 8.4 Hz, 2H), 7.72 (m, 1H), 7.37 (m, 2H), 7.11 (s, 1H), 6.99 (m, 2H), 4.59 (t, J = 4.8 Hz, 2H), 4.02 (s, 2H), 3.73 (t, J = 4.8 Hz, 2H), 3.36 (s, 3H), 2.69 (s, 6H); Mass (ESI): m/z 454.27 [M + H$^+$] |
| 81 | 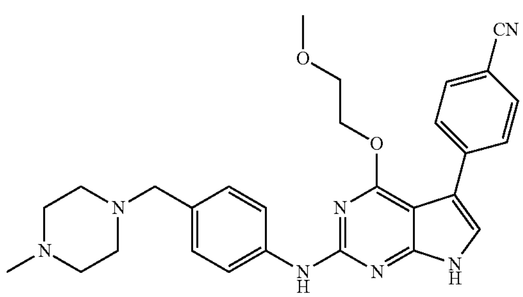 [SMILES: COCCOc1nc(Nc2ccc(CN3CCN(C)CC3)cc2)nc2[nH]cc(-c3ccc(C#N)cc3)c12] | 4-(4-(2-methoxyethoxy)-2-((4-((4-methylpiperazin-1-yl)methyl)phenyl)amino)-7H-pyrrolo[2,3-d]pyrimidin-5-yl)benzonitrile | $^1$H NMR (600 MHz, MeOD): δ (ppm) 7.96 (d, J = 8.4 Hz, 2H), 7.87 (d, J = 7.8 Hz, 2H), 7.7 (d, J = 8.4 Hz, 2H), 7.36 (d, J = 7.8 Hz, 2H), 4.67 (t, J = 4.8 Hz, 2H), 3.97 (s, 2H), 3.81 (t, J = 4.8 Hz, 2H), 3.1 (br, 8H), 2.87 (s, 2H); Mass (ESI): m/z 498.50 [M + H$^+$] |
| 82 | 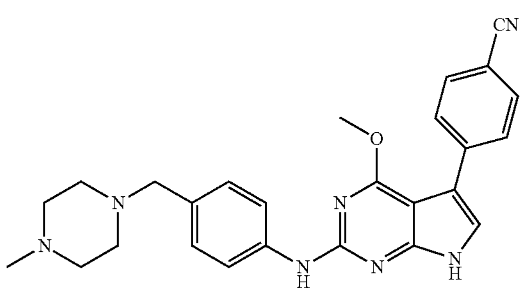 [SMILES: COc1nc(Nc2ccc(CN3CCN(C)CC3)cc2)nc2[nH]cc(-c3ccc(C#N)cc3)c12] | 4-(4-methoxy-2-((4-((4-methylpiperazin-1-yl)methyl)phenyl)amino)-7H-pyrrolo[2,3-d]pyrimidin-5-yl)benzonitrile | $^1$H NMR (600 MHz, MeOD): δ (ppm) 7.86 (d, J = 8.4 Hz, 2H), 7.81 (d, J = 8.4 Hz, 2H), 7.69 (d, J = 7.2 Hz, 2H), 7.29 (d, J = 8.4 Hz, 2H), 4.09 (s, 3H), 3.7 (s, 2H), 3.05 (br, 8H), 2.67 (s, 3H); Mass (ESI): m/z 454.18 [M + H$^+$] |
| 83 | 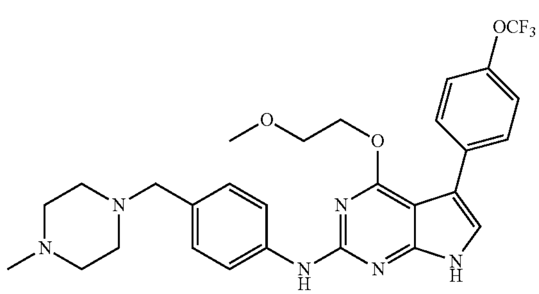 [SMILES: COCCOc1nc(Nc2ccc(CN3CCN(C)CC3)cc2)nc2[nH]cc(-c3ccc(OC(F)(F)F)cc3)c12] | 4-(2-methoxyethoxy)-N-(4-((4-methylpiperazin-1-yl)methyl)phenyl)-5-(4-(trifluoromethoxy)phenyl)-7H-pyrrolo[2,3-d]pyrimidin-2-amine | $^1$H NMR (600 MHz, MeOD): δ (ppm) 7.79 (d, J = 8.5 Hz, 2H), 7.73 (d, J = 8.5 Hz, 2H), 7.24 (d, J = 8.5 Hz, 2H), 7.22 (t, J = 8.5 Hz, 1H), 7.10 (s, 1H), 4.60 (t, J = 4.2 Hz, 2H), 3.75 (t, J = 4.2 Hz, 2H), 3.49 (s, 2H), 3.38 (s, 3H), 2.52 (br, 8H), 2.29 (s, 3H); Mass (ESI): m/z 557.5 [M + H$^+$] |

TABLE 1-continued

| Cpd | Structure | Name | Mass |
|---|---|---|---|
| 84 | 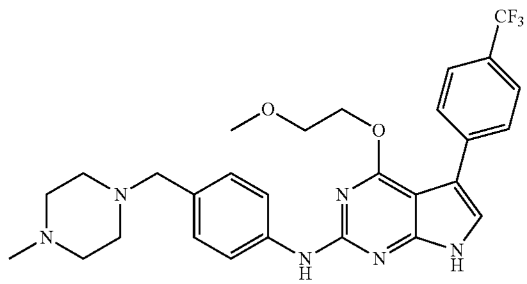 [SMILES: COCCOc1nc(Nc2ccc(CN3CCN(C)CC3)cc2)nc2[nH]cc(-c3ccc(C(F)(F)F)cc3)c12] | 4-(2-methoxyethoxy)-N-(4-((4-methylpiperazin-1-yl)methyl)phenyl)-5-(4-(trifluoromethyl)phenyl)-7H-pyrrolo[2,3-d]pyrimidin-2-amine | $^1$H NMR (600 MHz, MeOD):δ (ppm) 7.92 (d, J = 8.2 Hz, 2H), 7.74 (d, J = 8.2 Hz, 2H), 7.61 (d, J = 8.2 Hz, 2H), 7.24 (d, J = 8.2 Hz, 2H), 7.21 (s, 1H), 4.63 (d, J = 4.5 Hz, 2H), 3.77 (d, J = 4.5 Hz, 2H), 3.50 (s, 2H), 3.40 (s, 3H), 2.52 (br, 8H), 2.29 (s, 3H); Mass (ESI): m/z 541.1 [M + H$^+$] |
| 85 | 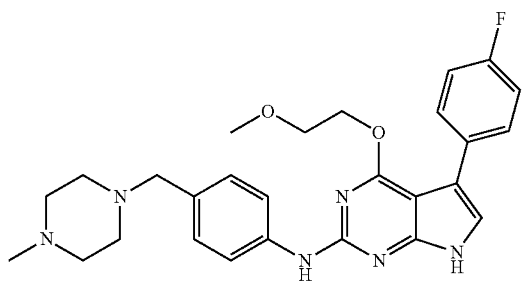 [SMILES: COCCOc1nc(Nc2ccc(CN3CCN(C)CC3)cc2)nc2[nH]cc(-c3ccc(F)cc3)c12] | 5-(4-fluorophenyl)-4-(2-methoxyethoxy)-N-(4-((4-methylpiperazin-1-yl)methyl)phenyl)-7H-pyrrolo[2,3-d]pyrimidin-2-amine | $^1$H NMR (600 MHz, CDCl$_3$): δ (ppm) 9.72 (s, 1H), 7.61 (d, J = 8.6 Hz, 1H), 7.60 (d, J = 8.6 Hz, 1H), 7.57 (d, J = 8.6 Hz, 2H), 7.24 (s, 1H), 7.23 (d, J = 8.6 Hz, 1H), 7.02 (d, J = 8.6 Hz, 1H), 7.01 (d, J = 8.6 Hz, 1H), 6.95 (s, 1H), 6.64 (s, 1H), 4.57 (d, J = 4.7 Hz, 1H), 4.56 (d, J = 5.7 Hz, 1H), 3.71 (d, J = 4.7 Hz, 1H), 3.70 (d, J = 5.7 Hz, 1H), 3.46 (s, 2H), 3.38 (s, 3H), 2.52 (br, 8H), 2.32 (s, 3H); Mass (ESI): m/z 491.26 [M + H$^+$] |
| 86 | 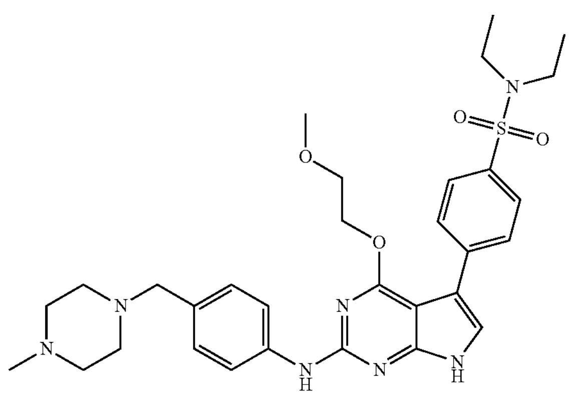 [SMILES: CCN(CC)S(=O)(=O)c1ccc(-c2c[nH]c3nc(Nc4ccc(CN5CCN(C)CC5)cc4)nc(OCCOC)c23)cc1] | N,N-diethyl-4-(4-(2-methoxyethoxy)-2-((4-((4-methylpiperazin-1-yl)methyl)phenyl)amino)-7H-pyrrolo[2,3-d]pyrimidin-5-yl)benzenesulfonamide | $^1$H NMR (600 MHz, MeOD): δ (ppm) 7.88 (d, J = 8.5 Hz, 2H), 7.74 (d, J = 8.5 Hz, 2H), 7.71 (d, J = 8.5 Hz, 2H), 7.23 (d, J = 8.5 Hz, 2H), 7.18 (s, 1H), 4.56 (d, J = 4.5 Hz, 1H), 4.55 (d, J = 4.5 Hz, 1H), 3.71 (d, J = 4.5 Hz, 1H), 3.70 (d, J = 4.5 Hz, 1H), 3.64 (s, 2H), 3.37 (s, 3H), 3.23 (q, J = 7.10 Hz, 4H), 2.77 (br, 8H), 2.66 (s, 3H), 1.12 (t, J = 7.10 Hz, 6H); Mass (ESI): m/z 608.74 [M + H$^+$] |
| 87 | 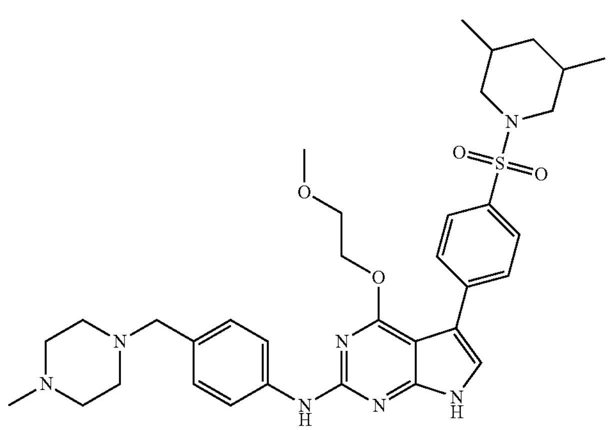 | 5-(4-((3,5-dimethylpiperidin-1-yl)sulfonyl)phenyl)-4-(2-methoxyethoxy)-N-(4-((4-methylpiperazin-1-yl)methyl)phenyl)-7H-pyrrolo[2,3-d]pyrimidin-2-amine | $^1$H NMR (600 MHz, MeOD): δ (ppm) 7.94 (d, J = 8.5 Hz, 2H), 7.72 (d, J = 8.5 Hz, 2H), 7.69 (d, J = 8.5 Hz, 2H), 7.22 (s, 1H), 7.21 (d, J = 8.5 Hz, 2H), 4.60 (d, J = 4.5 Hz, 1H), 4.59 (d, J = 4.5 Hz, 1H), 3.74 (d, J = 4.5 Hz, 1H), 3.73 (d, J = 4.5 Hz, 1H), 3.70 (dd, 1.1, 8.7 Hz, 2H), 3.47 (s, 2H), 3.39 (s, 3H), 2.49 (br, 8H), 2.26 (s, 3H), 1.69-1.78 (m, 4H), 0.86 (s, 3H), 0.85 (s, 3H), 0.45-0.52 (m, 1H); Mass (ESI): m/z 648.49 [M + H$^+$] |

TABLE 1-continued

| Cpd | Structure | Name | Mass |
|---|---|---|---|
| 88 | 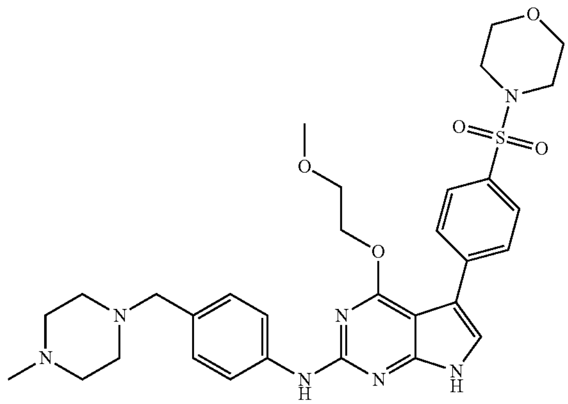 [SMILES: COCCOc1nc(Nc2ccc(CN3CCN(C)CC3)cc2)nc2[nH]cc(-c3ccc(S(=O)(=O)N4CCOCC4)cc3)c12] | 4-(2-methoxyethoxy)-N-(4-((4-methylpiperazin-1-yl)methyl)phenyl)-5-(4-(morpholinosulfonyl)phenyl)-7H-pyrrolo[2,3-d]pyrimidin-2-amine | ¹H NMR (600 MHz, CDCl₃): δ (ppm) 2.52 (s, 4H), 3.05 (t, 4H), 3.42 (d, 3H), 3.56 (d, 2H), 3.72-3.78 (m, 6H), 4.59-4.64 (m, 2H), 5.66 (s, 1H), 7.02-7.05 (m, 1H), 7.25 (d, 2H), 7.61 (d, 2H), 7.73 (d, 2H), 7.90 (d, 2H) |
| 89 | 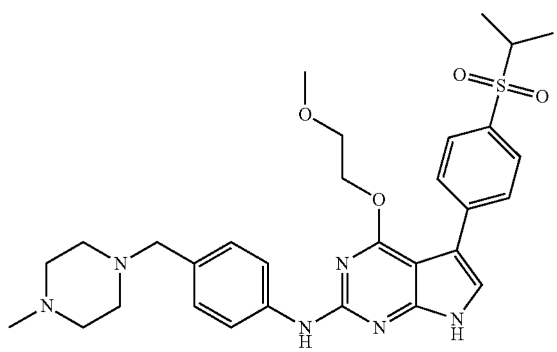 [SMILES: COCCOc1nc(Nc2ccc(CN3CCN(C)CC3)cc2)nc2[nH]cc(-c3ccc(S(=O)(=O)C(C)C)cc3)c12] | 5-(4-(isopropylsulfonyl)phenyl)-4-(2-methoxyethoxy)-N-(4-((4-methylpiperazin-1-yl)methyl)phenyl)-7H-pyrrolo[2,3-d]pyrimidin-2-amine | ¹H NMR (600 MHz, MeOD): δ (ppm) 7.95 (d, J = 8.5 Hz, 2H), 7.77 (d, J = 8.6 Hz, 2H), 7.71 (d, J = 8.5 Hz, 2H), 7.22 (s, 1H), 7.20 (d, J = 8.6 Hz, 2H), 4.56 (dd, J = 4.5, 6.0 Hz, 2H), 3.71 (d, J = 4.5, 6.0 Hz, 2H), 3.46 (s, 2H), 3.37 (s, 3H), 2.49 (br, 8H), 2.27 (s, 3H), 1.26 (s, 3H), 1.25 (s, 3H); Mass (ESI): m/z 579.61 [M + H⁺] |
| 90 | 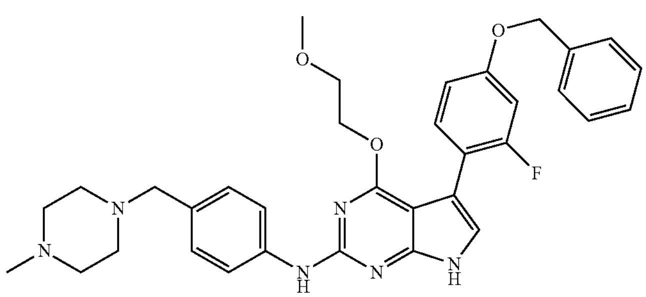 [SMILES: COCCOc1nc(Nc2ccc(CN3CCN(C)CC3)cc2)nc2[nH]cc(-c3ccc(OCc4ccccc4)cc3F)c12] | 5-(4-(benzyloxy)-2-fluorophenyl)-4-(2-methoxyethoxy)-N-(4-((4-methylpiperazin-1-yl)methyl)phenyl)-7H-pyrrolo[2,3-d]pyrimidin-2-amine | ¹H NMR (600 MHz, MeOD) δ (ppm) 7.76 (d, J = 8.5 Hz, 2H), 7.61 (t, J = 8.7 Hz, 1H), 7.48 (d, J = 7.5 Hz, 2H), 7.41 (t, J = 7.6 Hz, 2H), 7.34 (t, J = 7.4 Hz, 1H), 7.26 (d, J = 8.5 Hz, 2H), 7.02 (d, J = 1.7 Hz, 1H), 6.91-6.75 (m, 2H), 5.15 (s, 2H), 4.63 (s, 1H), 4.60-4.51 (m, 2H), 3.75-3.66 (m, 2H), 3.54 (s, 2H), 3.37 (s, 3H), 3.31 (s, 3H), 2.52 (d, J = 71.4 Hz, 7H), 2.35 (d, J = 7.5 Hz, 4H). Mass (ESI): m/z 597.47 [M + H⁺] |
| 91 | 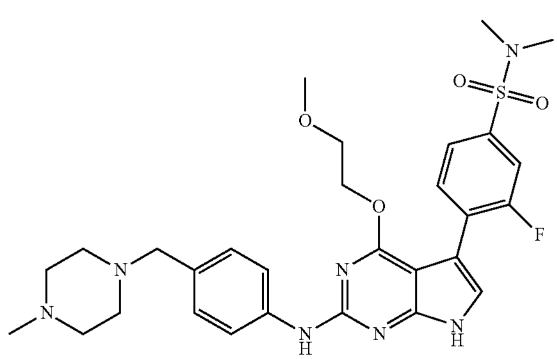 | 3-fluoro-4-(4-(2-methoxyethoxy)-2-((4-((4-methylpiperazin-1-yl)methyl)phenyl)amino)-7H-pyrrolo[2,3-d]pyrimidin-5-yl)-N,N-dimethylbenzenesulfonamide | ¹H NMR (600 MHz, MeOD): δ (ppm) 8.04 (t, J = 8.0 Hz, 1H), 7.74 (d, J = 8.5 Hz, 2H), 7.56 (dd, J = 1.8, 8.0 Hz, 1H), 7.53 (dd, J = 1.8, 8.5 Hz, 1H), 7.27 (d, J = 2.5 Hz, 1H), 7.24 (d, J = 8.5 Hz, 2H), 4.58 (dd, J = 4.7, 4.7 Hz, 2H), 3.71 (dd, J = 4.7, 4.7 Hz, 2H), 3.50 (s, 2H), 3.35 (s, 3H), 2.74 (s, 6H), 2.49 (br, 8H), 2.29 (s, 3H); Mass (ESI): m/z 598.62 [M + H⁺] |

TABLE 1-continued

| Cpd | Structure | Name | Mass |
|---|---|---|---|
| 92 | 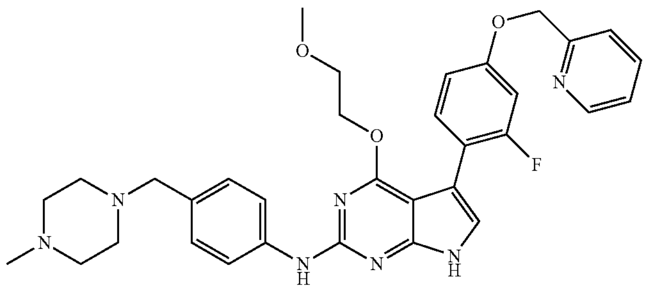 [SMILES: COCCOc1nc(Nc2ccc(CN3CCN(C)CC3)cc2)nc2[nH]cc(-c3ccc(OCc4ccccn4)cc3F)c12] | 5-(2-fluoro-4-(pyridin-2-ylmethoxy)phenyl)-4-(2-methoxyethoxy)-N-(4-((4-methylpiperazin-1-yl)methyl)phenyl)-7H-pyrrolo[2,3-d]pyrimidin-2-amine | $^1$H NMR (600 MHz, MeOD): δ (ppm) 8.56 (d, J = 4.9 Hz, 1H), 7.89 (td, J = 7.7, 1.7 Hz, 1H), 7.73 (d, J = 8.5 Hz, 2H), 7.63 (d, J = 7.7 Hz, 1H), 7.61 (d, J = 8.5 Hz, 1H), 7.39 (dd, J = 7.3, 5.2 Hz, 1H), 7.24 (d, J = 1.1 Hz, 2H), 7.01 (d, J = 1.7 Hz, 1H), 6.82-6.85 (m, 2H), 5.23 (s, 2H), 4.61 (s, 2H), 4.55 (dd, J = 4.7, 4.7 Hz, 2H), 3.68 (dd, J = 4.7, 4.7 Hz, 2H), 3.50 (s, 2H), 3.30 (s, 3H), 2.49 (br, 8H), 2.29 (s, 3H); Mass (ESI): m/z 598.40 [M + H$^+$] |
| 93 | 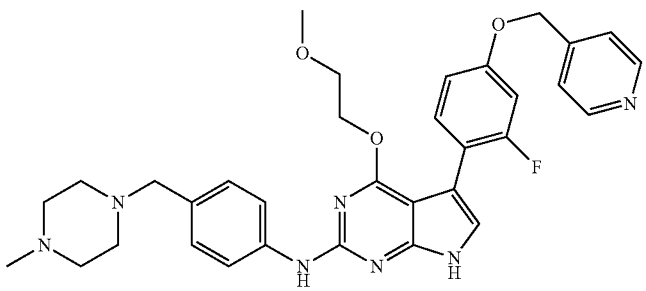 [SMILES: COCCOc1nc(Nc2ccc(CN3CCN(C)CC3)cc2)nc2[nH]cc(-c3ccc(OCc4ccncc4)cc3F)c12] | 5-(2-fluoro-4-(pyridin-4-ylmethoxy)phenyl)-4-(2-methoxyethoxy)-N-(4-((4-methylpiperazin-1-yl)methyl)phenyl)-7H-pyrrolo[2,3-d]pyrimidin-2-amine | $^1$H NMR (600 MHz, MeOD): δ (ppm) 8.56 (d, J = 4.8 Hz, 2H), 7.74 (d, J = 8.3 Hz, 2H), 7.62 (d, J = 5.7 Hz, 2H), 7.56 (dd, J = 7.7, 8.3 Hz, 1H), 7.24 (d, J = 8.7 Hz, 2H), 7.00 (d, J = 1.6 Hz, 1H), 6.77 (dd, J = 1.4, 8.7 Hz, 2H), 5.16 (s, 2H), 4.50 (dd, J = 4.3, 4.6 Hz, 2H), 3.76 (s, 2H), 3.65 (dd, J = 4.3, 4.6 Hz, 2H), 3.27 (s, 3H), 3.19 (br, 4H), 2.90 (br, 4H), 2.75 (s, 3H); Mass (ESI): m/z 598.49 [M + H$^+$] |
| 94 | 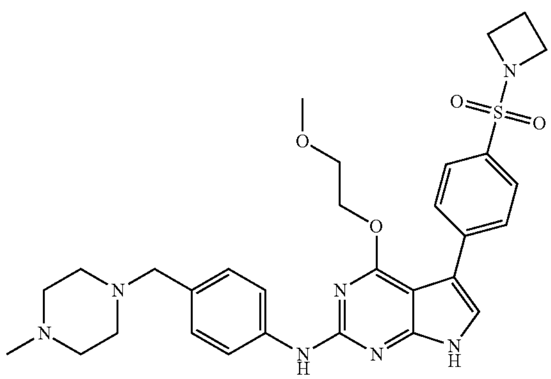 [SMILES: COCCOc1nc(Nc2ccc(CN3CCN(C)CC3)cc2)nc2[nH]cc(-c3ccc(S(=O)(=O)N4CCC4)cc3)c12] | 5-(4-(azetidin-1-ylsulfonyl)phenyl)-4-(2-methoxyethoxy)-N-(4-((4-methylpiperazin-1-yl)methyl)phenyl)-7H-pyrrolo[2,3-d]pyrimidin-2-amine | $^1$H NMR (600 MHz, MeOD/CDCl$_3$): δ (ppm) 7.95 (d, J = 8.8 Hz, 2H), 7.71-7.74 (m, 4H), 7.25 (d, J = 8.8 Hz, 2H), 7.22 (s, 1H), 4.62 (dd, J = 4.5, 4.4 Hz, 2H), 3.79 (dd, J = 4.5, 4.4 Hz, 2H), 3.52-3.56 (m, 4H), 3.46 (s, 2H), 3.42 (s, 3H), 2.51 (br, 8H), 2.29 (s, 3H), 2.21-2.24 (m, 2H); Mass (ESI): m/z 592.70 [M + H$^+$] |
| 95 | 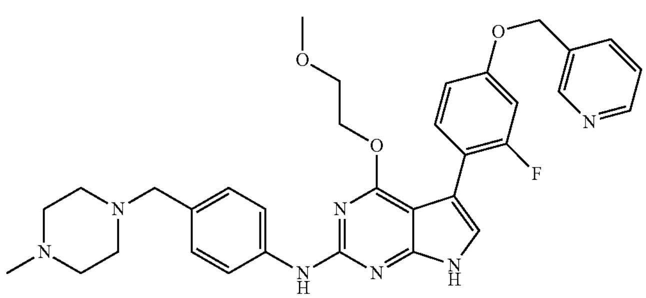 [SMILES: COCCOc1nc(Nc2ccc(CN3CCN(C)CC3)cc2)nc2[nH]cc(-c3ccc(OCc4cccnc4)cc3F)c12] | 5-(2-fluoro-4-(pyridin-3-ylmethoxy)phenyl)-4-(2-methoxyethoxy)-N-(4-((4-methylpiperazin-1-yl)methyl)phenyl)-7H-pyrrolo[2,3-d]pyrimidin-2-amine | $^1$H NMR (600 MHz, MeOD) δ (ppm) 8.69 (s, 1H), 8.55 (d, J = 4.9 Hz, 1H), 8.00 (s, 1H), 7.77 (d, J = 8.5 Hz, 2H), 7.64 (t, J = 8.7 Hz, 1H), 7.52 (s, 1H), 7.27 (d, J = 7.9 Hz, 2H), 7.04 (s, 1H), 6.87 (d, J = 10.2 Hz, 2H), 5.22 (s, 2H), 4.58 (s, 2H), 3.84-3.68 (m, 2H), 3.62 (d, J = 38.4 Hz, 2H), 3.40-3.35 (m, 2H), 2.69 (s, 8H), 2.44 (s, 3H). Mass (ESI): m/z 598.47 [M + H$^+$] |
| 96 | 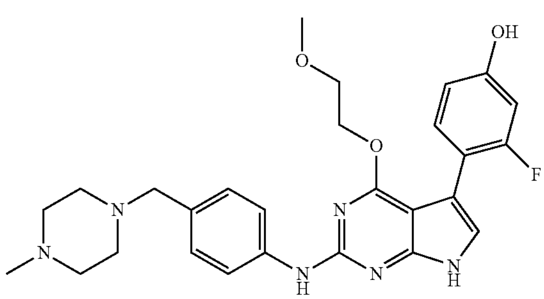 [SMILES: COCCOc1nc(Nc2ccc(CN3CCN(C)CC3)cc2)nc2[nH]cc(-c3ccc(O)cc3F)c12] | 3-fluoro-4-(4-(2-methoxyethoxy)-2-((4-((4-methylpiperazin-1-yl)methyl)phenyl)amino)-7H-pyrrolo[2,3-d]pyrimidin-5-yl)phenol | $^1$H NMR (500 MHz, MeOD): δ (ppm) 7.70 (d, J = 8.7 Hz, 2H), 7.47 (t, J = 8.7 Hz, 1H), 7.22 (d, J = 8.7 Hz, 2H), 6.95 (d, J = 1.9 Hz, 1H), 6.61 (dd, J = 2.3, 8.3 Hz, 1H), 6.55 (dd, J = 2.3, 12.0 Hz, 1H), 4.54 (dd, J = 4.6, 4.8 Hz, 2H), 3.71 (dd, J = 4.6, 4.8 Hz, 2H), 3.52 (s, 2H), 3.33 (s, 3H), 2.58 (br, 8H), 2.34 (s, 3H); Mass (ESI): m/z [M + H$^+$] |

TABLE 1-continued

| Cpd | Structure | Name | Mass |
|---|---|---|---|
| 97 | 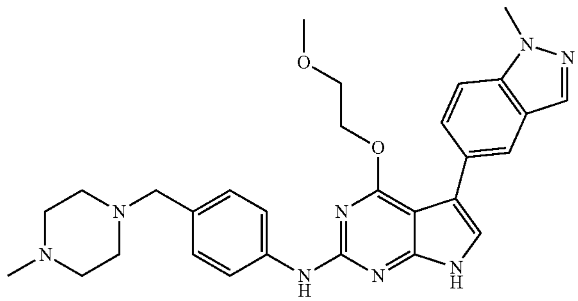 [SMILES: COCCOc1nc(Nc2ccc(CN3CCN(C)CC3)cc2)nc2[nH]cc(-c3ccc4c(cnn4C)c3)c12] | 4-(2-methoxyethoxy)-5-(1-methyl-7H-indazol-5-yl)-N-(4-((4-methylpiperazin-1-yl)methyl)phenyl)-7H-pyrrolo[2,3-d]pyrimidin-2-amine | $^1$H NMR (500 MHz, MeOD): δ (ppm) 8.06-8.07 (m, 1H), 7.97 (d, J = 0.7 Hz, 1H), 7.78 (dd, J = 1.7, 8.7 Hz, 1H), 7.72 (td, J = 1.7, 8.5 Hz, 2H), 7.47 (d, J = 8.7 Hz, 1H), 7.23 (td, J = 1.7, 8.5 Hz, 2H), 7.04 (s, 1H), 4.61 (dd, J = 4.7, 4.7 Hz, 2H), 4.07 (s, 3H), 3.75 (dd, J = 4.7, 4.7 Hz, 2H), 3.49 (s, 2H), 3.34 (s, 3H), 2.51 (br, 8H), 2.28 (s, 3H); Mass (ESI): m/z 527.55 [M + H$^+$] |
| 98 | 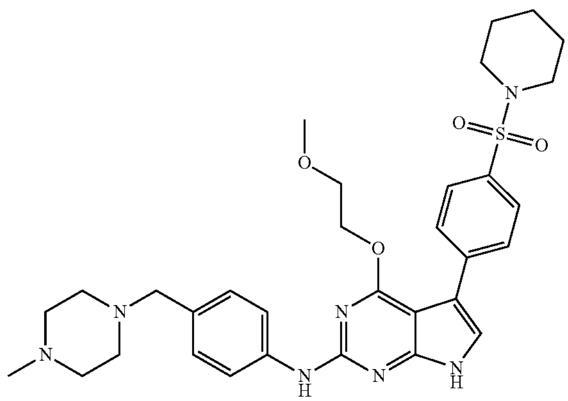 [SMILES: COCCOc1nc(Nc2ccc(CN3CCN(C)CC3)cc2)nc2[nH]cc(-c3ccc(S(=O)(=O)N4CCCCC4)cc3)c12] | 4-(2-methoxyethoxy)-N-(4-((4-methylpiperazin-1-yl)methyl)phenyl)-5-(4-(piperidin-1-ylsulfonyl)phenyl)-7H-pyrrolo[2,3-d]pyrimidin-2-amine | $^1$H NMR (500 MHz, MeOD): δ (ppm) 7.95 (dd, J = 1.7, 8.0 Hz, 2H), 7.70 (d, J = 1.7, 8.0 Hz, 4H), 7.23 (d, J = 8.4 Hz, 2H), 7.19-7.20 (m, 1H), 4.63 (dd, J = 4.6, 4.8 Hz, 2H), 3.77 (dd, J = 4.6, 4.8 Hz, 2H), 3.49 (s, 2H), 3.41 (s, 3H), 3.01 (dd, J = 5.2, 5.6 Hz, 4H), 2.51 (br, 8H), 2.28 (s, 3H), 1.63-1.67 (m, 4H), 1.42-1.47 (m, 2H); Mass (ESI): m/z 620.60 [M + H$^+$] |
| 99 | 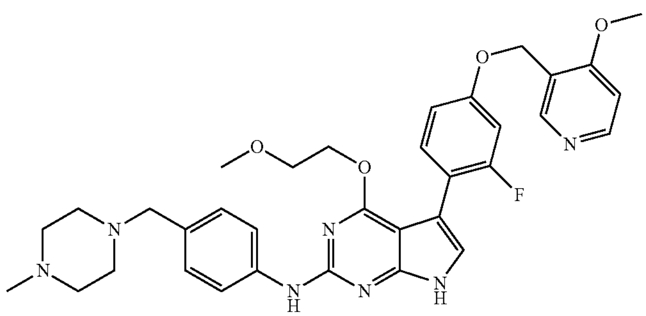 | 5-(2-fluoro-4-((4-methoxypyridin-3-yl)methoxy)phenyl)-4-(2-methoxyethoxy)-N-(4-((4-methylpiperazin-1-yl)methyl)phenyl)-7H-pyrrolo[2,3-d]pyrimidin-2-amine | $^1$H NMR (600 MHz, MeOD) δ (ppm) 8.48 (s, 1H), 8.46 (d, J = 5.7 Hz, 1H), 7.79 (d, J = 8.2 Hz, 2H), 7.64 (dd, J = 11.3, 6.7 Hz, 1H), 7.29 (d, J = 8.4 Hz, 2H), 7.17 (d, J = 5.8 Hz, 1H), 7.05 (d, J = 1.7 Hz, 1H), 6.85 (dd, J = 13.3, 4.6 Hz, 2H), 5.19 (s, 2H), 4.60-4.55 (m, 3H), 4.02 (d, J = 4.7 Hz, 3H), 3.77-3.69 (m, 2H), 3.66 (s, 2H), 2.88 (s, 8H), 2.56 (s, 3H). Mass (ESI): m/z 628.27 [M + H$^+$] |
| 100 | 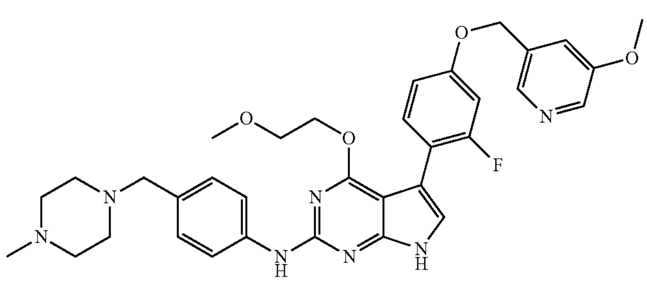 | 5-(2-fluoro-4-((5-methoxypyridin-3-yl)methoxy)phenyl)-4-(2-methoxyethoxy)-N-(4-((4-methylpiperazin-1-yl)methyl)phenyl)-7H-pyrrolo[2,3-d]pyrimidin-2-amine | $^1$H NMR (600 MHz, MeOD) δ (ppm) 8.25 (dd, J = 24.0, 2.2 Hz, 2H), 7.78-7.74 (m, 1H), 7.68-7.58 (m, 1H), 7.56 (dd, J = 2.6, 1.8 Hz, 1H), 7.27 (d, J = 6.7 Hz, 1H), 7.04 (d, J = 1.9 Hz, 1H), 6.87 (dq, J = 6.4, 2.6 Hz, 2H), 5.51 (s, 1H), 5.22 (s, 2H), 4.63 (s, 4H), 4.61-4.54 (m, 2H), 3.94 (d, J = 3.2 Hz, 3H), 3.74-3.64 (m, 2H), 3.64-3.50 (m, 2H), 3.14 (ddd, J = 333.5, 167.8, 166.4 Hz, 8H), 2.41 (s, 3H). Mass (ESI): m/z 628.64 [M + H$^+$] |

TABLE 1-continued

| Cpd | Structure | Name | Mass |
|---|---|---|---|
| 101 | 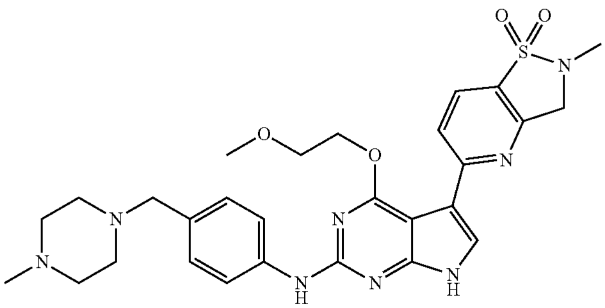 | 5-(4-(2-methoxyethoxy)-2-((4-((4-methylpiperazin-1-yl)methyl)phenyl)amino)-7H-pyrrolo[2,3-d]pyrimidin-5-yl)-2-methyl-2,3-dihydroisothiazolo[4,5-b]pyridine 1,1-dioxide | ¹H NMR (600 MHz, MeOD) δ (ppm) 7.95 (dd, J = 8.2, 1.3 Hz, 1H), 7.92 (s, 1H), 7.77 (d, J = 8.5 Hz, 2H), 7.73 (d, J = 8.2 Hz, 1H), 7.29 (s, 1H), 7.27 (d, J = 8.5 Hz, 2H), 5.51 (s, 1H), 4.69-4.59 (m, 4H), 4.42 (s, 2H), 3.82-3.74 (m, 2H), 3.58 (s, 2H), 3.42 (s, 3H), 3.37 (s, 1H), 2.94 (s, 3H), 2.67 (s, 7H), 2.42 (s, 3H). Mass (ESI): m/z 578.50 [M + H⁺] |
| 102 | 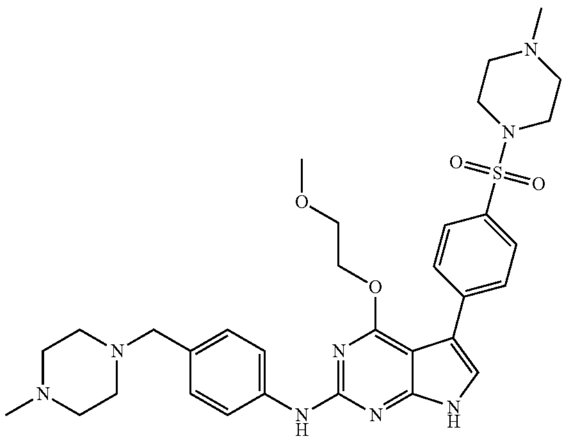 [SMILES: COCCOc1nc(Nc2ccc(CN3CCN(C)CC3)cc2)nc2[nH]cc(-c3ccc(S(=O)(=O)N4CCN(C)CC4)cc3)c12] | 4-(2-methoxyethoxy)-N-(4-((4-methylpiperazin-1-yl)methyl)phenyl)-5-(4-((4-methylpiperazin-1-yl)sulfonyl)phenyl)-7H-pyrrolo[2,3-d]pyrimidin-2-amine | ¹H NMR (500 MHz, MeOD): δ (ppm) 7.96-7.98 (m, 2H), 7.71 (d, J = 8.5 Hz, 4H), 7.24 (d, J = 8.5 Hz, 2H), 7.21-7.22 (m, 1H), 4.64 (dd, J = 4.5, 5.0 Hz, 2H), 3.78 (dd, J = 4.5, 5.0 Hz, 2H), 3.49 (s, 2H), 3.42 (s, 3H), 3.08 (br, 4H), 2.53 (br, 8H), 2.52 (t, J = 4.5 Hz, 4H), 2.28 (s, 3H), 2.27 (s, 3H); Mass (ESI): m/z 635.67 [M + H⁺] |
| 103 | 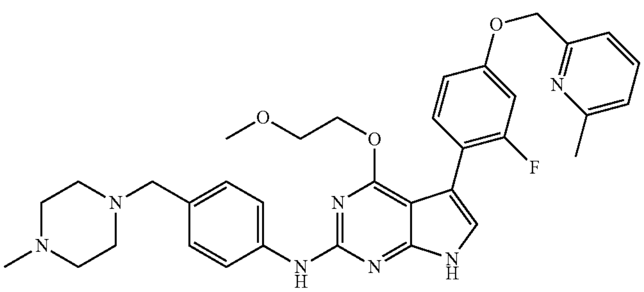 [SMILES: COCCOc1nc(Nc2ccc(CN3CCN(C)CC3)cc2)nc2[nH]cc(-c3ccc(OCc4cccc(C)n4)cc3F)c12] | 5-(2-fluoro-4-((6-methylpyridin-2-yl)methoxy)phenyl)-4-(2-methoxyethoxy)-N-(4-((4-methylpiperazin-1-yl)methyl)phenyl)-7H-pyrrolo[2,3-d]pyrimidin-2-amine | ¹H NMR (600 MHz, CDCl₃) δ (ppm) 7.69-7.62 (m, 2H), 7.62-7.57 (m, 2H), 7.36 (d, J = 7.7 Hz, 1H), 7.28 (d, J = 2.4 Hz, 1H), 7.27 (dd, J = 8.4, 2.2 Hz, 2H), 7.12 (d, J = 7.6 Hz, 1H), 6.99 (d, J = 10.6 Hz, 1H), 6.90-6.84 (m, 1H), 6.84-6.76 (m, 2H), 5.32 (s, 2H), 5.20 (d, J = 20.6 Hz, 2H), 4.65-4.50 (m, 2H), 3.70 (dd, J = 9.1, 4.3 Hz, 2H), 3.53-3.44 (m, 3H), 3.40-3.29 (m, 3H), 2.69-2.59 (m, 4H), 2.59-2.33 (m, 6H), 2.33-2.26 (m, 4H). Mass (ESI): m/z 613.00 [M + H⁺] |
| 104 | 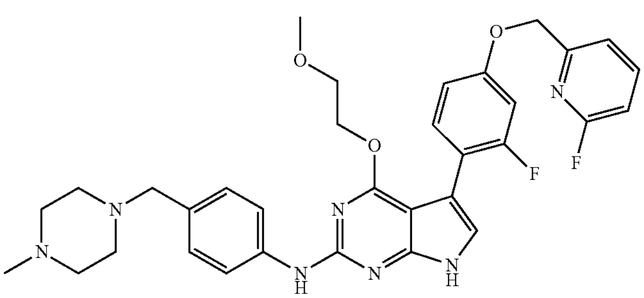 [SMILES: COCCOc1nc(Nc2ccc(CN3CCN(C)CC3)cc2)nc2[nH]cc(-c3ccc(OCc4cccc(F)n4)cc3F)c12] | 5-(2-fluoro-4-((6-fluoropyridin-2-yl)methoxy)phenyl)-4-(2-methoxyethoxy)-N-(4-((4-methylpiperazin-1-yl)methyl)phenyl)-7H-pyrrolo[2,3-d]pyrimidin-2-amine | ¹H NMR (600 MHz, MeOD): δ (ppm) 7.85 (q, J = 8.0 Hz, 1H), 7.67 (d, J = 9.0 Hz, 2H), 7.55 (t, J = 9.0 Hz, 1H), 7.37 (dd, J = 1.5, 7.0 Hz, 1H), 7.15 (dd, J = 8.5 Hz, 2H), 6.93 (d, J = 2.1 Hz, 1H), 6.92 (dd, J = 2.1, 8.3 Hz, 1H), 6.70-6.75 (m, 2H), 5.02 (s, 2H), 4.46 (dd, J = 4.6, 4.8 Hz, 2H), 3.60 (dd, J = 4.6, 4.8 Hz, 2H), 3.39 (s, 2H), 3.25 (s, 3H), 2.45 (br, 8H), 2.21 (s, 3H); Mass (ESI): m/z 616.40 [M + H⁺] |

TABLE 1-continued

| Cpd | Structure | Name | Mass |
|---|---|---|---|
| 105 | 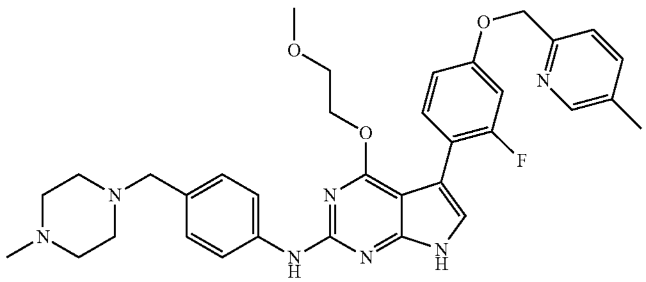 | 5-(2-fluoro-4-((5-methylpyridin-2-yl)methoxy)phenyl)-4-(2-methoxyethoxy)-N-(4-((4-methylpiperazin-1-yl)methyl)phenyl)-7H-pyrrolo[2,3-d]pyrimidin-2-amine | $^1$H NMR (600 MHz, MeOD): δ (ppm) 8.36-8.37 (m, 1H), 7.68 (d, J = 8.6 Hz, 2H), 7.67 (dd, J = 2.3, 8.6 Hz, 1H), 7.60 (t, J = 8.6 Hz, 1H), 7.48 (d, J = 8.0 Hz, 1H), 7.22 (d, J = 8.5 Hz, 2H), 6.99 (d, J = 1.8 Hz, 1H), 6.76-6.80 (m, 2H), 5.15 (s, 2H), 4.54 (dd, J = 4.6, 4.8 Hz, 2H), 3.68 (dd, J = 4.6, 4.8 Hz, 2H), 3.48 (s, 2H), 3.30 (s, 3H), 2.49 (br, 8H), 2.36 (s, 3H), 2.27 (s, 3H); Mass (ESI): m/z 612.78 [M + H$^+$] |
| 106 | 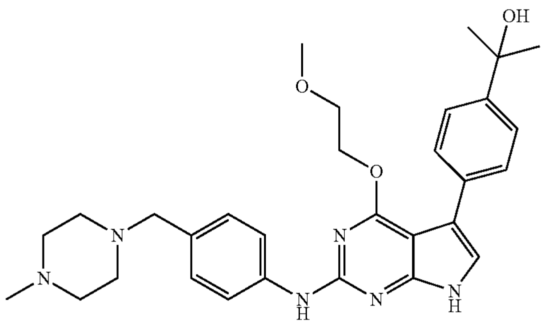 [SMILES: COCCOc1nc(Nc2ccc(CN3CCN(C)CC3)cc2)nc2[nH]cc(-c3ccc(C(C)(C)O)cc3)c12] | 2-(4-(4-(2-methoxyethoxy)-2-((4-((4-methylpiperazin-1-yl)methyl)phenyl)amino)-7H-pyrrolo[2,3-d]pyrimidin-5-yl)phenyl)propan-2-ol | $^1$H NMR (600 MHz, MeOD): δ (ppm) 7.67 (d, J = 8.7 Hz, 2H), 7.63 (d, J = 8.4 Hz, 2H), 7.42 (d, J = 8.4 Hz, 2H), 7.13 (d, J = 8.7 Hz, 2H), 6.93 (s, 1H), 4.52 (dd, J = 4.5, 4.9 Hz, 2H), 3.67 (dd, J = 4.5, 4.9 Hz, 2H), 3.37 (s, 2H), 3.34 (s, 3H), 2.41 (br, 8H), 2.19 (s, 3H), 1.54 (s, 6H); Mass (ESI): m/z 531.79 [M + H$^+$] |
| 107 | 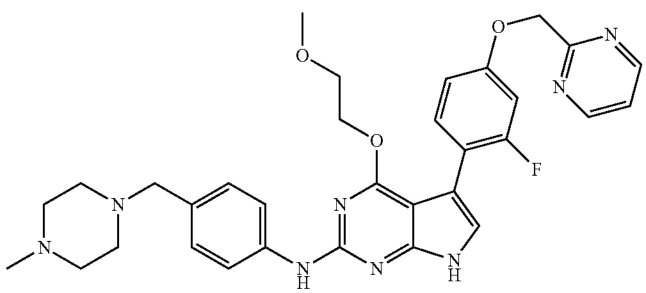 [SMILES: COCCOc1nc(Nc2ccc(CN3CCN(C)CC3)cc2)nc2[nH]cc(-c3ccc(OCc4ncccn4)cc3F)c12] | 5-(2-fluoro-4-(pyrimidin-2-ylmethoxy)phenyl)-4-(2-methoxyethoxy)-N-(4-((4-methylpiperazin-1-yl)methyl)phenyl)-7H-pyrrolo[2,3-d]pyrimidin-2-amine | $^1$H NMR (600 MHz, MeOD): δ (ppm) 8.82 (dd, J = 1.0, 5.0 Hz, 2H), 7.66-7.69 (m, 2H), 7.60 (dd, J = 8.6, 9.0 Hz, 1H), 7.42-7.45 (m, 1H), 7.22 (d, J = 8.4 Hz, 2H), 6.99 (d, J = 2.0 Hz, 1H), 6.79-6.84 (m, 2H), 5.31 (s, 2H), 4.55 (dd, J = 4.6, 4.9 Hz, 2H), 3.69 (dd, J = 4.6, 4.9 Hz, 2H), 3.49 (s, 2H), 2.52 (br, 8H), 2.28 (s, 3H); Mass (ESI): m/z 599.56 [M + H$^+$] |
| 108 | 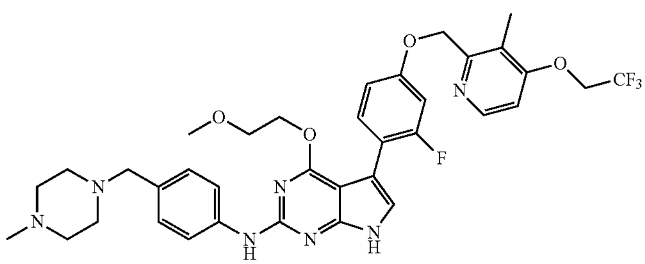 [SMILES: COCCOc1nc(Nc2ccc(CN3CCN(C)CC3)cc2)nc2[nH]cc(-c3ccc(OCc4nccc(OCC(F)(F)F)c4C)cc3F)c12] | 5-(2-fluoro-4-((3-methyl-4-(2,2,2-trifluoroethoxy)pyridin-2-yl)methoxy)phenyl)-4-(2-methoxyethoxy)-N-(4-((4-methyipiperazin-1-yl)methyl)phenyl)-7H-pyrrolo[2,3-d]pyrimidin-2-amine | $^1$H NMR (500 MHz, MeOD) δ (ppm) 8.36 (d, J = 6.1 Hz, 1H), 7.77 (dd, J = 20.1, 8.6 Hz, 2H), 7.62 (t, J = 8.9 Hz, 1H), 7.27 (t, J = 9.4 Hz, 2H), 7.12 (d, J = 5.8 Hz, 1H), 7.03 (d, J = 1.9 Hz, 1H), 6.92-6.82 (m, 2H), 5.27 (s, 2H), 4.75 (dd, J = 16.7, 8.3 Hz, 2H), 4.60-4.56 (m, 2H), 3.73-3.69 (m, 2H), 3.52 (d, J = 4.1 Hz, 2H), 2.52 (s, 7H), 2.36 (s, 3H), 2.30 (s, 3H). Mass (ESI): m/z 710.44 [M + H$^+$] |
| 109 | 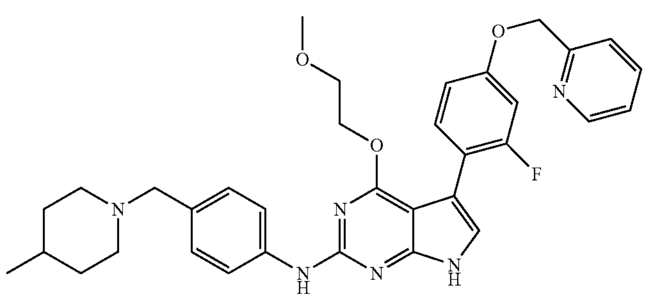 [SMILES: COCCOc1nc(Nc2ccc(CN3CCC(C)CC3)cc2)nc2[nH]cc(-c3ccc(OCc4ccccn4)cc3F)c12] | 5-(2-fluoro-4-(pyridin-2-ylmethoxy)phenyl)-4-(2-methoxyethoxy)-N-(4-((4-methylpiperidin-1-yl)methyl)phenyl)-7H-pyrrolo[2,3-d]pyrimidin-2-amine | $^1$H NMR (600 MHz, MeOD): δ (ppm) 8.56-8.57 (m, 1H), 7.90 (td, J = 7.8, 1.8 Hz, 1H), 7.73 (d, J = 8.4 Hz, 2H), 7.64 (d, J = 7.8 Hz, 1H), 7.62 (d, J = 8.8 Hz, 1H), 7.38-7.41 (m, 1H), 7.24 (d, J = 8.8 Hz, 2H), 7.01 (d, J = 1.8 Hz, 1H), 6.82-6.85 (m, 2H), 5.22 (s, 2H), 4.55 (dd, J = 4.8, 4.5 Hz, 2H), 3.69 (dd, J = 4.8, 4.5 Hz, 2H), 3.51 (s, 2H), 2.93 (d, J = 11.5 Hz, 2H), 2.06 (dd, J = 11.2, 11.8 Hz, 2H), 1.65 (d, J = 11.8 Hz, 2H), 1.37-1.41 (m, 1H), 1.22-1.28 (m, 2H), 0.94 (d, J = 6.3 Hz, 3H); Mass (ESI): m/z 597.51 [M + H$^+$] |

TABLE 1-continued

| Cpd | Structure | Name | Mass |
|---|---|---|---|
| 110 | 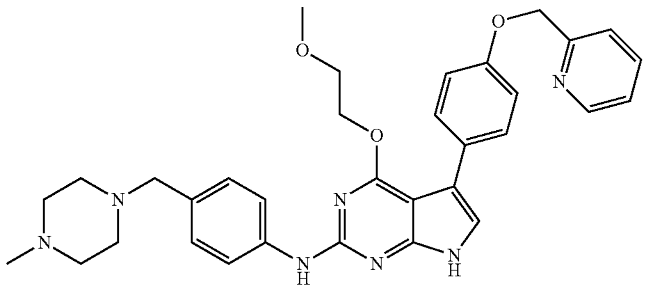 [SMILES: COCCOc1nc(Nc2ccc(CN3CCN(C)CC3)cc2)nc2[nH]cc(-c3ccc(OCc4ccccn4)cc3)c12] | 4-(2-methoxyethoxy)-N-(4-((4-methylpiperazin-1-yl)methyl)phenyl)-5-(4-(pyridin-2-ylmethoxy)phenyl)-7H-pyrrolo[2,3-d]pyrimidin-2-amine | $^1$H NMR (500 MHz, MeOD) δ (ppm) 8.58 (d, J = 5.1 Hz, 1H), 7.91 (td, J = 7.7, 1.7 Hz, 1H), 7.81 (d, J = 8.4 Hz, 2H), 7.68-7.63 (m, 2H), 7.45-7.36 (m, 1H), 7.30 (d, J = 8.4 Hz, 2H), 7.02 (dd, J = 6.3, 2.5 Hz, 2H), 5.24 (s, 2H), 4.69-4.52 (m, 5H), 3.80-3.71 (m, 2H), 3.38 (d, J = 8.1 Hz, 2H), 3.19 (s, 8H), 2.74 (s, 3H). Mass (ESI): m/z 580.40 [M + H$^+$] |
| 111 | 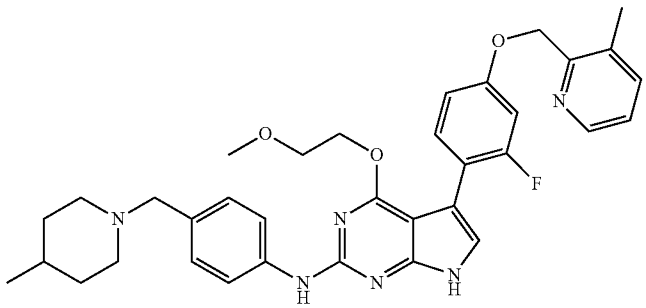 [SMILES: COCCOc1nc(Nc2ccc(CN3CCC(C)CC3)cc2)nc2[nH]cc(-c3ccc(OCc4ncccc4C)cc3F)c12] | 5-(2-fluoro-4-((3-methylpyridin-2-yl)methoxy)phenyl)-4-(2-methoxyethoxy)-N-(4-((4-methylpiperidin-1-yl)methyl)phenyl)-7H-pyrrolo[2,3-d]pyrimidin-2-amine | 1H NMR (600 MHz, MeOD) δ 8.41 (dd, J = 4.9, 1.0 Hz, 1H), 7.92 (d, J = 8.4 Hz, 2H), 7.75 (d, J = 7.7 Hz, 1H), 7.63 (dd, J = 12.1, 5.6 Hz, 1H), 7.42-7.33 (m, 3H), 7.07 (d, J = 1.8 Hz, 1H), 6.91-6.85 (m, 2H), 5.28 (d, J = 7.2 Hz, 2H), 4.61-4.54 (m, 2H), 4.15 (s, 2H), 3.79-3.66 (m, 2H), 3.40 (d, J = 15.8 Hz, 1H), 2.89 (s, 2H), 2.49 (d, J = 6.5 Hz, 3H), 1.97-1.83 (m, 2H), 1.43 (s, 2H), 1.29 (d, J = 34.5 Hz, 2H), 1.03 (d, J = 6.5 Hz, 3H). Mass (ESI): m/z 611.84 [M + H$^+$] |
| 112 | 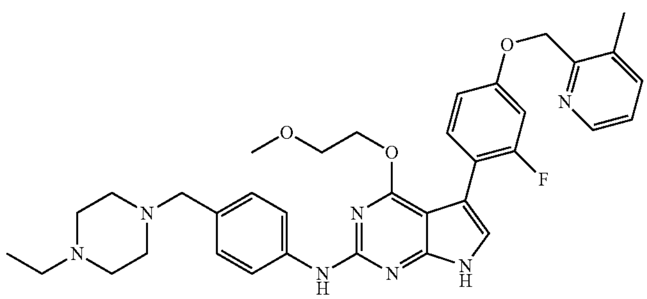 [SMILES: CCN1CCN(Cc2ccc(Nc3nc(OCCOC)c4c(-c5ccc(OCc6ncccc6C)cc5F)c[nH]c4n3)cc2)CC1] | N-(4-((4-ethylpiperazin-1-yl)methyl)phenyl)-5-(2-fluoro-4-((3-methylpyridin-2-yl)methoxy)phenyl)-4-(2-methoxyethoxy)-7H-pyrrolo[2,3-d]pyrimidin-2-amine | 1H NMR (600 MHz, MeOD) δ 8.42-8.35 (m, 1H), 7.80 (dd, J = 15.2, 8.5 Hz, 2H), 7.71 (d, J = 7.5 Hz, 1H), 7.61 (t, J = 8.6 Hz, 1H), 7.38-7.32 (m, 1H), 7.27 (d, J = 8.4 Hz, 2H), 7.03 (d, J = 1.6 Hz, 1H), 6.86 (d, J = 10.1 Hz, 2H), 5.24 (d, J = 6.1 Hz, 2H), 4.55 (dd, J = 5.2, 3.8 Hz, 2H), 3.70 (dd, J = 5.4, 3.7 Hz, 4H), 3.32-3.29 (m, 3H), 3.05 (s, 8H), 2.51-2.36 (m, 3H). Mass (ESI): m/z 626.72 [M + H$^+$] |

Described below are the procedures used to synthesize the above-described 112 exemplary compounds.

Unless otherwise stated, all starting materials used were commercially available and used as supplied. Reactions requiring anhydrous conditions were performed in flame-dried glassware and cooled under an argon or nitrogen atmosphere. Unless otherwise stated; reactions were carried out under argon or nitrogen and monitored by analytical thin-layer chromatography performed on glass-backed plates (5 cm×10 cm) precoated with silica gel 60 F254 as supplied by Merck. Visualization of the resulting chromatograms was done by looking under an ultraviolet lamp (λ=254 nm), followed by dipping in an nBuOH solution of Ninhydrin (0.3% w/v) containing acetic acid (3% v/v) or ethanol solution of phosphomolybdic acid (2.5% w/v) and charring by heat gun. Solvents for reactions were dried under an argon or nitrogen atmosphere prior to use as follows: THF, Toluene, and DCM were dried by the column of Dried molecular Sieve 5A (LC technology solution Inc). and DMF from calcium hydride or anhydrous with commercially available. Flash chromatography was used routinely for purification and separation of product mixtures using RediSep Rf Silica Gel Disposable Flash Columns, Gold® 20-40/40-60 microns silica gel and Reusable RediSep Rf Gold® C18 Reversed Phase columns, 20-40 microns supplied by RediSep. Eluent systems are given in volume/volume concentrations. $^{13}$C and $^1$H NMR spectra were recorded on Bruker AVIII (400 MHz). Chloroform-d or dimethyl sulfoxide-dr and CD$_3$OD was used as the solvent and TMS (δ 0.00 ppm) as an internal standard. Chemical shift values are reported in ppm relative to the TMS in delta (δ) units. Multiplicities are recorded as s (singlet), br s (broad singlet), d (doublet), t (triplet), q (quartet), dd (doublet of doublet), dt (doublet of triplet), m (multiplet). Coupling constants (J) are expressed in Hz. Electrospray mass spectra (ESMS) were recorded using a Thermo LTQ XL mass spectrometer. Spectral data were recorded as m/z values.

Shown below is the synthetic scheme followed for synthesizing the compounds of formula (I).

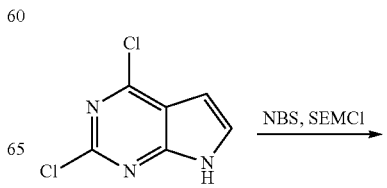

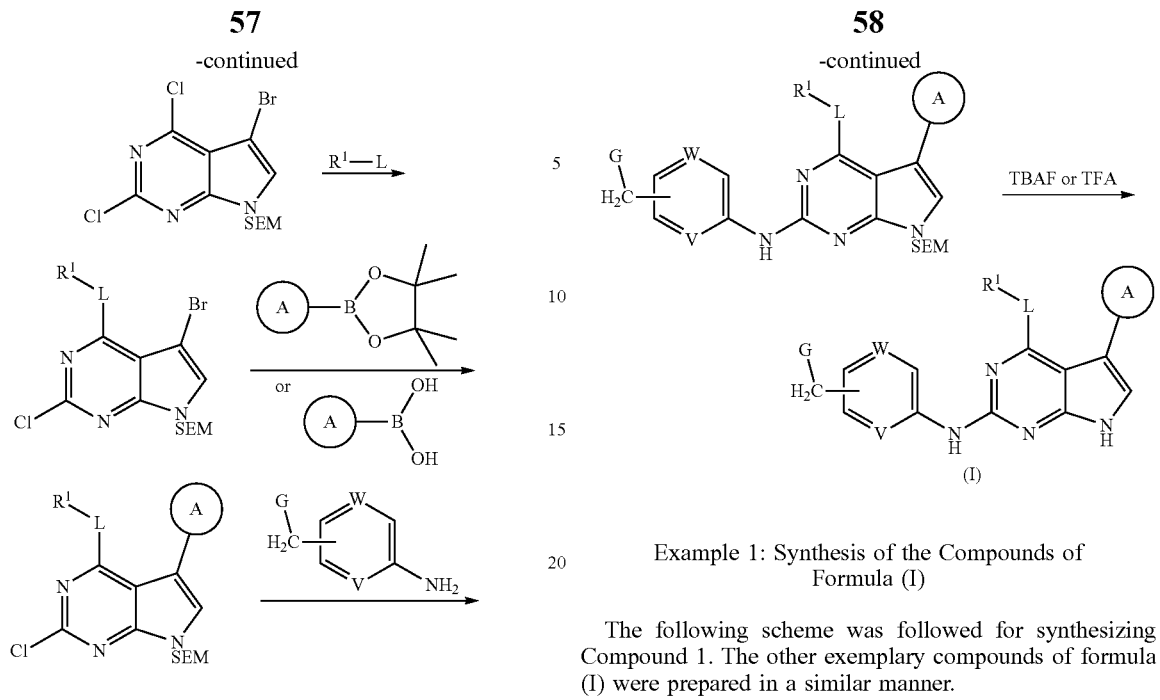
Example 1: Synthesis of the Compounds of Formula (I)
The following scheme was followed for synthesizing Compound 1. The other exemplary compounds of formula (I) were prepared in a similar manner.
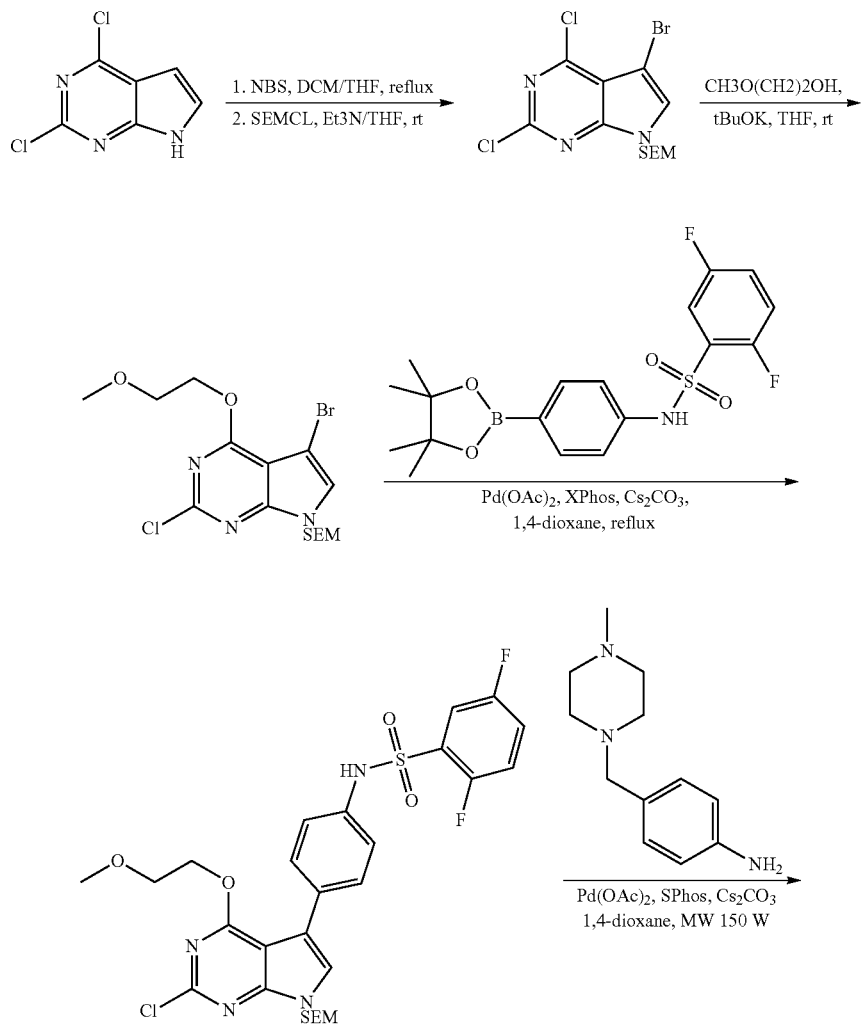

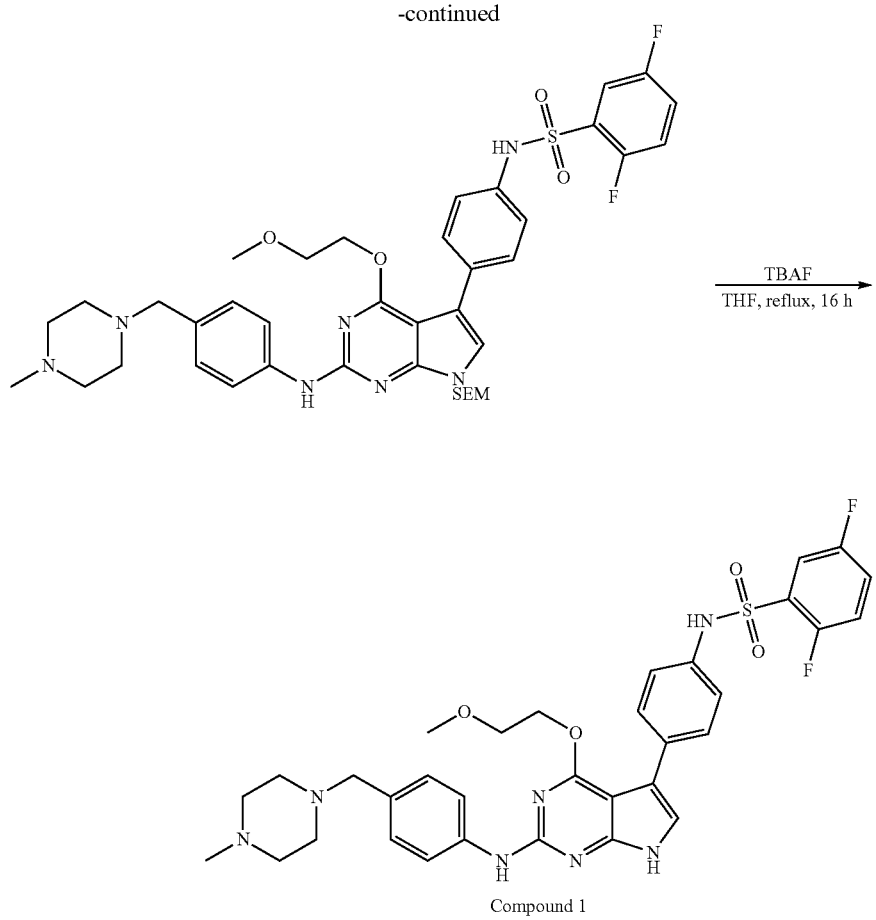

Compound 1

Step Synthesis of 5-bromo-2,4-dichloro-7-((2-(trimethylsilyl)ethoxy)methyl)-7H-pyrrolo-[2,3-d]pyrimidine

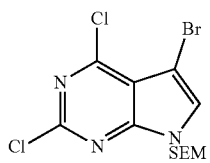 [SMILES: C[Si](C)(C)CCOCn1cc(Br)c2c(Cl)nc(Cl)nc21]

To a suspension of 2, 6-dichloro-7-deazapurine (3760 mg, 20 mmol) in $CH_2Cl_2$ (50 mL) at room temperature, N-bromosuccinimide (4270 mg, 24 mmol) was added. The mixture was stirred at reflux for 2 h, and then $CH_2Cl_2$ was removed. The residue was partitioned between water and EtOAc. The organic phase was separated, washed with $NaHC_3$ (aq.), dried over $Na_2SO_4$ and concentrated under vacuum to give the intermediate.

To a suspension of potassium tert-butoxide (4488 mg, 40 mmol) in THF (50 mL) was added into the intermediate at 0° C. The resulting mixture was stirred for 30 min before 2-(trimethylsilyl)ethoxymethyl chloride (5002 mg, 30 mmol) was added. The mixture was then warmed up to room temperature and stirred for 2 h. Water was added to quench the reaction. Extraction with ethyl acetate followed by drying combined organic layers with $Na_2SO_4$, concentrated, and purified by silica gel column chromatography using EtOAc and hexane gradient eluents to obtain the 5-bromo-2,4-dichloro-7-((2-(trimethylsilyl)ethoxy)-methyl)-7H-pyrrolo[2,3-d]pyrimidine in 76% yield as a colorless solid. $^1$H NM/R (500 MHz, $CDCl_3$): δ 7.41 (s, 1H), 5.57 (s, 2H), 3.53 (t, J=8.3 Hz, 2H), 0.92 (t, J=8.3 Hz, 2H), 0.03 (s, 9H); Mass (ESI) m/z 396.19 [M+H$^+$].

Step 2: Synthesis of 5-bromo-2-chloro-4-(2-methoxyethoxy)-7-((2-(trimethylsilyl)ethoxy)methyl)-7H-pyrrolo[2,3-d]pyrimidine

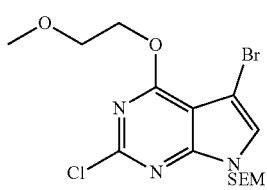 [SMILES: COCCOc1nc(Cl)nc2c1c(Br)cn2COCC[Si](C)(C)C]

To a suspension of potassium tert-butoxide (1306 mg, 11.6 mmol in dry THF 10 mL) under nitrogen atmosphere was added a solution of 2-methoxyethanol (487 mg, 6.4 mmol) at 0° C. The reaction mixture was stirred at rt for 30 min before a solution of 5-bromo-2,4-dichloro-7-((2-(trimethylsilyl)ethoxy)methyl)-7H-pyrrolo[2,3-d]pyrimidine (2311 mg, 5.8 mmol in dry THF 5 mL) was added and the resulting reaction mixture was stirred at room temperature for 2 h. After the reaction was complete, water was added to quench the reaction. The organic solvent was removed under vacuum and the aqueous layer was extracted with ethyl acetate. The combined organic layers were washed with brine, dried over anhydrous sodium sulfate, and filtered. The filtrate was evaporated under reduced pressure. The product was purified by silica gel column chromatography using EtOAc and hexane gradient eluents to obtain 5-bromo-2-chloro-4-(2-methoxyethoxy)-7-((2-(trimethylsilyl)ethoxy)methyl)-7H-pyrrolo[2,3-d]pyrimidine in 61% yield as a pale yellow oil. $^1$H NMR (500 MHz, CDCl$_3$): δ 7.17 (s, 1H), 5.51 (s, 2H), 4.69 (t, J=4.5 Hz, 2H), 3.84 (t, J=4.5 Hz, 2H), 3.51 (d, J=8.0 Hz, 2H), 3.48 (s, 3H), 0.91 (t, J=8.0 Hz, 2H), −0.04 (s, 9H); Mass (ESI) m/z 436.38 [M+H$^+$].

Step 3: Synthesis of N-(4-(2-chloro-4-(2-methoxyethoxy)-7-((2-(trimethylsilyl)ethoxy)methyl)-7H-pyrrolo[2,3-d]pyrimidin-5-yl)phenyl)-2,5-difluorobenzenesulfonamide 7H-pyrrolo[2,3-d]pyrimidin-5-yl)phenyl)-2,5-difluorobenzene sulfonamide in 26% yield as a pale yellow oil. $^1$H NMR (500 MHz, CDCl$_3$): δ 7.59 (d, J=8.5 Hz, 2H), 7.56-7.58 (m, 1H), 7.17-7.23 (m, 3H), 7.15 (d, J=8.5 Hz, 2H), 7.00 (s, 1H), 5.57 (s, 2H), 4.62 (t, J=4.5 Hz, 2H), 3.68 (t, J=4.5 Hz, 2H), 3.54 (t, J=8.2 Hz, 2H), 3.37 (s, 3H), 0.92 (t, J=8.2 Hz, 2H), −0.05 (s, 9H); Mass (ESI) m/z 625.53 [M+H$^+$].

Step 4: Synthesis of 2,5-difluoro-N-(4-(4-(2-methoxyethoxy)-2-((4-((4-methylpiperazin-1-yl)methyl)phenyl)amino)-7-((2-(trimethylsilyl)ethoxy)methyl)-7H-pyrrolo[2,3-d]pyrimidin-5-yl)phenyl) benzenesulfonamide

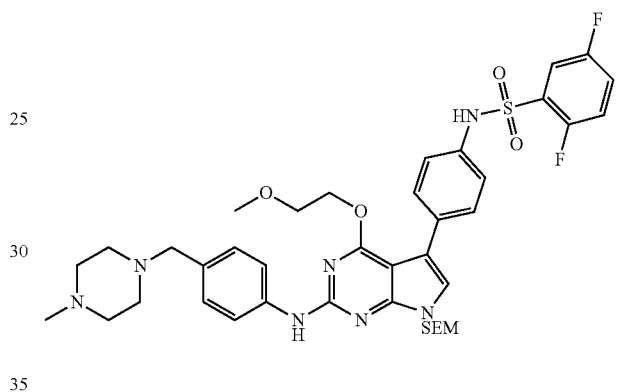

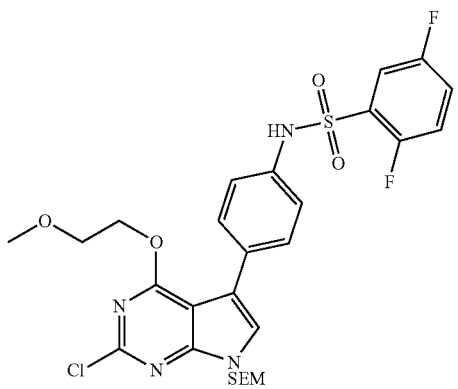 [SMILES: COCCOc1nc(Cl)nc2c1c(-c1ccc(NS(=O)(=O)c3cc(F)ccc3F)cc1)cn2COCC[Si](C)(C)C]

To a degassed solution of 5-bromo-2-chloro-4-(2-methoxyethoxy)-7-((2-(trimethylsilyl)ethoxy)methyl)-7H-pyrrolo[2,3-d]pyrimidine (437 mg, 1.0 mmol) in 1,4-dioxane was added (4-((2,5-difluorophenyl)sulfonamido)phenyl) boronic acid pinacol ester (435 mg, 1.1 mmol), palladium(II) acetate (5 mg, 0.02 mmol), XPhos (19 mg, 0.04 mmol), and cesium carbonate (977 mg, 3.0 mmol). The mixture was heated to reflux until the starting material disappeared. The organic solvent was removed under vacuum and the aqueous layer was extracted with ethyl acetate. The combined organic layers were washed with brine, dried over anhydrous sodium sulfate, and filtered. The filtrate was evaporated under reduced pressure. The product was purified by silica gel column chromatography using EtOAc and hexane gradient eluents to give N-(4-(2-chloro-4-(2-methoxyethoxy)-7-((2-(trimethylsilyl)ethoxy)methyl)-

To a degassed solution of N-(4-(2-chloro-4-(2-methoxyethoxy)-7-((2-(trimethylsilyl)ethoxy)methyl)-7H-pyrrolo[2,3-d]pyrimidin-5-yl)phenyl)-2,5-difluorobenzene sulfonamide (140 mg, 0.224 mmol in 1,4-dioxane) was added 4-((4-methylpiperazin-1-yl)methyl)aniline (51 mg, 0.246 mmol), palladium(II) acetate (1 mg, 0.004 mmol), SPhos (3 mg, 0.008 mmol) and cesium carbonate (146 mg, 0.448 mmol). The mixture was heated under microwave irradiation at 150 W for 20 min. The organic solvent was removed under vacuum and the aqueous layer was extracted with ethyl acetate. The combined organic layers were washed with brine, dried over anhydrous sodium sulfate, and filtered. The filtrate was evaporated under reduced pressure. The product was purified by silica gel column chromatography using dichloromethane and methanol gradient eluents to give 2,5-difluoro-N-(4-(4-(2-methoxyethoxy)-2-((4-((4-methylpiperazin-1-yl)methyl)phenyl)amino)-7-((2-(trimethylsilyl)ethoxy)methyl)-7H-pyrrolo[2,3-d]pyrimidin-5-yl)phenyl)benzenesulfonamide in 41% yield as a pale yellow solid. $^1$H NMR (500 MHz, CDCl$_3$): δ 7.63 (d, J=8.5 Hz, 2H), 7.61 (d, J=8.3 Hz, 2H), 7.53-7.57 (m, 1H), 7.25 (d, J=8.3 Hz, 2H), 7.14-7.21 (m, 2H), 7.11 (d, J=8.5 Hz, 2H), 6.96 (s, 2H), 5.51 (s, 2H), 4.55 (t, J=4.6 Hz, 2H), 3.69 (t, J=4.6 Hz, 2H), 3.56 (t, J=8.3 Hz, 2H), 3.47 (s, 2H), 3.37 (s, 3H), 2.48 (br, 8H), 2.29 (s, 3H), 0.92 (t, J=8.3 Hz, 2H), −0.09 (s, 9H); Mass (ESI) m/z 794.58, 397.79 [M+H$^+$].

Step 5: Synthesis of 2, 5-difluoro-N-(4-(4-(2-methoxyethoxy)-2-((4-((4-methylpiperazin-1-yl)methyl)phenyl)amino)-7H-pyrrolo[2,3-d]pyrimidin-5-yl)phenyl)benzenesulfonamide

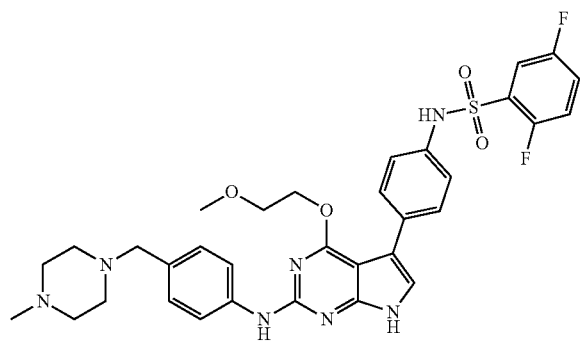 [SMILES: COCCOc1nc(Nc2ccc(CN3CCN(C)CC3)cc2)nc2[nH]cc(-c3ccc(NS(=O)(=O)c4cc(F)ccc4F)cc3)c12]

To a solution of 2,5-difluoro-N-(4-(4-(2-methoxyethoxy)-2-((4-((4-methylpiperazin-1-yl)methyl)phenyl)amino)-7-((2-(trimethylsilyl)ethoxy)methyl)-7H-pyrrolo[2,3-d]pyrimidin-5-yl)phenyl)benzenesulfonamide (43 mg, 0.054 mmol) and tetrabutylammonium fluoride (0.54 mL, 1M in THF) in THF was heated to reflux until the starting material disappeared. The organic solvent was removed under vacuum and the residue was poured into 1N NaOH(aq), then extracted with ethyl acetate. The combined organic layers were washed with brine, dried over anhydrous sodium sulfate and filtered. The filtrate was evaporated under reduced pressure. The product was purified by silica gel column chromatography using dichloromethane and methanol gradient eluents to give 2, 5-difluoro-N-(4-(4-(2-methoxyethoxy)-2-((4-((4-methylpiperazin-1-yl)methyl)phenyl)amino)-7H-pyrrolo[2,3-d]pyrimidin-5-yl)phenyl)benzenesulfonamide in 33% yield as a white solid. $^1$H NMR (500 MHz, MeOD): δ 7.69 (d, J=8.5 Hz, 2H), 7.58 (d, J=8.5 Hz, 2H), 7.54-7.57 (m, 1H), 7.30-7.37 (m, 2H), 7.20 (d, J=8.5 Hz, 2H), 7.12 (d, J=8.5 Hz, 2H), 6.98 (s, 1H), 4.54 (t, J=4.5 Hz, 2H), 3.69 (t, J=4.5 Hz, 2H), 3.47 (s, 2H), 3.34 (s, 3H), 2.50 (br, 8H), 2.28 (s, 3H); Mass (ESI) m/z 664.31 [M+H$^+$].

Example 2: Evaluation of Inhibition Activity of Compounds of Formula (I) in In Vitro Assays The compounds prepared in EXAMPLE 1 were tested in the in vitro RTK assays described below.

Axl Kinase Assay

Certain compounds of formula (I) were tested for their potency in inhibiting Axl kinase. Inhibition of Axl kinase activity by a test compound was calculated by AlphaScreen (PerkinElmer 6760620M). Standard assay conditions included 1 ng of recombinant Axl kinase (SignalChem) with 3-10 ng Poly-(GT)-Biotin (Cisbio) in the assay buffer, i.e., 40 μM ATP (Sigma), 10 mM MOPs, pH7.0 (Sigma M-1254), 0.21 mM EDTA (Sigma E-6758), 0.5% glycerol (J. T Baker 2136-1), 1 mg/ml BSA (Bio-Rad 500-0007), 0.01% 2-mercaptoethanol (BDH 441433A), and 0.001% Brij35 (Sigma P1254) in a final volume of 25 μL. Reactions were incubated at 30° C. for 30 minutes and stopped by adding 5 μL of 50 mM EDTA. Product analysis was performed using the AlphaScreen kit and counted with Enspire Alpha (PerkinElmer). Screen values of inhibitors were determined after carrying out assays with eight serially diluted concentrations in duplication. Results were analyzed using linear regression software (GraphPad Prism 4; GraphPad Software Inc.).

Mer Kinase Assay

Certain compounds of formula (I) were tested for their potency in inhibiting Mer kinase. Inhibition of Mer kinase activity by a test compound was calculated by AlphaScreen (PerkinElmer 6760620M). Standard assay conditions included 2 ng of recombinant Mer kinase (SignalChem) with 5 ng Poly-(GT)-Biotin (Cisbio) in the assay buffer, i.e., 10 μM ATP (Sigma), 8 mM MOPs, pH7.0 (Sigma M-1254), 0.2 mM EDTA (Sigma E-6758), 0.5% glycerol (J. T Baker 2136-1), 0.1 mg/ml BSA (Bio-Rad 500-0007), 0.01% 2-mercaptoethanol (BDH 441433A), 0.001% Brij35 (Sigma P1254), 10 mM MgCl$_2$, and 10 mM MnCl$_2$ in a final volume of 25 μL. Reactions were incubated at 30° C. for 30 minutes and stopped by adding 5 μL of 50 mM EDTA. Product analysis was performed using the AlphaScreen kit and counted with Enspire Alpha (PerkinElmer). Screen values of inhibitors were determined after carrying out assays with each compound at serially diluted concentrations in duplication. Results were analyzed using linear regression software (GraphPad Prism 4; GraphPad Software Inc.).

Met Kinase Assay

Certain compounds of formula (I) were tested for their potency in inhibiting Met kinase. Inhibition of Met kinase activity by a test compound was calculated by AlphaScreen (PerkinElmer 6760620M). Standard assay conditions included 1 ng of recombinant Mer kinase (SignalChem) with 3 ng Poly-(GT)-Biotin (Cisbio) in the assay buffer, i.e., 10 μM ATP (Sigma), 8 mM MOPs, pH7.0 (Sigma M-1254), 0.2 mM EDTA (Sigma E-6758), 0.5% glycerol (J. T Baker 2136-1), 0.1 mg/ml BSA (Bio-Rad 500-0007), 0.01% 2-mercaptoethanol (BDH 441433A), 0.001% Brij35 (Sigma P1254), 10 mM MgCl$_2$, and 10 mM MnCl$_2$ in a final volume of 25 μL. Reactions were incubated at 30° C. for 30 minutes and stopped by adding 5 μL of 50 mM EDTA. Product analysis was performed using the AlphaScreen kit and counted with Enspire Alpha (PerkinElmer). Screen values of inhibitors were determined after carrying out assays with each compound at serially diluted concentrations in duplication. Results were analyzed using linear regression software (GraphPad Prism 4; GraphPad Software Inc.).

Results

In comparison with Met kinase inhibition activity, the test compounds were found to preferentially inhibit the activities of both Axl kinase and Mer kinase to various degrees as indicated by their IC$_{50}$ values (IC$_{50}$ being the concentration of an inhibitor where the response or binding is reduced by half). See Table 2 below.

More specifically, 89 of 112 inventive compounds show the IC$_{50}$ value below 100 nM for Axl kinase and 22 of 112 inventive compounds show the IC$_{50}$ value below 100 nM for Mer kinase, including IC$_{50}$ values below 30 nM represented by activity level "A", IC$_{50}$ values between 30 nM and 100 nM represented by activity level "B", IC$_{50}$ values between 100 nM and 400 nM represented by activity level "C", IC$_{50}$ values between 400 nM and 1 μM represented by activity level "D", and IC50 values >1 μM represented by activity level "E".

TABLE 2

| Compound | Kinase Activity | | |
|---|---|---|---|
| | Axl kinase IC$_{50}$ (nM) | Mer kinase IC$_{50}$ (nM) | Met kinase IC$_{50}$ (nM) |
| 1 | A | B | D |
| 2 | A | A | C |
| 3 | A | C | E |
| 4 | A | B | D |
| 5 | A | C | E |
| 6 | C | E | E |
| 7 | C | E | E |
| 8 | C | D | E |
| 9 | A | C | D |
| 10 | C | C | E |
| 11 | A | C | D |
| 12 | C | B | E |
| 13 | B | B | D |
| 14 | B | C | D |
| 15 | C | D | E |
| 16 | B | C | E |
| 17 | A | D | E |
| 18 | B | D | E |
| 19 | A | C | E |
| 20 | B | E | E |
| 21 | B | D | E |
| 22 | B | D | E |
| 23 | C | C | E |
| 24 | B | C | D |
| 25 | A | C | E |
| 26 | B | E | E |
| 27 | B | C | E |
| 28 | A | B | C |
| 29 | C | B | D |
| 30 | A | B | E |
| 31 | C | C | D |
| 32 | B | C | D |
| 33 | B | C | D |
| 34 | A | B | E |
| 35 | B | C | E |
| 36 | B | B | D |
| 37 | B | B | C |
| 38 | A | C | E |
| 39 | A | C | E |
| 40 | C | C | E |
| 41 | B | C | E |
| 42 | B | C | E |
| 43 | B | C | E |
| 44 | C | E | D |
| 45 | A | C | D |
| 46 | B | E | E |
| 47 | C | D | E |
| 48 | A | B | D |
| 49 | B | D | E |
| 50 | A | B | E |
| 51 | B | C | D |
| 52 | A | C | E |
| 53 | A | B | E |
| 54 | A | B | D |
| 55 | A | C | D |
| 56 | C | C | D |
| 57 | B | C | E |
| 58 | B | C | D |
| 59 | A | C | D |
| 60 | B | C | E |
| 61 | C | D | E |
| 62 | B | C | E |
| 63 | A | C | D |
| 64 | A | C | E |
| 65 | B | D | E |
| 66 | B | D | E |
| 67 | A | E | E |
| 68 | A | B | E |
| 69 | A | B | D |
| 70 | C | D | E |
| 71 | B | B | D |
| 72 | C | C | E |
| 73 | C | C | E |
| 74 | B | B | D |
| 75 | A | B | E |
| 76 | A | E | E |
| 77 | A | C | D |
| 78 | C | D | E |
| 79 | A | C | E |
| 80 | A | C | D |
| 81 | B | D | E |
| 82 | B | D | E |
| 83 | B | D | E |
| 84 | C | E | E |
| 85 | A | C | E |
| 86 | C | E | E |
| 87 | C | E | C |
| 88 | C | E | E |
| 89 | C | E | E |
| 90 | B | E | D |
| 91 | A | C | E |
| 92 | A | C | D |
| 93 | A | E | E |
| 94 | A | E | E |
| 95 | A | E | E |
| 96 | A | A | C |
| 97 | A | D | E |
| 98 | A | E | D |
| 99 | B | E | E |
| 100 | A | E | E |
| 101 | A | E | E |
| 102 | B | E | E |
| 103 | A | C | E |
| 104 | A | C | E |
| 105 | A | D | E |
| 106 | B | C | E |
| 107 | A | C | E |
| 108 | B | C | D |
| 109 | A | A | D |
| 110 | A | C | D |
| 111 | A | C | D |
| 112 | A | C | D |

These results show that compounds of formula (I) are selective and exhibit high potencies in inhibiting the activities of both Axl and Mer kinases. The selectivities of compounds of formula (I) for TAM kinases are unexpected and would make these compounds useful therapeutics for TAM kinases-associated diseases.

Example 3: Comparison of the Potency of a Compound of Formula (I) with a Structurally Close Compounds in the Prior Art Compound 25 and Compound 22 were selected to compare its in vitro potencies with the potencies of compounds Example A and Example B found in the prior art.

As shown in Table 3, Compound 25 and Compound 22 are almost identical in structure to Example A and Example B, respectively, except that Compound 25 and compound 22 each have a substituted amino group attached to a phenyl via a methylene group instead of via a carbonyl group as in Example A and Example B.

TABLE 3

Comparison of in vitro potency of the inventive compounds with the compounds covered in the prior art

| Compound | Structure | Axl kinase IC$_{50}$ (nM) |
|---|---|---|
| Example A (Known compound in the prior art) | *(structure)* | 156 |
| Compound 25 | *(structure)* | 22 |
| Example B (Compound covered in the prior art) | *(structure)* | 213 |
| Compound 22 | *(structure)* | 46 |

Unexpectedly, it was observed that Compound 25 and Compound 22 exhibited superior potencies, as compared to the prior art compounds Example A and Example B, in inhibiting Axl kinase with 5 fold or more.

Example 4: Evaluation of the Cellular Potencies of Compounds of Formula (I) in Growth Arrest Specific 6 (Gas6) Ligand Induced AKT Phosphorylation Gas6/TAM has important roles in the development of multiple types of cancer, including AML, ALL, schwannoma, glioma, thyroid carcinoma, ovarian carcinoma, lung cancer, gastric cancer, prostate cancer, renal cell carcinoma, breast cancer and melanoma. In general, Gas6/TAM promotes cancer advancement, and the expression of Gas6 and TAM consistently predicts poor prognosis. Wu et al., *Cell Death & Disease*, vol. 8, page e2700 (2017).

The potent compounds selected in EXAMPLE 2 were tested in Gas6 ligand induced AKT phosphorylation via western blotting assay. For western blotting experiments, H1299 NSCLC cells were cultured in serum free RPMI-1640 medium and culture overnight. On the assay day, two hundred thousand cells were pretreated with compound for 2 hours in 6-well plate, then stimulated by 100 ng/mL Gas6 ligand for 30 mins. Whole cell lysate was harvested by adding 2×SDS Sample Buffer. Proteins were separated by SDS-PAGE electrophoresis and transfer to PVDF membrane. Protein expression was detected using immunoblot with various primary antibodies and secondary antibodies following standard protocol. Antibody against p-AKT (Ser473) and anti-rabbit IgG, HRP-linked secondary antibodies were purchased from Cell Signaling Technology. Antibody against actin was purchased from Millipore. Immunoblots were revealed by chemiluminescence (SuperSignal™ West Femto Maximum Sensitivity Substrate, Thermo) and detected by ChemiDoc™ MP Imaging System (Bio-Rad). Band intensity of western blot was also quantified by ChemiDoc MP Imaging System. Relative intensity of bands corresponding to drug treatment were compared to the ligand alone group. The percentage (%) inhibition at each drug concentration was calculated using the formula:

Percentage (%) inhibition=(1−Relative intensity)× 100.

The selected compounds of formula I exhibited more than 50% inhibition activity against Gas6 ligand induced AKT phosphorylation at 100 nM treatment were listed in following Table 4.

TABLE 4

| Inhibition of Gas6 ligand induced AKT phosphorylation | |
|---|---|
| Compound with >50% inhibition activity against Gas6 ligand induced AKT phosphorylation (at 100 nM treatment) | Compound 1, 5, 9, 11, 19, 25, 34, 39, 45, 50, 52, 53, 54, 59, 64, 67, 68, 75, 76, 79, 92, 93, 107, 109, 110, 111, 112 |

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

Further, from the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A compound of formula (I):

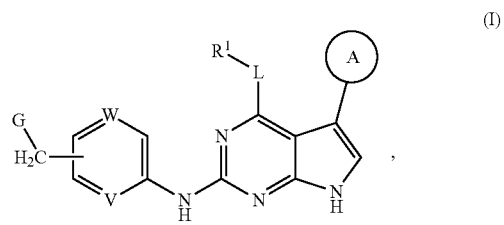

or a tautomer, stereoisomer, isotopologue, or pharmaceutically acceptable salt thereof,
wherein
$R^1$ is H, $C_{1-8}$ alkyl, $C_{3-8}$ cycloalkyl, $C_{3-8}$ heterocyclyl, aryl, or heteroaryl; wherein
L is O, S, NH, or aryl;
Ring A is

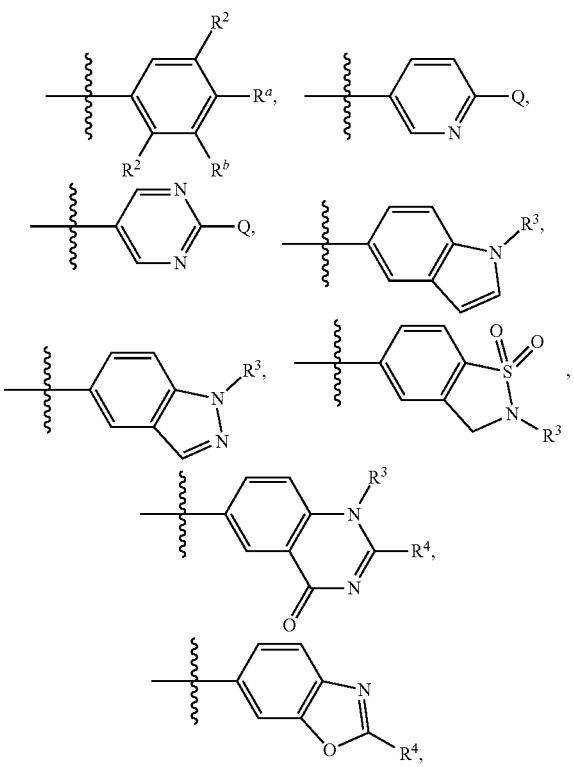

wherein one of $R^a$ and $R^b$ is Q and the other $R^a$ and $R^b$ is $R^2$;
Q is H, halogen, $OR^5$, $OCH_2Ar$, CN, $N_3$, $NO_2$, $N(R^5)(R^6)$, $N(R^5)CO(R^7)$, $C(O)R^5$, $C(O)OR^5$, $C(O)N(R^5)(R^6)$, $SO_2R^5$, $SO_2N(R^5)(R^6)$, $SOR^5$, $SR^5$, $NR^5SO_2R^7$, $C_{1-8}$ alkyl, $C_{2-8}$ alkenyl, $C_{2-8}$ alkynyl, $C_{3-8}$ cycloalkyl, $C_{1-8}$ heterocyclyl, aryl, or heteroaryl, in which each of $R^5$, $R^6$, and $R^7$, independently, is H, $C_{1-8}$ alkyl, $C_{3-8}$ cycloalkyl, $C_{3-8}$ heterocyclyl, aryl, or heteroaryl, or, $R^5$ and $R^6$, together with the atom to which they are attached, form $C_{3-8}$ cycloalkyl, $C_{3-8}$ heterocyclyl; and Ar is selected from benzodioxanyl, indazolyl, isoquinolinyl, isoxazolyl, naphthyl, oxadiazolyl, phenyl, pyridinyl, pyrimidinyl, pyridinonyl, and quinolinyl; wherein each ring is optionally substituted with 1, 2, 3, or 4 substituents independently selected from $C_1$-$C_4$ alkoxy, $C_1$-$C_4$ alkoxycarbonyl, $C_1$-$C_4$ alkoxycarbonylamino, $C_1$-$C_4$ alkyl, ($C_1$-$C_4$ alkyl)carbonyl, ($C_1$-$C_4$ alkyl)sulfonyl, amido, aminocarbonyl, aminocarbonyl($C_1$-$C_3$ alkyl), —(CH$_2$)$_q$CO$_2$ $C_1$-$C_4$ alkyl, —(CH$_2$)$_q$OH, carboxy, cyano, formyl, halo, halo $C_1$-$C_4$ alkyl, halo $C_1$-$C_4$ alkoxy, nitro, phenyl optionally substituted with one cyano group, phenyloxy optionally substituted with one halo group, phenylcarbonyl, pyrrole, and tetrahydropyran; and wherein q is 0, 1, 2, 3, or 4;

each of the $C_{1-8}$ alkyl, $C_{2-8}$ alkenyl, $C_{2-8}$ alkynyl, $C_{3-8}$ cycloalkyl, $C_{1-8}$ heterocyclyl, aryl, and heteroaryl being optionally substituted with one or more moieties selected from the group consisting of halogen, OR$^5$, CN, N$_3$, NO$_2$, N(R$^5$)(R$^6$), N(R$^5$)CO(R$^7$), C(O)R$^5$, C(O) OR$^5$, C(O)N(R$^5$)(R$^6$), SO$_2$R$^5$, SO$_2$N(R$^5$)(R$^6$), SOR$^5$, SR$^5$, NR$^5$SO2R$^7$, $C_{1-8}$ alkyl, $C_{1-8}$ alkoxyl, $C_{2-8}$ alkenyl, $C_{2-8}$ alkynyl, $C_{3-8}$ cycloalkyl, $C_{1-8}$ heterocyclyl, aryl, and heteroaryl.

each $R^2$ is independently H, halogen, OH, CH$_2$OH, CN, CF$_3$, CH$_3$, OCH$_3$, OCF$_3$, N(CH$_3$)$_2$, $R^3$ is H, $C_{1-4}$ alkyl, $C_{3-8}$ cycloalkyl, $C_{1-8}$ heterocyclyl, aryl, or heteroaryl;

$R^4$ is H, CN, $C_{1-4}$ alkyl, $C_{3-8}$ cycloalkyl, $C_{1-8}$ heterocyclyl, aryl, or heteroaryl;

each of W and V, independently, is N or CR$^8$, R$^8$ being H, halogen, OR$^5$, CN, N$_3$, NO$_2$, N(R$^5$)(R$^6$), N(R$^5$)CO(R$^7$), C(O)R$^5$, C(O)OR$^5$, C(O)N(R$^5$)(R$^6$), SO$_2$R$^5$, SO$_2$N(R$^5$)(R$^6$), SOR$^5$, SR$^6$, NR$^5$SO$_2$R$^7$, $C_{1-8}$ alkyl, $C_{2-8}$ alkenyl, $C_{2-8}$ alkynyl, $C_{3-8}$ cycloalkyl, $C_{1-8}$ heterocyclyl, aryl, or heteroaryl, in which each of R$^5$, R$^6$, and R$^7$, independently, is H, $C_{1-8}$ alkyl, $C_{3-8}$ cycloalkyl, $C_{1-8}$ heterocyclyl, aryl, or heteroaryl, or, R$^5$ and R$^6$, together with the atom to which they are attached, form $C_{3-8}$ cycloalkyl, $C_{3-8}$ heterocyclyl; and G is halogen, OR$^5$, CN, N$_3$, NO$_2$, N(R$^9$)(R$^{10}$), N(R$^5$)CO (R$^7$), C(O)R$^5$, C(O)OR$^5$, C(O)N(R$^5$)(R$^6$), SO$_2$R$^5$, SO$_2$N(R$^5$)(R$^6$), SOR$^5$, SR$^5$, NR$^5$SO$_2$R$^7$, $C_{2-8}$ alkenyl, $C_{2-8}$ alkynyl, $C_{3-8}$ cycloalkyl, $C_{3-8}$ heterocyclyl, aryl, or heteroaryl, in which each of R$^9$ and R$^{10}$, independently, is $C_{1-8}$ alkyl, $C_{3-8}$ cycloalkyl, $C_{3-8}$ heterocyclyl, aryl, or heteroaryl, or, R$^9$ and R$^{10}$, together with the atom to which they are attached, form $C_{3-8}$ heterocyclyl, each of the $C_{1-8}$ alkyl, $C_{2-8}$ alkenyl, $C_{2-8}$ alkynyl, $C_{3-8}$ cycloalkyl, $C_{3-8}$ heterocyclyl, aryl, and heteroaryl being optionally substituted with one or more moieties selected from the group consisting of halogen, OR$^5$, CN, N$_3$, NO$_2$, N(R$^5$)(R$^6$), N(R$^5$)CO(R$^7$), C(O)R$^5$, C(O)OR$^5$, C(O)N(R$^5$) (R$^6$), SO$_2$R$^5$, SO$_2$N(R$^5$)(R$^6$), SOR$^5$, SR$^5$, NR$^5$SO$_2$R$^7$, $C_{1-8}$ alkyl, $C_{1-8}$ alkoxyl, $C_{2-8}$ alkenyl, $C_{2-8}$ alkynyl, $C_{3-8}$ cycloalkyl, $C_{3-8}$ heterocyclyl, aryl, and heteroaryl.

2. The compound of claim 1, or a tautomer, stereoisomer, isotopologue, or salt thereof, wherein G is N(R$^9$)(R$^{10}$), in which each of R$^9$ and R$^{10}$, independently, is $C_{1-8}$ alkyl, $C_{3-8}$ cycloalkyl, $C_{3-8}$ heterocyclyl, aryl, or heteroaryl, or, R$^9$ and R$^{10}$, together with the atom to which they are attached, form $C_{3-8}$ heterocyclyl.

3. The compound of claim 1, or a tautomer, stereoisomer, isotopologue, or salt thereof, wherein L is O.

4. The compound of claim 2, or a tautomer, stereoisomer, isotopologue, or salt thereof, wherein G is N(R$^9$)(R$^{10}$) or $C_{3-8}$ heterocyclyl.

5. The compound of claim 4, or a tautomer, stereoisomer, isotopologue, or salt thereof, wherein G is $C_{3-8}$ heterocyclyl.

6. The compound of claim 5, or a tautomer, stereoisomer, isotopologue, or salt thereof, wherein the $C_{3-8}$ heterocyclyl is a 5- or 6-membered ring.

7. The compound of claim 6, or a tautomer, stereoisomer, isotopologue, or salt thereof, wherein G is

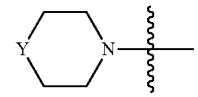

optionally substituted with one or more $C_{1-8}$ alkyl, in which Y is O, -13 NR, or —CR'R", each of R, R', and R", independently, being H, OH, NH$_2$, or $C_{1-8}$ alkyl.

8. The compound of claim 7, or a tautomer, stereoisomer, isotopologue, or salt thereof, wherein Y is —NR, R being H or $C_{1-8}$ alkyl; or Y is —CR'R", each of R' and R", independently, being H, OH, NH$_2$, or $C_{1-8}$ alkyl.

9. The compound of claim 8, or a tautomer, stereoisomer, isotopologue, or salt thereof, wherein the compound is

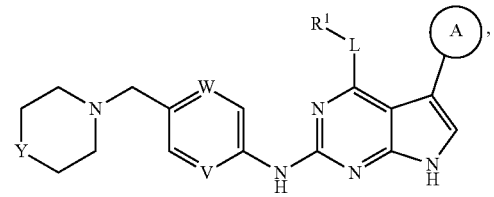

in which each of W and V, independently, is N or CR$^8$, R$^8$ being H, halogen, OR$^5$, N(R$^5$)(R$^6$), or $C_{1-8}$ alkyl.

10. The compound according to claim 1 selected from
2,5-difluoro-N-(4-(4-(2-methoxyethoxy)-2-((4-((4-methylpiperazin-1-yl)methyl) phenyl)amino)-7H-pyrrolo [2,3-d] pyrimidin-5-yl) phenyl)benzenesulfonamide;
2,5-difluoro-N-(4-(4-methoxy-2-((4-((4-methyl piperidin-1-yl) methyl)phenyl) amino)-7H-pyrrolo[2,3-d] pyrimidin-5-yl) phenyl)benzenesulfonamide;
2,5-difluoro-N-(4-(4-(2-methoxyethoxy)-2-((4-((4-methylpiperidin-1-yl)methyl) phenyl)amino)-7H-pyrrolo [2,3-d] pyrimidin-5-yl) phenyl)benzenesulfonamide;
N-(4-(4-methoxy-2-((4-((4-methylpiperidin-1-yl)methyl) phenyl)amino)-7H-pyrrolo[2,3-d]pyrimidin-5-yl)phenyl)methanesulfonamide;
4-(4-methoxy-2-((4-((4-methylpiperidin-1-yl)methyl) phenyl)amino)-7H-pyrrolo[2,3-d]pyrimidin-5-yl)-N, N-dimethylbenzenesulfonamide;
4-(2-((4-((4-aminopiperidin-1-yl)methyl)phenyl)amino)-4-methoxy-7H-pyrrolo[2,3-d]pyrimidin-5-yl)-N,N-dimethylbenzenesulfonamide;
4-(4-methoxy-2-((4-(morpholinomethyl)phenyl)amino)-7H-pyrrolo[2,3-d] pyrimidin-5-yl) -N,N-dimethylbenzenesulfonamide;
4-(2-((2-fluoro-4-((4-methylpiperidin-1-yl)methyl)phenyl)amino)-4-methoxy-7H-pyrrolo [2,3-d]pyrimidin-5-yl)-N,N-dimethylbenzenesulfonamide;

5-(2-fluoro-4-((4-methylpyridin-2-yl)methoxy)phenyl)-4-(2-methoxyethoxy)-N-(4-((4-methylpiperazin-1-yl)methyl)phenyl)-7H-pyrrolo[2,3-d]pyrimidin-2-amine;

(3-(4-methoxy-2-((4-((4-methyl piperazin-1-yl) methyl) phenyl)amino)-7H-pyrrolo[2,3-d] pyrimidin-5-yl) phenyl) methanol;

5-(2-fluoro-4-((3-methylpyridin-2-yl)methoxy)phenyl)-4-(2-methoxyethoxy)-N-(4-((4-methylpiperazin-1-yl)methyl)phenyl)-7H-pyrrolo[2,3-d]pyrimidin-2-amine;

5-(3-fluoro phenyl) -4-methoxy-N-(4-((4-methyl piperazin-1-yl) methyl)phenyl)-7H-pyrrolo[2,3-d]pyrimidin-2-amine;

5-(2-fluorophenyl)-4-methoxy-N-(4-((4-methylpiperazin-1-yl)methyl)phenyl)-7H -pyrrolo[2,3-d]pyrimidin-2-amine;

5-(4-chlorophenyl)-4-methoxy-N-(4-((4-methylpiperazin-1-yl)methyl)phenyl)-7H -pyrrolo[2,3-d]pyrimidin-2-amine;

4-(4-methoxy-2-((4-((4-methylpiperazin-1-yl)methyl) phenyl)amino)-7H-pyrrolo[2, 3-d]pyrimidin-5-yl)-N,N-dimethylbenzamide;

4-(4-methoxy-2-((4-((4-methylpiperazin-1-yl)methyl) phenyl)amino)-7H-pyrrolo[2, 3-d]pyrimidin-5-yl)-N,N-dimethylbenzenesulfonamide;

4-(4-methoxy-2-((4-((4-methylpiperazin-1-yl)methyl) phenyl)amino)-7H-pyrrolo[2, 3-d]pyrimidin-5-yl)phenol;

3-(4-methoxy-2-((4-((4-methylpiperazin-1-yl)methyl) phenyl)amino)-7H-pyrrolo[2, 3-d]pyrimidin-5-yl)phenol;

N-(4-((4-ethylpiperazin-1-yl)methyl)phenyl)-5-(2-fluoro-4-(pyridin-2-ylmethoxy) phenyl)-4-(2-methoxyethoxy)-7H-pyrrolo[2,3-d]pyrimidin-2-amine;

4-methoxy-5-(4-methoxy phenyl)-N-(4-((4-methyl piperazin-1-yl)methyl)phenyl)-7H -pyrrolo[2,3-d] pyrimidin-2-amine 4-methoxy-5-(3-methoxy phenyl)-N-(4-((4-methyl piperazin-1-yl)methyl)phenyl)-7H -pyrrolo[2,3-d] pyrimidin-2-amine;

4-(4-methoxy-2-((6-((4-methyl piperazin-1 -yl)methyl) pyridin-3-yl)amino)-7H -pyrrolo[2,3-d]pyrimidin-5-yl)-N,N-dimethylbenzenesulfonamide;

N,N-dimethyl-4-(2-((4-((4-methylpiperazin-1-yl)methyl) phenyl)amino)-4- (methylthio) -7H-pyrrolo[2,3-d]pyrimidin-5-yl)benzenesulfonamide;

methyl 3-(4-methoxy-2-((4-((4-methylpiperazin-1-yl)methyl)phenyl)amino)-7H -pyrrolo[2,3-d]pyrimidin-5-yl)benzoate;

5-(2,4-difluorophenyl)-4-methoxy-N-(4-((4-methylpiperazin-1-yl)methyl)phenyl)-7H- pyrrolo[2,3-d]pyrimidin-2-amine;

N-(4-(4-methoxy-2-((4-((4-methylpiperidin-1-yl)methyl) phenyl)amino)- 7H-pyrrolo[2, 3-d]pyrimidin-5-yl)phenyl)-1,5-dimethyl-1H-pyrazole-3-carboxamide;

4-(4-methoxy-2-((6-((4-methylpiperazin-l-yl)methyl) pyridin-3-yl)amino)-7H -pyrrolo[2,3-d]pyrimidin-5-yl) phenol;

4-(4-methoxy-2-(4-((4-methyl piperidin-1-yl)methyl) phenyl)amino)-7H-pyrrolo[2,3-d] pyrimidin-5-yl)phenol;

N-(3-(4-methoxy-2-((4-((4-methyl piperidin-l-yl)methyl) phenyl)amino)-7H-pyrrolo [2,3-d] pyrimidin-5-yl) phenyl)-1,5-dimethyl-1H-pyrazole-3-carboxamide;

5-(2,4-difluorophenyl)-4-methoxy-N-(4-((4-methyl piperidin-1-yl)methyl)phenyl)-7H -pyrrolo[2,3-d]pyrimidin-2-amine;

4-methoxy-N-(4-((4-methyl piperidin-1-yl) methyl)phenyl)-5-(o-tolyl)-7H-pyrrolo[2,3-d] pyrimidin-2-amine;

4-methoxy-N-(4-((4-methylpiperidin-1-yl)methyl)phenyl)-5-(m-tolyl)-7H-pyrrolo[2, 3-d]pyrimidin-2-amine;

4-methoxy-N-(4-((4-methylpiperidin-1-yl)methyl)phenyl)-5-(p-tolyl)-7H-pyrrolo[2, 3-d]pyrimidin-2-amine;

5-(2-fluoro-4-(pyrimidin-2-ylmethoxy)phenyl)-4-(2-methoxyethoxy)-N-(4-((4-methylpiperidin-1-yl) methyl)phenyl)-7H-pyrrolo[2,3-d]pyrimidin-2-amine;

5-(3-(dimethylamino)phenyl)-4-methoxy-N-(4-((4-methylpiperazin-1-yl)methyl)phenyl)-7H -pyrrolo[2,3-d]pyrimidin-2-amine;

5-(2-chlorophenyl)-4-methoxy-N-(4-((4-methylpiperazin-l-yl)methyl)phenyl)-7H -pyrrolo[2,3-d]pyrimidin-2-amine;

5-(3-chlorophenyl)-4-methoxy-N-(4-((4-methylpiperazin-1-yl)methyl)phenyl)-7H -pyrrolo[2,3-d]pyrimidin-2-amine;

5-(4-fluorophenyl)-4-methoxy-N-(4-((4-methylpiperazin-1-yl)methyl)phenyl)-7H -pyrrolo[2,3-d]pyrimidin-2-amine;

N-(4-((4-ethylpiperazin-1-yl)methyl)phenyl)-5-(2-fluoro-4-(pyrimidin-2-ylmethoxy) phenyl)-4-(2-methoxyethoxy)-7H-pyrrolo[2,3-d]pyrimidin-2-amine;3-(4-methoxy-2- ((4-((4-methylpiperazin-1-yl)methyl) phenyl)amino)-7H-pyrrolo[2,3-d]pyrimidin-5-yl)-N,N-dimethylbenzamide;

4-(4-methoxy-2-((4-((4-methylpiperidin-1-yl)methyl) phenyl)amino)-7H-pyrrolo[2, 3-d]pyrimidin-5-yl)benzenesulfonamide;

4-(2-((6-((4-ethylpiperazin-1-yl)methyl)pyridin-3-yl) amino)-4-methoxy-7H-pyrrolo[2, 3-d]pyrimidin-5-yl) phenol;

5-(6-fluoropyridin-3-yl)-4-methoxy-N-(4-((4-methylpiperazin-1-yl)methyl)phenyl)-7H -pyrrolo[2,3-d]pyrimidin-2-amine;

5-(4-(benzyloxy)-3-methoxyphenyl)-4-methoxy-N-(4-((4-methylpiperidin-1-yl) methyl)phenyl)-7H-pyrrolo[2,3-d]pyrimidin-2-amine;

5-(2,4-difluorophenyl)-N-(4-((4-ethylpiperazin-1-yl) methyl)phenyl)-4-methoxy-7H -pyrrolo[2,3-d]pyrimidin-2-amine;

5-(4-(benzyloxy)-2-fluorophenyl)-4-methoxy-N-(4-((4-methylpiperazin-1-yl) methyl)phenyl)-7H-pyrrolo[2,3-d]pyrimidin-2-amine;

4-methoxy-N-(4-((4-methylpiperazin-1-yl)methyl)phenyl)-5-(3,4,5-trimethoxyphenyl)-7H -pyrrolo[2,3-d]pyrimidin-2-amine;

4-(2-((4-((4-ethylpiperazin-1-yl)methyl)phenyl)amino)-4-methoxy-7H-pyrrolo[2, 3-d]pyrimidin-5-yl)phenol;

5-(2-fluoro-4-methylphenyl)-4-methoxy-N-(4-((4-methylpiperazin-1-yl)methyl)phenyl)-7H -pyrrolo[2,3-d] pyrimidin-2-amine;

5-(3-chloro-4-fluorophenyl)-4-(2-methoxyethoxy)-N-(4-((4-methylpiperazin-1-yl) methyl)phenyl)-7H-pyrrolo[2,3-d]pyrimidin-2-amine;

5-(3-chloro-4-fluorophenyl)-4-methoxy-N-(4-((4-methylpiperazin-1-yl)methyl)phenyl)-7H -pyrrolo[2,3-d] pyrimidin-2-amine;

5-(2,4-difluoro phenyl)-N-(4-((4-methyl piperazin-1-yl) methyl)phenyl)-4-((tetrahydro furan-2-yl) methoxy)-7H-pyrrolo[2,3-d] pyrimidin-2-amine;

5-(2,4-difluoro phenyl)-4-(2-methoxyethoxy)-N-(4-((4-methylpiperazin-1-yl)methyl) phenyl)-7H-pyrrolo[2,3-d] pyrimidin-2-amine;

5-(2,4-difluoro phenyl)-N4-ethyl-N2-(4-((4-methyl piperazin-1-yl) methyl) phenyl)-7H-pyrrolo[2,3-d] pyrimidine-2,4-diamine;

4-(cyclopentyl oxy)-5-(2,4-di fluorophenyl)-N-(4-((4-methylpiperazin-1-yl)methyl) phenyl)-7H-pyrrolo[2,3-d]pyrimidin-2-amine;

5-(4-(benzyl oxy)-3-methoxyphenyl)-N-(4-((4-ethylpiperazin-1-yl)methyl) phenyl)-4-methoxy-7H-pyrrolo[2,3-d] pyrimidin-2-amine;

4-methoxy-5-(4-((2-methoxy ethoxy)methoxy)phenyl)-N-(4-((4-methyl piperazin-1-yl) methyl)phenyl)-7H-pyrrolo[2,3-d]pyrimidin-2-amine;

5-(3-chloro-4-fluorophenyl)-N-(4-((4-ethyl piperazin-1-yl) methyl)phenyl)-4-methoxy-7H-pyrrolo [2,3-d] pyrimidin-2-amine;

5-(2,4-difluoro phenyl)-4-ethoxy-N-(4-((4-methyl piperazin-1-yl) methyl)phenyl)-7H-pyrrolo [2,3-d] pyrimidin-2-amine;

2-fluoro-5-(4-methoxy-2-((4-((4-methyl piperazin-1-yl) methyl)phenyl)amino)-7H-pyrrolo[2,3-d] pyrimidin-5-yl)-N-methyl benzamide;

N-(4-((4-ethyl piperazin-1-yl) methyl)phenyl)-4-methoxy-5-(3-methoxy-4-((2-methoxy ethoxy) methoxy)phenyl)-7H-pyrrolo[2,3-d]pyrimidin-2-amine;

5-(2-aminopyrimidin-5-yl)-4-(2-methoxyethoxy)-N-(4-((4-methylpiperazin-1-yl) methyl)phenyl)-7H-pyrrolo[2,3-d]pyrimidin-2-amine;

5-(2,4-difluorophenyl)-4-((1-methoxypropan-2-yl)oxy)-N-(4-((4-methylpiperazin-1-yl) methyl)phenyl)-7H-pyrrolo[2,3-d]pyrimidin-2-amine;

4-(2-methoxy ethoxy)-5-(2-methylbenzo[d] oxazol-6-yl)-N-(4-((4-methyl piperazin-1-yl) methyl)phenyl)-7H-pyrrolo [2,3-d] pyrimidin-2-amine;

6-(4-(2-metho xyethoxy)-2-((4-((4-methyl piperazin-1-yl)methyl)phenyl)amino)-7H-pyrrolo[2,3-d] pyrimidin-5-yl)-2-methyl quinazolin-4(1H)-one;

4,4'-(2-((4-((4-methylpiperidin-1-yl)methyl) phenyl)amino)-7H-pyrrolo [2,3-d] pyrimidine-4,5-diyl)bis(N,N-dimethyl benzenesulfonamide);

5-(2-methyl benzo[d]oxazol-6-yl)-N-(4-((4-methyl piperazin-1-yl)methyl) phenyl)-4-((tetrahydrofuran-2-yl) methoxy)-7H-pyrrolo [2,3-d] pyrimidin-2-amine;

1-((3-fluoro-4-(4-(2-methoxyethoxy)-2-((4-((4-methylpiperazin-1-yl) methyl)phenyl)amino)-7H-pyrrolo[2,3-d]pyrimidin-5-yl)phenoxy)methyl)pyridin-2(1H)-one;5-(2,4-difluorophenyl)-4-isopropoxy-N-(4-((4-methylpiperazin-1-yl)methyl)phenyl)-7H -pyrrolo[2,3-d]pyrimidin-2-amine;

5 -(4-(benzyloxy)-3-methoxyphenyl)-4-methoxy-N-(4-((4-methylpiperazin-1-yl) methyl)phenyl)-7H-pyrrolo[2,3-d]pyrimidin-2-amine;

5-(3-chloro-4-fluorophenyl)-N-(4-((4-ethylpiperazin-1-yl)methyl) phenyl)-4-(2-methoxyethoxy)-7H-pyrrolo[2,3-d]pyrimidin-2-amine;

4-methoxy-5-(2-methylbenzo[d]oxazol-6-yl)-N-(4-((4-methylpiperazin-1-yl) methyl)phenyl)-7H-pyrrolo[2,3-d]pyrimidin-2-amine;

5-(3-methoxy-4-((6-methylpyridin-3-yl)methoxy)phenyl)-4-(2-methoxyethoxy)-N-(4-((4-methylpiperazin-1-yl)methyl)phenyl)-7H-pyrrolo[2,3-d]pyrimidin-2-amine;

5-(2,4-difluorophenyl)-N2-(4-((4-methylpiperazin-1-yl) methyl)phenyl)-N4-((tetrahydro-2H -pyran-4-yl) methyl)-7H-pyrrolo[2,3-d]pyrimidine-2,4-diamine;

5-(2,4-difluorophenyl)-N2-(4-((4-methylpiperazin-1-yl) methyl)phenyl)-N4-(tetrahydro-2H -pyran-4-yl)-7H-pyrrolo[2,3-d]pyrimidine-2,4-diamine;

N-(4-(4-(2-methoxyethoxy)-2-((4-((4-methylpiperazin-1-yl)methyl)phenyl)amino)-7H -pyrrolo[2,3-d]pyrimidin-5-yl)phenyl)-1,5-dimethyl-1H-pyrazole-3- carboxamide;

5-(3-chloro-4-fluorophenyl)-N-(4-((4-methylpiperazin-1-yl)methyl)phenyl)-4-((tetrahydrofuran-2-yl)methoxy)-7H-pyrrolo[2,3-d]pyrimidin-2-amine;

5-(2,4-difluorophenyl)-4-(2-methoxyethoxy)-N-(3-((4-methylpiperazin-1-yl) methyl)phenyl)-7H-pyrrolo[2,3-d]pyrimidin-2-amine;

4-(4-(2-methoxyethoxy)-2-((4-((4-methylpiperazin-1-yl) methyl)phenyl)amino)-7H -pyrrolo[2,3-d]pyrimidin-5-yl)-N,N-dimethylbenzenesulfonamide;

5-(2,4-difluorophenyl)-N-(4-((dimethylamino)methyl)phenyl)-4-(2-methoxyethoxy)-7H -pyrrolo[2,3-d]pyrimidin-2-amine;

4-(4-(2-methoxyethoxy)-2-((4-((4-methylpiperazin-1-yl) methyl)phenyl)amino)-7H -pyrrolo[2,3-d]pyrimidin-5-yl)benzonitrile;

4-(4-methoxy-2-((4-((4-methylpiperazin-1-yl)methyl)phenyl)amino)-7H-pyrrolo [2, 3-d]pyrimidin-5-yl)benzonitrile;

4-(2-methoxyethoxy)-N-(4-((4-methylpiperazin-1-yl) methyl)phenyl)-5-(4-(trifluoromethoxy)phenyl)-7H-pyrrolo[2,3-d]pyrimidin-2-amine;

4-(2-methoxyethoxy)-N-(4-((4-methylpiperazin-1-yl) methyl)phenyl)-5-(4-(trifluoromethyl)phenyl)-7H-pyrrolo[2,3-d]pyrimidin-2-amine;

5-(4-fluorophenyl)-4-(2-methoxyethoxy)-N-(4-((4-methylpiperazin-1-yl)methyl) phenyl)-7H-pyrrolo[2,3-d]pyrimidin-2-amine;

N,N-diethyl-4-(4-(2-methoxyethoxy)-2-((4-((4-methylpiperazin-1-yl) methyl)phenyl)amino)-7H-pyrrolo[2,3-d]pyrimidin-5-yl)benzenesulfonamide;

5-(4-((3, 5 -dimethylpiperidin-1-yl)sulfonyl)phenyl)-4-(2-methoxyethoxy)-N-(4-((4-methylpiperazin-1-yl) methyl)phenyl)-7H-pyrrolo[2, 3 -d]pyrimidin-2-amine;

4-(2-methoxyethoxy)-N-(4-((4-methylpiperazin-1-yl) methyl)phenyl)-5-(4-(morpholinosulfonyl)phenyl)-7H-pyrrolo[2,3-d]pyrimidin-2-amine;

5-(4-(i sopropylsulfonyl)phenyl)-4-(2-methoxyethoxy)-N-(4-((4-methylpiperazin-1-yl) methyl)phenyl)-7H-pyrrolo[2,3 -d]pyrimidin-2-amine;

5-(4-(benzyloxy)-2-fluorophenyl)-4-(2-methoxyethoxy)-N-(4-((4-methylpiperazin-1-yl) methyl)phenyl)-7H-pyrrolo[2,3-d]pyrimidin-2-amine;

3-fluoro-4-(4-(2-methoxyethoxy)-2-((4-((4-methylpiperazin-1-yl)methyl)phenyl) amino)-7H-pyrrolo[2,3-d]pyrimidin-5-yl)-N,N-dimethylbenzenesulfonamide;

5-(2-fluoro-4-(pyridin-2-ylmethoxy)phenyl)-4-(2-methoxyethoxy)-N-(4-((4-methylpiperazin-1-yl) methyl)phenyl)-7H-pyrrolo[2,3-d]pyrimidin-2-amine;

5-(2-fluoro-4-(pyridin-4-ylmethoxy)phenyl)-4-(2-methoxyethoxy)-N-(4-((4-methylpiperazin-1-yl) methyl)phenyl)-7H-pyrrolo[2,3 -d]pyrimidin-2-amine;

5-(4-(azetidin-1-ylsulfonyl)phenyl)-4-(2-methoxyethoxy)-N-(4-((4-methylpiperazin-1-yl) methyl)phenyl)-7H-pyrrolo[2,3-d]pyrimidin-2-amine;

5-(2-fluoro-4-(pyridin-3-ylmethoxy)phenyl)-4-(2-methoxyethoxy)-N-(4-((4-methylpiperazin-1-yl) methyl)phenyl)-7H-pyrrolo[2,3-d]pyrimidin-2-amine;

3-fluoro-4-(4-(2-methoxyethoxy)-2-((4-((4-methylpiperazin-1-yl)methyl)phenyl) amino)-7H-pyrrolo[2,3-d]pyrimidin-5-yl)phenol;

4-(2-methoxyethoxy)-5-(1-methyl-1H-indazol-5-yl)-N-(4-((4-methylpiperazin-1-yl) methyl)phenyl)-7H-pyrrolo[2,3-d]pyrimidin-2-amine;

4-(2-methoxyethoxy)-N-(4-((4-methylpiperazin-1-yl)methyl)phenyl)-5-(4-(piperidin-1-ylsulfonyl) phenyl)-7H-pyrrolo[2,3-d]pyrimidin-2-amine;

5-(2-fluoro-4-((4-methoxypyridin-3-yl)methoxy)phenyl)-4-(2-methoxyethoxy)-N-(4-((4-methylpiperazin-1-yl)methyl)phenyl)-7H-pyrrolo[2,3-d]pyrimidin-2-amine;

5-(2-fluoro-4-((5-methoxypyridin-3-yl)methoxy)phenyl)-4-(2-methoxyethoxy)-N-(4-((4-methylpiperazin-1-yl)methyl)phenyl)-7H-pyrrolo[2,3-d]pyrimidin-2-amine;

5-(4-(2-methoxyethoxy)-2-((4-((4-methylpiperazin-1-yl)methyl)phenyl)amino)-7H -pyrrolo[2,3 -d]pyrimidin-5-yl)-2-methyl-2,3-dihydroisothiazolo[4,5-b]pyridine 1,1-dioxide;

4-(2-methoxyethoxy)-N-(4-((4-methylpiperazin-1-yl)methyl)phenyl)-5-(4-((4-methylpiperazin-1-yl)sulfonyl)phenyl)-7H-pyrrolo[2,3-d]pyrimidin-2-amine;

5-(2-fluoro-4-((6-methylpyridin-2-yl)methoxy)phenyl)-4-(2-methoxyethoxy)-N-(4-((4-methylpiperazin-1-yl)methyl)phenyl)-7H-pyrrolo[2,3-d]pyrimidin-2-amine;

5-(2-fluoro-4-((6-fluoropyridin-2-yl)methoxy)phenyl)-4-(2-methoxyethoxy)-N-(4-((4-methylpiperazin-1-yl)methyl)phenyl)-7H-pyrrolo [2,3-d]pyrimidin-2-amine;

5-(2-fluoro-4-((5-methoxypyridin-2-yl)methoxy)phenyl)-4-(2-methoxyethoxy)-N-(4-((4-methylpiperazin-1-yl)methyl)phenyl)-7H-pyrrolo[2,3-d]pyrimidin-2-amine;

2-(4-(4-(2-methoxyethoxy)-2-((4-((4-methylpiperazin-1-yl)methyl)phenyl)amino)-7H -pyrrolo[2,3-d]pyrimidin-5-yl)phenyl)propan-2-ol;

5-(2-fluoro-4-(pyrimidin-2-ylmethoxy)phenyl)-4-(2-methoxyethoxy)-N-(4-((4-methylpiperazin-1-yl)methyl)phenyl)-7H-pyrrolo[2,3-d]pyrimidin-2-amine;

5-(2-fluoro-4-((3-methyl-4-(2,2,2-trifluoroethoxy)pyridin-2-yl)methoxy)phenyl)-4-(2-methoxyethoxy)-N-(4-((4-methylpiperazin- 1-yl)methyl)phenyl)-7H-pyrrolo[2,3-d]pyrimidin-2-amine;

5-(2-fluoro-4-(pyridin-2-ylmethoxy)phenyl)-4-(2-methoxyethoxy)-N-(4-((4-methylpiperidin-1-yl)methyl)phenyl)-7H-pyrrolo[2,3-d]pyrimidin-2-amine;

4-(2-methoxyethoxy)-N-(4-((4-methylpiperazin-1-yl)methyl)phenyl)-5-(4-(pyridin-2-ylmethoxy) phenyl)-7H-pyrrolo[2,3-d]pyrimidin-2-amine;

5-(2-fluoro-4-((3-methylpyridin-2-yl)methoxy)phenyl)-4-(2-methoxyethoxy)-N-(4-((4-methylpiperidin-1-yl)methyl)phenyl)-7H-pyrrolo[2,3-d]pyrimidin-2-amine;

N-(4-((4-ethylpiperazin-1-yl)methyl)phenyl)-5-(2-fluoro-4-((3-methylpyridin-2-yl) methoxy)phenyl)-4-(2-methoxyethoxy)-7H-pyrrolo[2,3-d]pyrimidin-2-amine;

or a tautomer, stereoisomer, isotopologue, or salt thereof.

11. A pharmaceutical composition comprising a compound according to claim 1, or a tautomer, stereoisomer, isotopologue, or a prodrug thereof, or a pharmaceutically acceptable salt thereof, and a pharmaceutically acceptable diluent or carrier.

12. A method of treating disease or disorder mediated by Tyro3, Axl, and/or Mer kinase, the method comprising administering to a subject in need thereof an effective amount of the compound of claim 1, or a tautomer, stereoisomer, isotopologue, or salt thereof.

13. The method according to claim 12, wherein the disease or disorder is a cancer.

14. The method according to claim 13, wherein the cancer is selected from the group consisting of lung cancer, colon cancer, colorectal cancer, breast cancer, prostate cancer, liver cancer, pancreatic cancer, bladder cancer, gastric cancer, renal cancer, salivary gland cancer, ovarian cancer, uterine body cancer, cervical cancer, oral cancer, skin cancer, brain cancer, lymphoma, or leukemia.

15. The method according to claim 12, or a tautomer, stereoisomer, isotopologue, or salt thereof, wherein G is $N(R^9)(R^{10}$, in which each of $R^9$ and $R^{10}$, independently, is $C_{1-8}$ alkyl, $C_{3-8}$ cycloalkyl, $C_{3-8}$ heterocyclyl, aryl, or heteroaryl, or, $R^9$ and $R^{10}$, together with the atom to which they are attached, form $C_{3-8}$ heterocyclyl.

16. The method according to claim 12, or a tautomer, stereoisomer, isotopologue, or salt thereof, wherein L is O.

17. The method according to claim 15, or a tautomer, stereoisomer, isotopologue, or salt thereof, wherein G is $N(R^9)(R^{10})$ or $C_{3-8}$ heterocyclyl.

18. The method according to claim 17, or a tautomer, stereoisomer, isotopologue, or salt thereof, wherein G is $C_{3-8}$ heterocyclyl.

19. The method according to claim 18, or a tautomer, stereoisomer, isotopologue, or salt thereof, wherein the $C_{3-8}$ heterocyclyl is a 5- or 6-membered ring.

20. The method according to claim 19, or a tautomer, stereoisomer, isotopologue, or salt thereof, wherein G is

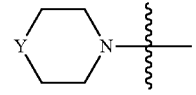

optionally substituted with one or more $C_{1-8}$ alkyl, in which Y is O, —NR, or —CR'R", each of R, R', and R", independently, being H, OH, $NH_2$, or $C_{1-8}$ alkyl.

* * * * *